(12) United States Patent
Ishikura et al.

(10) Patent No.: US 10,973,463 B2
(45) Date of Patent: Apr. 13, 2021

(54) INFORMATION PROCESSING DEVICE

(71) Applicant: SONY CORPORATION, Tokyo (JP)

(72) Inventors: Masayuki Ishikura, Kanagawa (JP); Yoshio Oguchi, Tokyo (JP); Takashi Kubodera, Chiba (JP); Kazuaki Takahashi, Aichi (JP); Hiroshi Nakayama, Tokyo (JP); Kazuhiro Nakagomi, Tokyo (JP)

(73) Assignee: SONY CORPORATION, Tokyo (JP)

( * ) Notice: Subject to any disclaimer, the term of this patent is extended or adjusted under 35 U.S.C. 154(b) by 315 days.

(21) Appl. No.: 16/061,804

(22) PCT Filed: Dec. 29, 2016

(86) PCT No.: PCT/JP2016/089221
§ 371 (c)(1),
(2) Date: Jun. 13, 2018

(87) PCT Pub. No.: WO2017/119403
PCT Pub. Date: Jul. 13, 2017

(65) Prior Publication Data
US 2018/0360383 A1    Dec. 20, 2018

Related U.S. Application Data

(60) Provisional application No. 62/276,554, filed on Jan. 8, 2016.

(51) Int. Cl.
*A61B 5/00*    (2006.01)
*A63B 60/46*    (2015.01)
(Continued)

(52) U.S. Cl.
CPC .......... *A61B 5/6895* (2013.01); *A61B 5/0077* (2013.01); *A61B 5/1122* (2013.01);
(Continued)

(58) Field of Classification Search
CPC . A63B 69/3608; A63B 60/46; A63B 24/0003; A63B 69/38; A63B 71/0622;
(Continued)

(56) References Cited

U.S. PATENT DOCUMENTS 5,197,489 A * 3/1993 Conlan .................... A61B 5/11
600/595
6,619,836 B1    9/2003 Silvant et al.
(Continued)

FOREIGN PATENT DOCUMENTS

CN    1324030 A    11/2001
CN    1337016 A    2/2002
(Continued)

OTHER PUBLICATIONS

International Search Report and Written Opinion of PCT Application No. PCT/JP2016/089221, dated Apr. 4, 2017, 09 pages of ISRWO.

(Continued)

*Primary Examiner* — Benjamin R Schmitt
(74) *Attorney, Agent, or Firm* — Chip Law Group

(57) ABSTRACT

An information processing device includes a first member that includes a substantially plate-shaped casing and a predetermined detection unit, a second member that includes a substantially plate-shaped casing and that holds a battery inside the second member, and a connection unit that includes an elastic body and connects a part of an outer circumferential end surface of the first member to a part of an outer circumferential end surface of the second member such that a surface direction of one surface of the first member substantially matches a surface direction of one surface of the second member. The information processing device is worn on a predetermined body part such that the
(Continued)

one surface of the first member and the one surface of the second member are located on a side of the body part.

11 Claims, 54 Drawing Sheets

(51) Int. Cl.

| | | |
|---|---|---|
| *G01D 11/30* | (2006.01) | |
| *G01D 11/24* | (2006.01) | |
| *A61B 5/11* | (2006.01) | |
| *A63B 69/36* | (2006.01) | |
| *G01P 13/00* | (2006.01) | |
| *A63B 24/00* | (2006.01) | |
| *A63B 69/38* | (2006.01) | |
| *A63B 71/06* | (2006.01) | |
| *A63B 102/02* | (2015.01) | |
| *A63B 102/32* | (2015.01) | |

(52) U.S. Cl.
CPC .......... *A63B 60/46* (2015.10); *A63B 69/3608* (2013.01); *G01D 11/245* (2013.01); *G01D 11/30* (2013.01); *G01P 13/00* (2013.01); *A61B 5/11* (2013.01); *A63B 24/0003* (2013.01); *A63B 24/0006* (2013.01); *A63B 69/36* (2013.01); *A63B 69/38* (2013.01); *A63B 71/0622* (2013.01); *A63B 2024/0009* (2013.01); *A63B 2024/0015* (2013.01); *A63B 2024/0028* (2013.01); *A63B 2024/0096* (2013.01); *A63B 2102/02* (2015.01); *A63B 2102/32* (2015.10); *A63B 2209/00* (2013.01); *A63B 2220/803* (2013.01); *A63B 2220/833* (2013.01); *A63B 2220/836* (2013.01); *A63B 2225/50* (2013.01)

(58) Field of Classification Search
CPC ........ A63B 2024/0096; A63B 2209/00; A63B 69/36; A63B 2102/02; A63B 2102/32; A63B 24/0006; A63B 2024/0009; A63B 2024/0015; A63B 2024/0028; A63B 2220/803; A63B 2220/833; A63B 2220/836; A63B 2225/50; A61B 5/6895; A61B 5/0077; A61B 5/1122; A61B 5/11; G01D 11/30; G01D 11/245; G01P 13/00
See application file for complete search history.

(56) References Cited

U.S. PATENT DOCUMENTS

| | | |
|---|---|---|
| 2001/0043514 A1 | 11/2001 | Kita |
| 2016/0367172 A1 | 12/2016 | Kuroda et al. |

FOREIGN PATENT DOCUMENTS

| | | |
|---|---|---|
| EP | 1145085 B1 | 9/2008 |
| JP | 02-141882 A | 11/1990 |
| JP | 02-141882 U | 11/1990 |
| JP | 2002-40175 A | 2/2002 |
| JP | 2002-040175 A | 2/2002 |
| JP | 2003-514231 A | 4/2003 |
| JP | 2005-055249 A | 3/2005 |
| JP | 2005-055335 A | 3/2005 |
| JP | 2005-55335 A | 3/2005 |
| JP | 4763200 B2 | 8/2011 |
| JP | 2013-192591 A | 9/2013 |
| JP | 2014-097263 A | 5/2014 |
| JP | 2015-171469 A | 10/2015 |
| KR | 10-0408009 B1 | 12/2003 |
| TW | 638359 B | 6/2003 |
| WO | 2001/035173 A1 | 5/2001 |
| WO | 2015/136879 A1 | 9/2015 |

OTHER PUBLICATIONS

Office Action for JP Patent Application No. 2017-560378, dated Dec. 15, 2020, 03 pages of Office Action and 03 pages of English Translation.

\* cited by examiner

FIG. 19 v140

| | Green | | |
|---|---|---|---|
| ALL | Month | Week | Day |

08/20/2015

| | Shots | Average (yards) | Best (yards) |
|---|---|---|---|
| ▸ 1W | | 210 | 235 |
| ▸ 3W | 0 | 197 | 220 |
| ▸ 5I | 0 | 153 | 170 |
| ▸ 6I | 03 | 140 | 160 |
| ▸ 7I | | 120 | 150 |
| ▸ 8I | 2 | 125 | 140 |
| ▸ 9I | 0 | 115 | 130 |
| ▸ PW | 4 | 90 | 115 |
| ▸ AW | 5 | 97 | 100 |
| ▸ SW | 2 | 75 | 80 |

<SELECTING OVERLAP OF CARRY MAPS>

<SHOT DETECTION BALL FLYING ANIMATION>

INFORMATION PROCESSING DEVICE

CROSS REFERENCE TO RELATED APPLICATIONS

This application is a U.S. National Phase of International Patent Application No. PCT/JP2016/089221 filed on Dec. 29, 2016, which claims priority benefit of U.S. Provisional Patent Application No. 62/276,554 filed in the US. Patent Office on Jan. 8, 2016. Each of the above-referenced applications is hereby incorporated herein by reference in its entirety.

TECHNICAL FIELD

The present disclosure relates to an information processing device.

BACKGROUND ART

In recent years, systems or devices that can analyze movements of bodies are necessary in various fields. For example, in the fields of sports, an improvement in competition power has been attempted by analyzing movements (for example, forms) of bodies in tennis or golf swings, pitching or batting of baseball, and the like and finding improvement points from the analysis results.

For example, Patent Literature 1 discloses an example of an exercise analysis device that can analyze a trajectory of a golf club at the time of golf swing on the basis of an optical motion capture technology and a detection result of an exercise of a golf club by an inertial sensor.

CITATION LIST

Patent Literature

Patent Literature 1: JP 2013-192591A

DISCLOSURE OF INVENTION

Technical Problem

On the other hand, in devices or systems analyzing movements of bodies, in a case in which more accurate analysis is necessary, configurations of systems tend to be complicated, for example, large-scale devices are necessary. In such situations, it is necessary to realize structures for realizing systems which can more accurately analyze movements of bodies with simpler configurations.

Accordingly, the present disclosure proposes an information processing device capable of realizing a system that can more accurately analyze a movement of a body with a simpler configuration.

Solution to Problem

According to the present disclosure, there is provided an information processing device including: a first member that includes a substantially plate-shaped casing and a predetermined detection unit; a second member that includes a substantially plate-shaped casing and that holds a battery inside the second member; and a connection unit that includes an elastic body and connects a part of an outer circumferential end surface of the first member to a part of an outer circumferential end surface of the second member such that a surface direction of one surface of the first member substantially matches a surface direction of one surface of the second member. The information processing device is worn on a predetermined body part such that the one surface of the first member and the one surface of the second member are located on a side of the body part.

Advantageous Effects of Invention

According to the present disclosure, as described above, it is possible to provide an information processing device capable of realizing a system that can more accurately analyze a movement of a body with a simpler configuration.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 19 is a diagram illustrating another example of the suggestion screen of information based on the accumulated data in the UI according to the embodiment.

MODE(S) FOR CARRYING OUT THE INVENTION

Figure 1:
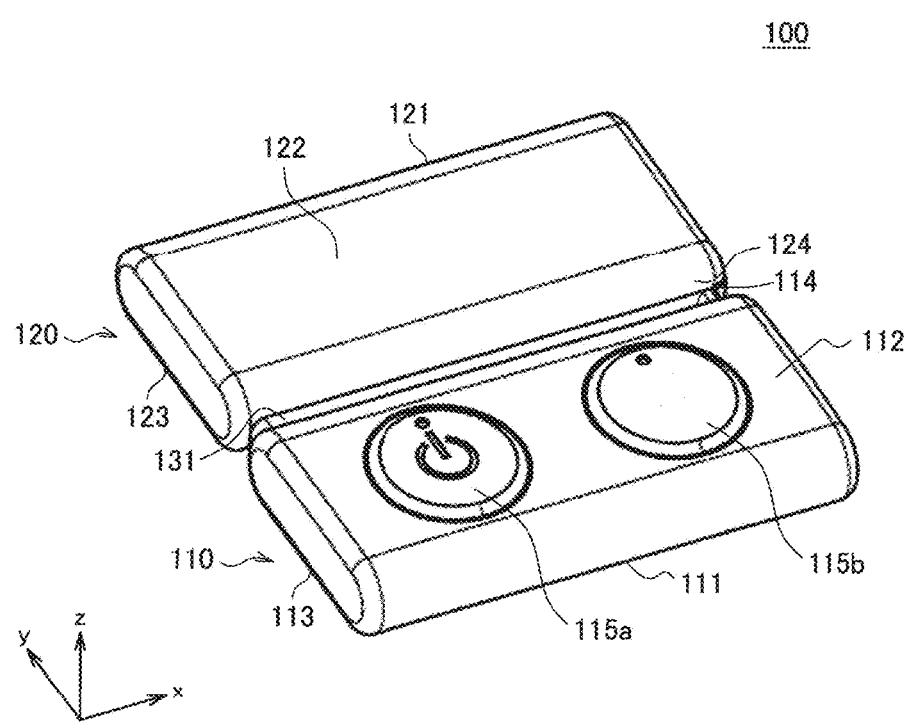
FIG. 1 is a perspective view illustrating an example of a schematic configuration of a body sensor device according to a first embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that the description will be made in the following order.
1. First embodiment: body sensor device
1.1. Exterior example of body sensor device
1.2. Example of internal structure of body sensor device
1.3. Holder
1.4. Example of application
1.5. Evaluation
2. Second embodiment: shaft sensor device
2.1. Exterior example of shaft sensor device
2.2. Configurations of body unit and mounting unit
2.3. Evaluation
3. Third embodiment: information processing system
3.1. System configuration
3.2. UI
3.3. Evaluation
4. Conclusion 1. First Embodiment: Body Sensor Device <1.1. Exterior Example of Body Sensor Device>

A body sensor device will be described according to a first embodiment of the present disclosure will be described. First, an example of a schematic configuration of the body sensor device according to the embodiment will be described. A body sensor device 100 according to the embodiment includes various sensors such as an acceleration sensor and an angular velocity sensor inside its casing, is worn so that a part of the body sensor device comes into contact with a part of a body, and senses a movement of the part of the body (for example, a change in a position or a direction).

Figure 2:
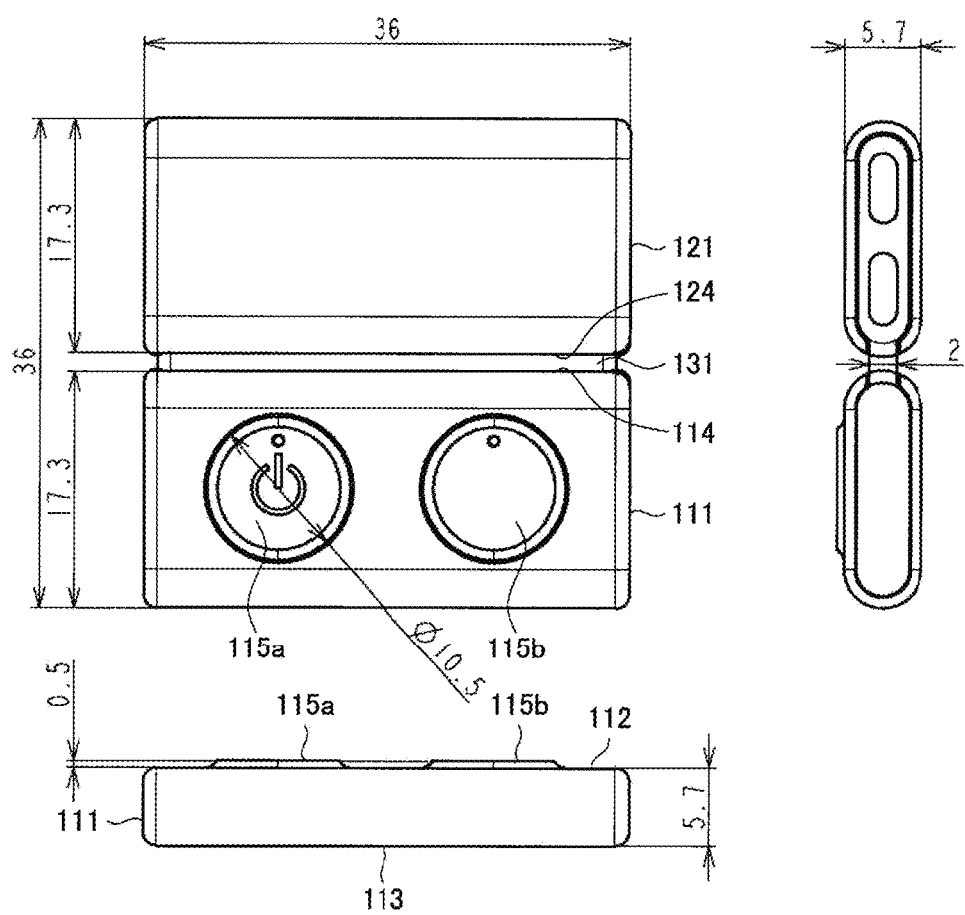
FIG. 2 is a trihedral view illustrating an example of a schematic configuration of the body sensor device according to the embodiment.

For example, FIGS. 1 and 2 illustrate an example of the structure of the body sensor device 100 according to the embodiment. Specifically, FIG. 1 is a perspective view illustrating an example of a schematic configuration of the body sensor device 100 according to the first embodiment. In addition, FIG. 2 is a trihedral view illustrating an example of the schematic configuration of the body sensor device 100 according to the embodiment.

As illustrated in FIGS. 1 and 2, the body sensor device 100 according to the embodiment includes a manipulation unit 110, a battery unit 120, and a connection unit 131. Note that the manipulation unit 110 is equivalent to an example of a "first member." In addition, the battery unit 120 is equivalent to an example of a "second member."

The manipulation unit 110 includes a substantially plate-shaped casing 111. For example, in the example illustrated in FIG. 1, the casing 111 has a rectangular shape (for example, an oblong shape) of which an upper surface 112 and a lower surface 113 having a longitudinal direction and a transverse direction are formed. In addition, a sensor substrate on which various sensors (for example, an acceleration sensor, an angular velocity sensor, and a shock sensor), a communication unit communicating with another device via a wireless communication path on the basis of a communication standard such as Blutooth (registered trademark), and the like are installed is held inside the casing 111. Note that the details of a configuration of the sensor substrate will be described separately later. In addition, an input unit 115 such as a button for manipulating the body sensor device 100 is installed on the upper surface 112 of the casing 111. For example, in the example illustrated in FIG. 1, an input unit 115a for manipulating ON/OFF of power and an input unit 115b for performing a manipulation (for example, a manipulation for ON/OFF, pairing, or the like of the communication unit) of the communication unit are installed as the input unit 115.

Note that in the following description, the longitudinal direction and the transverse direction of the upper surface 112 and the lower surface 113 of the casing 111 are referred to as an x direction and a y direction, respectively. The thickness direction of the casing 111 is also referred to as a z direction.

In addition, the battery unit 120 includes a substantially plate-shaped casing 121. For example, in the example illustrated in FIG. 1, the casing 121 has a rectangular shape (for example, an oblong shape) of which an upper surface 122 and a lower surface 123 having a longitudinal direction and a transverse direction are formed. In addition, a battery is held inside the casing 121. Note that in the battery unit 120, the longitudinal direction of the casing 121 substantially matches the longitudinal direction (the x direction) of the casing 111 of the manipulation unit 110 and an end surface 114 of a part of an outer circumferential end portion of the casing 121 is disposed to face an end surface 124 of a part of an outer circumferential end portion of the casing 121.

The connection unit 131 connects the manipulation unit 110 to the battery unit 120. Specifically, the connection unit 131 connects the end surface 114 of the part of the outer circumferential end surface of the casing 111 of the manipulation unit 110 to the end surface 124 of the part of the outer circumferential end surface of the casing 121 of the battery unit 120. For example, in the example illustrated in FIG. 1, the connection unit 131 connects the end surface 114 to the end surface 124 so that the connection unit 131 bridges a gap between the end surface 114 extending in the longitudinal direction in the outer circumferential end surface of the casing 111 and the end surface 124 extending in the longitudinal direction in the outer circumferential end surface of the casing 111. In addition, at this time, the connection unit 131 connects the manipulation unit 110 to the battery unit 120 so that a surface direction of the lower surface 113 of the casing 111 substantially matches a surface direction of the lower surface 123 of the casing 121. In addition, the connection unit 131 is formed of a material with flexibility (for example, an elastic body) such as rubber or an elastomer, and thus is foldable.

Next, an example of dimensions of each unit of the body sensor device 100 according to the embodiment will be described with reference to FIG. 2. As illustrated in FIG. 2, each of the casing 111 of the manipulation unit 110 and the casing 121 of the battery unit 120 is formed to have a width of 36 mm in the longitudinal direction, a width of 17.3 mm in the transverse direction, and a thickness of 5.7 mm. Note that an end surface (for example, the end surface 114) extending in the longitudinal direction in the outer circumferential end surface of the casing 111 has a curved shape which is arced from the side of the upper surface 112 to the side of the lower surface 113. Similarly, an end surface (for example, the end surface 124) extending in the longitudinal direction in the outer circumferential end surface of the casing 121 has a curved shape which is arced from the side of the upper surface 122 to the side of the lower surface 123.

In addition, the casings 111 and 121 are disposed to be separated by about 1.4 mm between the end surfaces 114 and 124, and the end surfaces 114 and 124 are connected by the connection unit 131. The connection unit 131 is formed to be thinner than the thickness of each of the casings 111 and 121 and is formed to be about 2 mm, for example, in the example illustrated in FIG. 2.

In addition, the input unit 115a installed on the upper surface 112 of the casing 111 has a circular shape with a diameter of 10.5 mm and is installed to protrude from the upper surface 112 by about 0.5 mm.

In this way, the body sensor device 100 according to the embodiment is formed to have a substantially square shape of which four sides are 36 mm when viewed from the upper surface side and have a thickness of about 5.75 mm in a thickest portion.

Figure 3:
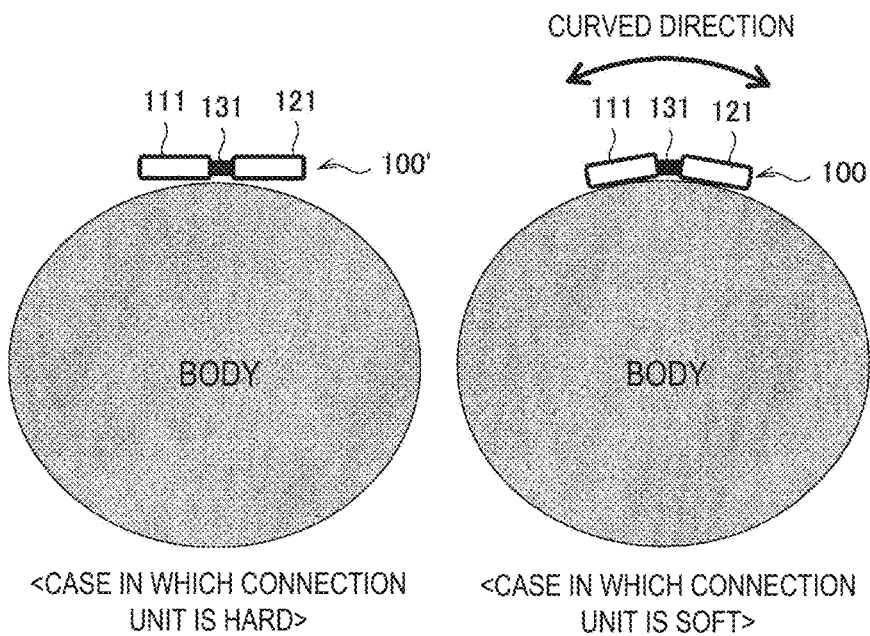
FIG. 3 is an explanatory diagram illustrating an example of a state of the body sensor device according to the embodiment is worn.

On the basis of the above-described configuration, the body sensor device 100 is worn so that the lower surface 113 of the casing 111 of the manipulation unit 110 and the lower surface 123 of the casing 121 of the battery unit 120 come into contact with a part of the body. For example, FIG. 3 is an explanatory diagram illustrating an example of a state of the body sensor device 100 according to the embodiment is worn. Specifically, the right drawing of FIG. 3 illustrates an example of a state of the body sensor device 100 according to the embodiment is worn. Note that the left drawing of FIG. 3 illustrates an example of a state in which a body sensor device 100' is worn in a case in which the connection unit 131 is formed of a hard material according to a comparative example.

As illustrated in the left drawing of FIG. 3, when the connection unit 131 is formed of a hard material in a case in which the body sensor device 100' is worn on a part with a curved shape such as a part of the body, the body sensor device 100' is not disposed along the part of the body in some cases. In these cases, a gap between at least a part of the lower surface of each of the casings 111 and 121 and a part of the body on which the body sensor device 100' is worn occurs, and thus a case in which the body sensor device 100' becomes loose due to a movement of the part of the body can also be assumed. When the body sensor device 100' becomes loose in this way, sensing precision of a movement of a part of the body deteriorates due to a movement of the body sensor device 100' in some cases.

However, the body sensor device 100 according to the embodiment can be folded between the casing 111 of the manipulation unit 110 and the casing 121 of the battery unit 120, as illustrated in the right drawing of FIG. 3, since the connection unit 131 is formed of a soft material. Thus, even in a situation in which the body sensor device 100 is worn on a curved portion such as a part of the body, the lower surface of each of the casings 111 and 121 can come into contact with the part of the body and the body sensor device 100 can be disposed along the part of the body. Therefore, in the body sensor device 100 according to the embodiment, a close contact property with the part of the body is improved more than in the body sensor device 100' illustrated in the left drawing of FIG. 3. Therefore, it is possible to suppress looseness of the body sensor device 100.

Figure 4:
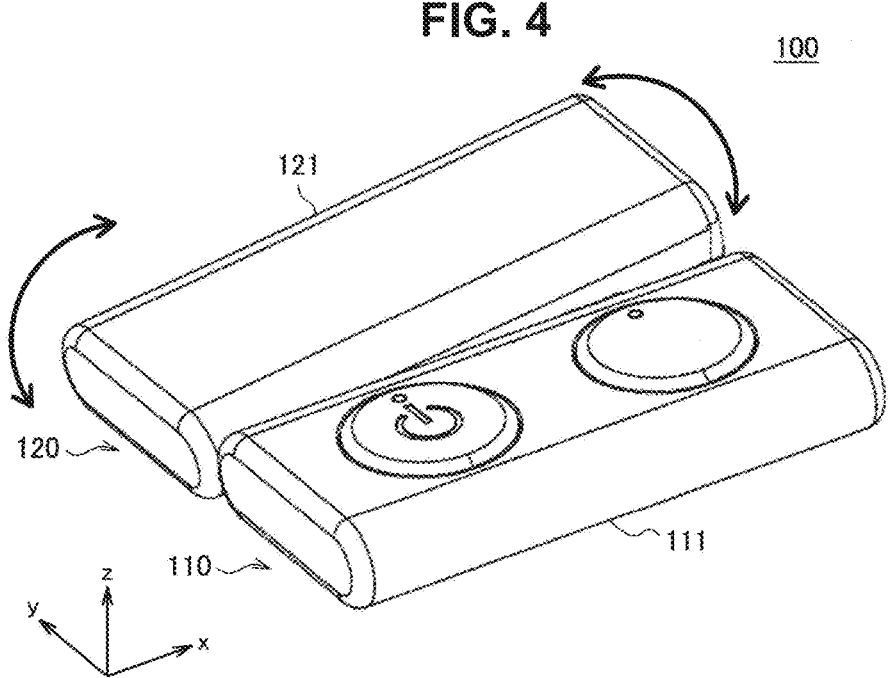
FIG. 4 is an explanatory diagram illustrating an example of a schematic configuration of the body sensor device according to the embodiment.

In addition, FIG. 4 is an explanatory diagram illustrating an example of a schematic configuration of the body sensor device 100 according to the embodiment. FIG. 4 illustrates an example of a movable range of the body sensor device 100. As illustrated in FIG. 4, the body sensor device 100 according to the embodiment can also operate in a direction in which the casing 121 of the battery unit 120 can be twisted relative to the casing 111 of the manipulation unit 110. In this configuration, the body sensor device 100 according to the embodiment can be worn in closer contact with a wider variety of curved surfaces, that is, can be worn in closer contact with a wider variety of parts of the body.

Note that, as will be described in detail later, a wiring (for example, a flexible printed wiring substrate) electrically connecting a sensor substrate held inside the casing 111 of the manipulation unit 110 to a battery held inside the casing 121 of the battery unit 120 is installed inside the connection unit 131. Therefore, a restriction member that restricts excessive folding between the casing 111 of the manipulation unit 110 and the casing 121 of the battery unit 120 may also be installed in the connection unit 131.

Figure 5:
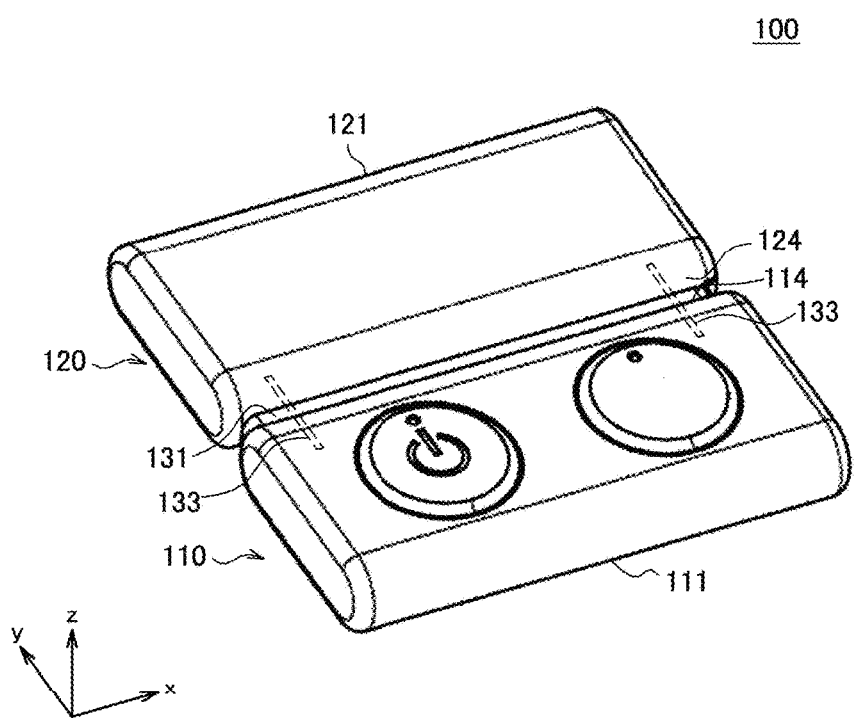
FIG. 5 is an explanatory diagram illustrating an example of a schematic configuration of the body sensor device according to the embodiment.

For example, FIG. 5 is an explanatory diagram illustrating an example of a schematic configuration of the body sensor device 100 according to the embodiment. FIG. 5 illustrates an example of the configuration of a restriction member installed in the connection unit 131. In the example illustrated in FIG. 5, in the connection unit 131, a restriction member 133 with a wire shape is installed to extend from the end surface 114 of the casing 111 of the manipulation unit 110 to the end surface 124 of the casing 121 of the battery unit 120. The restriction member 133 is formed of, for example, a material such as a metal or a resin that is bendable and has higher rigidity than the connection unit 131. In this way, by installing the restriction member 133 in the connection unit 131, it is possible to restrict a movable range of the casing 121 of the battery unit 120 with respect to the casing 111 of the manipulation unit 110. Therefore, for example, it is possible to prevent occurrence of a situation in which a wiring installed in the connection unit 131 is short-circuited due to excessive folding between the casing 111 and the casing 121.

Note that the configuration of the body sensor device 100 described with reference to FIGS. 1 and 2 is merely an example. That is, as illustrated in the right drawing of FIG. 3, the configuration of the body sensor device 100 is not necessarily limited to the examples illustrated in FIGS. 1 and 2 as long as the lower surface 113 of the casing 111 and the lower surface 123 of the casing 121 can be worn in contact with a part of the body. As a specific example, the input unit 115 may also be installed on another end surface different from the end surface 114 (that is, the end surface connected to the end surface 124 of the casing 111 by the connection unit 131) in the outer circumferential end surface of the manipulation unit 110. In addition, the input unit 115 may be formed as an input interface such as a button and may be formed as, for example, another input interface such as a switch or a dial. In addition, the shape of each of the manipulation unit 110 and the battery unit 120 (for example, the shapes of the casings 111 and 121) is merely an example and is not necessarily limited to the oblong shape illustrated in FIGS. 1 and 2. In addition, the configuration of the restriction member 133 described with reference to FIG. 5 is merely an example. That is, the structure of the restriction member 133 or the material of the restriction member 133 is not particularly limited as long as the movable range of the casing 121 of the battery unit 120 with respect to the casing 111 of the manipulation unit 110 can be restricted.

The example of the schematic configuration of the body sensor device according to the embodiment has been described above with reference to FIGS. 1 to 5.

<1.2. Example of Internal Structure of Body Sensor Device>

Next, an example of an inner structure of the body sensor device according to the embodiment will be described. For example, FIG. 6 is an exploded perspective view illustrating an example of a schematic internal structure of the body sensor device according to the embodiment.

Figure 6:
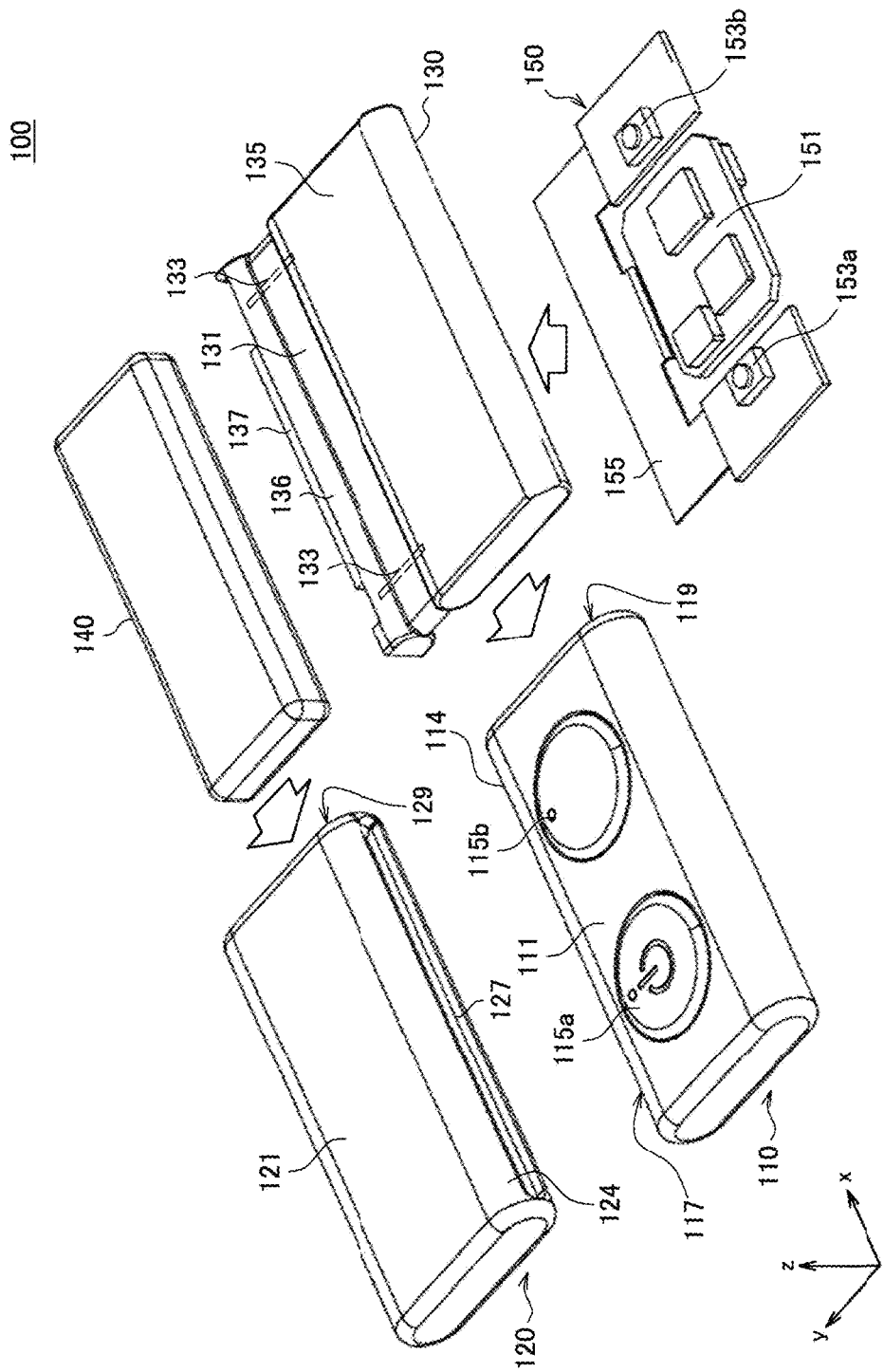
FIG. 6 is an exploded perspective view illustrating an example of a schematic internal structure of the body sensor device according to the embodiment.

As illustrated in FIG. 6 the body sensor device 100 according to the embodiment includes the casing 111 of the manipulation unit 110, the casing 121 of the battery unit 120, a manipulation unit body 130, and a battery 140. In addition, a substrate unit 150 is contained in the manipulation unit body 130. In addition, the manipulation unit body 130 includes a protection unit 135, the connection unit 131, and an engagement unit 136. In addition, the substrate unit 150 includes a sensor substrate 151, pressing type switch units 153a and 153b, and a wiring unit 155.

Figure 7:
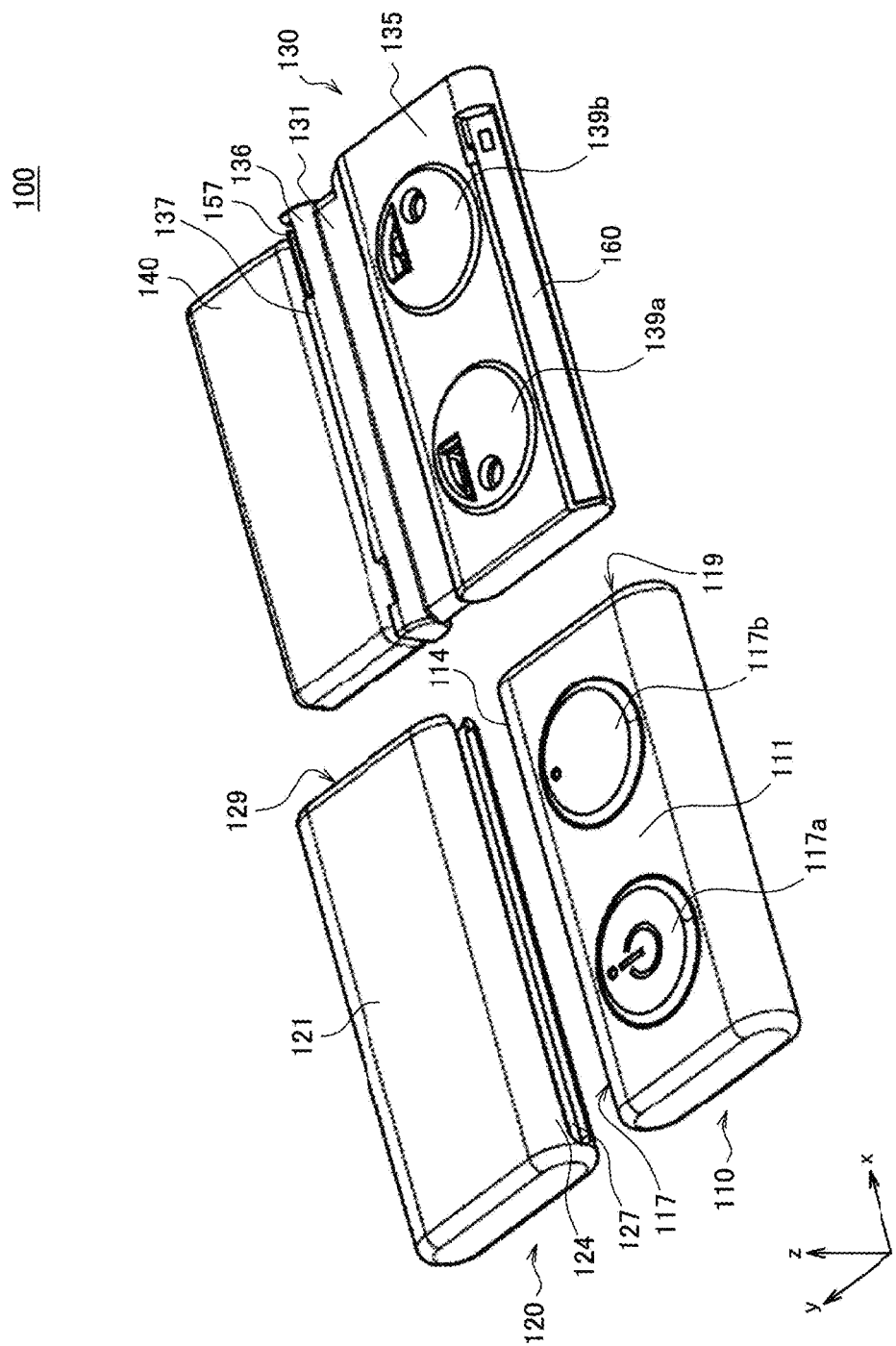
FIG. 7 is an exploded perspective view illustrating an example of an inner structure of the body sensor device according to the embodiment.
Figure 8:
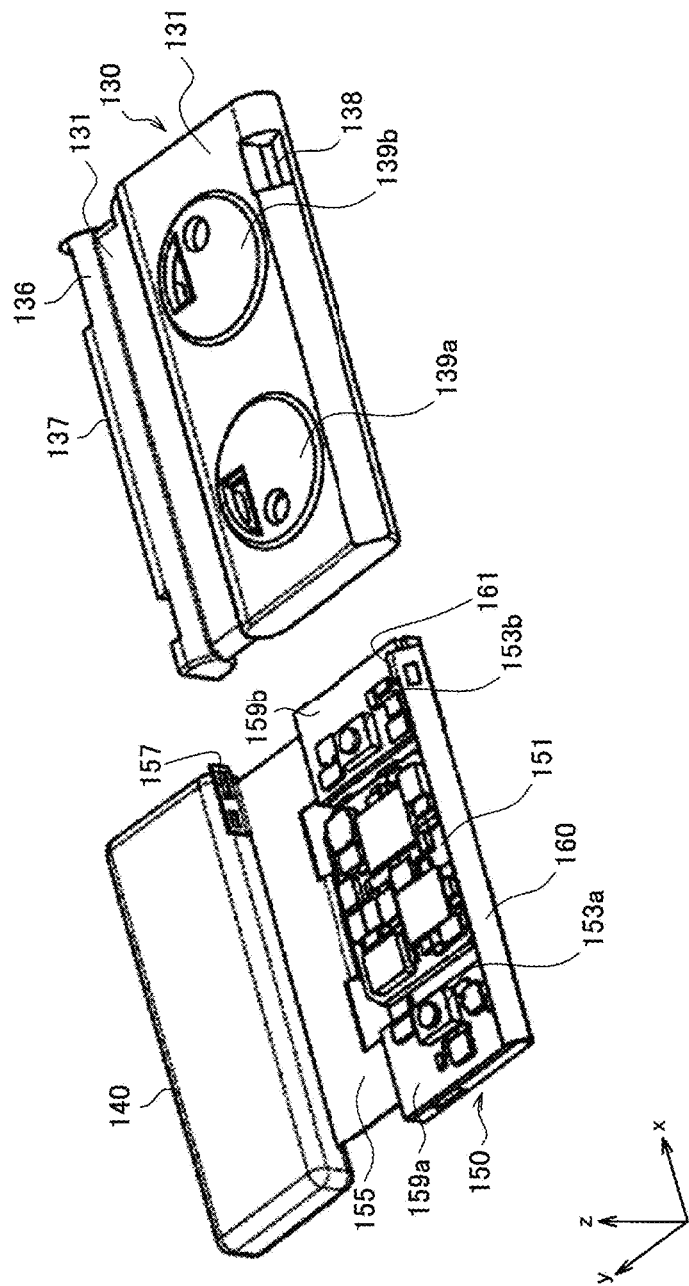
FIG. 8 is an exploded perspective view illustrating an example of an inner structure of the body sensor device according to the embodiment.

Here, a configuration of each of the casing 111 of the manipulation unit 110, the casing 121 of the battery unit 120, the manipulation unit body 130, the battery 140, and the substrate unit 150 will also be described in detail with reference to FIGS. 7 and 8. FIG. 7 is an exploded perspective view illustrating an example of an inner structure of the body sensor device according to the embodiment. FIG. 7 illustrates an example of the configuration of each of the casing 111, the casing 121, the manipulation unit body 130, and the battery 140. In addition, FIG. 8 is an exploded perspective view illustrating an example of an inner structure of the body sensor device according to the embodiment. FIG. 8 illustrates an example of a configuration of the substrate unit 150 contained in the manipulation unit body 130.

As illustrated in FIGS. 6 and 7, in the casing 121, an opening 129 is installed in one of the end surfaces extending in the transverse direction (that is, the end surfaces located in the longitudinal direction) in the outer circumferential end surface. In addition, in the casing 121, a notch 127 is installed to extend in the longitudinal direction along the end surface 124 so that the notch 127 continues from the opening 129 to the end surface 124 (that is, the end surface 124 described with reference to FIGS. 1 and 2) disposed to extend in the longitudinal direction and face the end surface 114 of the casing 111 among the outer circumferential end surfaces. That is, in the notch 127, an end portion on the side of the opening 129 of the end portions in the longitudinal direction is opened.

In addition, in the casing 111, an opening 119 is installed in one of the end surfaces extending in the transverse direction (that is, the end surfaces located in the longitudinal direction) in the outer circumferential end surface, like the casing 121. In addition, in the casing 111, a notch 117 is installed (that is, to extend in the longitudinal direction) along the end surface 114 so that the notch 117 continues from the opening 119 to the end surface 114 (that is, the end surface 114 described with reference to FIGS. 1 and 2) disposed to extend in the longitudinal direction and face the end surface 124 of the casing 121 among the outer circumferential end surfaces. That is, in the notch 117, an end portion on the side of the opening 119 of the end portions in the longitudinal direction is opened.

The protection unit 135 contains the substrate unit 150 and plays a role of protecting the substrate unit 150. The protection unit 135 is formed of, for example, a member with flexibility (that is, an elastic body) such as rubber or an elastomer, like the connection unit 131.

In addition, a portion equivalent to the protection unit 135 of the manipulation unit body 130 can be inserted into and detached from the casing 111 of the manipulation unit 110 and is inserted into the casing 111 to be accommodated inside the casing 111. Specifically, dimensions of the protection unit 135 in the longitudinal direction, the transverse direction, and the thickness direction are formed to be less than dimensions of the casing 111 in the longitudinal direction, the transverse direction, and the thickness direction. On the basis of this configuration, the protection unit 135 is inserted into the casing 111 from the opening 119 in the longitudinal direction (the −x direction), so that the protection unit 135 is accommodated inside the casing 111.

In addition, in a case in which the protection unit 135 is inserted into the casing 111, support members 139a and 139b are installed on the upper surface of the protection unit 135 at positions respectively corresponding to the input units 115a and 115b to be exposed in the thickness direction (the z direction) of the protection unit 135.

The support member 139a is supported to be movable in the thickness direction of the protection unit 135. In addition, as illustrated in FIG. 8, the support member 139a is supported to be located above the switching unit 153a and the rear surface side of the support member 139a comes into contact with a portion equivalent to a pressing button of the switch unit 153a. In addition, as illustrated in FIG. 7, the support member 139a supports the input unit 115a from the rear surface side in a state in which the protection unit 135 is inserted into the casing 111. That is, when the input unit 115a is pressed from the upper side to the lower side (that is, in the −z direction) in the state in which the protection unit 135 is inserted into the casing 111, the support member 139a is pushed downward by the input unit 115a. Thus, the portion equivalent to the pressing button of the switch unit 153a is pressed downward by the support member 139a, and thus the switch unit 153a is switched (for example, the switch unit 153a is switched between ON/OFF).

In a similar way, the support member 139b is supported to be movable in the thickness direction of the protection unit 135. In addition, as illustrated in FIG. 8, the support member 139b is supported to be located above the switching unit 153b and the rear surface side of the support member 139b comes into contact with a portion equivalent to a pressing button of the switch unit 153b. In addition, as illustrated in FIG. 7, the support member 139b supports the input unit 115b from the rear surface side in a state in which the protection unit 135 is inserted into the casing 111. That is, when the input unit 115b is pressed from the upper side to the lower side in the state in which the protection unit 135 is inserted into the casing 111, the support member 139b is pushed downward by the input unit 115b. Thus, the portion equivalent to the pressing button of the switch unit 153b is pressed downward by the support member 139b, and thus the switch unit 153b is switched.

In addition, as illustrated in FIGS. 6 and 7, the connection unit 131 (that is, the connection unit 131 described with reference to FIGS. 1 and 2) is formed on one of the end surfaces extending in the longitudinal direction in the outer circumferential end surface of the protection unit 135 to extend in the transverse direction (the y direction).

The connection unit 131 is formed so that the thickness in the z direction is thinner than the thickness of the protection unit 135 and is formed so that the thickness is thinner than the width of the notch 117 formed on the end surface 114 of the casing 111 in the z direction. Therefore, in a case in which the protection unit 135 is accommodated inside the casing 111, the connection unit 131 is exposed to the outside of the casing 111 to extend from the notch 117 in the transverse direction (the y direction). Note that the thickness of the protection unit 135 in the y direction at this time may be formed to be thicker than the width of the notch 117 in the z direction. It is possible to prevent occurrence of a situation in which the protection unit 135 is extracted outside of the casing 111 from the notch 117 in the transverse direction (the y direction) in a case in which the protection unit 135 is accommodated inside the casing 111 in this configuration.

In addition, as illustrated in FIG. 6, in the connection unit 131, the restriction member 133 may be installed to extend in the transverse direction (the y direction). As a specific example, the restriction member 133 with a wire shape and higher rigidity than the connection unit 131 like a metal, a resin, or the like may be embedded in the connection unit 131.

In addition, as illustrated in FIGS. 6 and 7, in the connection unit 131, the engagement unit 136 is installed in an end portion opposite to the protection unit 135. In addition, in the engagement unit 136, a mounting unit 137 for mounting the battery 140 may be installed in an end portion opposite to the connection unit 131 in the engagement unit 136. As a specific example, as illustrated in FIG. 7, an end side extending in the longitudinal direction in the outer circumferential end portion of the battery 140 is mounted in the engagement unit 136 via the mounting unit 137, and thus the battery 140 is supported by the engagement unit 136. Note that the configuration of the mounting unit 137 is not particularly limited as long as the battery 140 can be mounted on the engagement unit 136. For example, the mounting unit 137 may be fitted in a depression or a projection formed on the side of the battery 140.

In addition, as illustrated in FIG. 7, in the engagement unit 136, an electrode 157 is exposed at a part of a portion in which the battery 140 is mounted. That is, in a case in which the battery 140 is mounted on the engagement unit 136, the electrode 157 comes into contact with an output terminal that outputs power in the battery 140 to electrically connect the output terminal to the electrode 157.

In addition, the battery 140 can be inserted into and detached from the casing 121 of the battery unit 120, and thus is inserted into the casing 121 to be accommodated inside the casing 121. Specifically, the engagement unit 136 is formed so that the thickness in the z direction is thinner than the thickness of the casing 121. In addition, the battery 140 is formed so that dimensions in the longitudinal direction, the transverse direction, and the thickness direction are respectively less than the dimensions of the casing 121 in the longitudinal direction, the transverse direction, and the thickness direction. On the basis of this configuration, when the engagement unit 136 and the battery 140 are inserted into the casing 121 from the opening 129 in the longitudinal direction (the −x direction) in a state in which the battery 140 is mounted on the engagement unit 136, the engagement unit 136 and the battery 140 are accommodated inside the casing 121.

In addition, the connection unit 131 is formed to be thinner than the width of the notch 127 formed on the end surface 124 of the casing 121 in the z direction. Therefore, in a case in which the engagement unit 136 and the battery 140 are accommodated inside the casing 121, the connection unit 131 is exposed to the outside of the casing 121 to extend from the notch 127 in the transverse direction (the −y direction).

In addition, as illustrated in FIG. 7, an antenna unit 160 is installed on an end surface located opposite to the connection unit 131 in the outer circumferential end surface of the protection unit 135. The antenna unit 160 is equivalent to an antenna element used for the body sensor device 100 to communicate with another device via a wireless communication path. A part of the antenna unit 160 is electrically connected to the substrate unit 150 contained in the protection unit 135. Note that at least a part of the antenna unit 160 may be installed to be exposed to the outside of the protection unit 135. In addition, the antenna unit 160 may be accommodated inside the casing 111 along with the protection unit 135 when the protection unit 135 is accommodated in the casing 111. In this configuration, since the antenna unit 160 can be disposed so that the antenna element is separate from the battery 140, it is possible to reduce deterioration in a signal transmitted and received along with radio waves by the antenna unit 160.

On the basis of the above-described configuration, when the protection unit 135 is accommodated in the casing 111 and the engagement unit 136 and the battery 140 are accommodated in the casing 121 in the state in which the battery 140 is mounted on the engagement unit 136, the body sensor device 100 has the shape illustrated in FIG. 1.

Here, the configuration of the substrate unit 150 will be described in more detail with reference to FIG. 8. The substrate unit 150 includes a portion of the sensor substrate 151 in which various sensors are installed, a sub-substrate 159a in which the switch 135a is installed, a sub-substrate 159b in which the switch 135b is installed, and a wiring unit 155. The sensor substrate 151, the sub-substrate 159a, and the sub-substrate 159b are electrically connected to each other via the wiring unit 155.

At least a part of the wiring unit 155 is contained in the connection unit 131 and the electrode 157 to which the output terminal of the battery 140 is electrically connected is installed in an end portion opposite to a portion in which the sensor substrate 151, the sub-substrate 159a, and the sub-substrate 159b are connected to each other. That is, power is supplied from the battery 140 connected to the electrode 157 to each of the sensor substrate 151, the sub-substrate 159a, and the sub-substrate 159b via the wiring unit 155.

The wiring unit 155 is formed of, for example, a flexible wiring such as flexible printed circuits (FPC) (that is, the wiring unit 155 has flexibility and is deformable). In this configuration, for example, as illustrated in FIGS. 3 and 4, even in a case in which the body sensor device 100 is folded in the connection unit 131 and the connection unit 131 is deformed, an electric connection relation between the battery 140 connected to the electrode 157, the sensor substrate 151, and the sub-substrate 159a, and the sub-substrate 159b is maintained.

The switch unit 153a is equivalent to a switch for switching ON/OFF power of the body sensor device. That is, with switching of the switch unit 153a, for example, power is supplied from the battery 140 connected to the electrode 157 to each unit of the substrate unit 150 via the wiring unit 155.

In the antenna unit 160, a feeding point denoted by reference numeral 161 is electrically connected to the sub-substrate 159a. In addition, in the protection unit 135, an opening 138 is installed at a position corresponding to the feeding point 161. In this configuration, the antenna unit 160 is electrically connected to the substrate unit 150 (that is, the sub-substrate 159b) contained in the protection unit 135 via the feeding point 161 and at least a part of the antenna unit 160 is exposed to the outside of the protection unit 135 via the opening 138. In addition, a communication unit (of which detailed illustration is omitted) installed in the substrate unit 150 is electrically connected to the feeding point 161. The communication unit has, for example, a configuration for realizing communication with another device via a wireless communication path, like a so-called RF circuit, a bandpass filter, a mixer, or an oscillator (for example, a local oscillator). On the basis of this configuration, for example, the communication unit demodulates a received signal received by the antenna unit 160 or modulates transmission target data into a transmission signal to transmit the transmission signal to the antenna unit 160. Note that the switch unit 153b is equivalent to a switch for switching various operations of the communication unit.

As described above, various sensors (of which detailed illustration is omitted) are installed in the sensor substrate 151. As the various sensors, for example, sensors that detect a change in a position or a direction of the body sensor device 100 (furthermore, a change in a position or a direction of a part of the body on which the body sensor device 100 is worn), like an acceleration sensor or an angular velocity sensor, may be installed. In addition, as the various sensors, sensors that detect a shock applied to the body sensor device 100 (furthermore, a shock applied to a part of the body on which the body sensor device 100 is worn), like a shock sensor, may be installed. Various sensors installed in the sensor substrate 151 are driven, for example, on the basis of power supplied from the battery 140 connected to the electrode 157 via the wiring unit 155. In addition, the various sensors may output information indicating detection results to the above-described communication unit. Thus, for example, the detection results detected by the various sensors can also be transmitted to another connected device via a wireless communication path.

The example of the inner structure of the body sensor device according to the embodiment has been described above with reference to FIGS. 6 to 8.

<1.3. Holder>

Next, an example of a holder for wearing the body sensor device according to the embodiment on a predetermined part of the body will be described. For example, FIG. 9 is an explanatory diagram illustrating an example of a schematic configuration of the holder of the body sensor device according to the embodiment.

Figure 9:
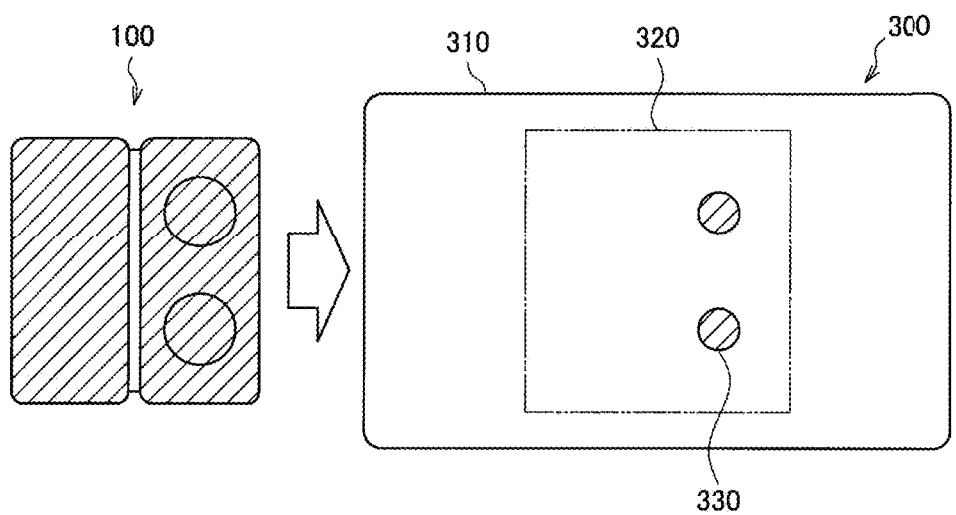
FIG. 9 is an explanatory diagram illustrating an example of a schematic configuration of a holder of the body sensor device according to the embodiment.

As illustrated in FIG. 9, a holder 300 includes a belt unit 310 and a pocket unit 320.

The belt unit 310 has a belt-like shape and one surface of the belt unit 310 is wound to come into contact with a predetermined part of the body (for example, an arm, the thorax, or the pelvis) of the body to be held on the part of the body. In addition, for example, the belt unit 310 may also be wound around a predetermined part of the body by mutually engaged claws, a Magic Tape (registered trademark), or the like to be held.

In addition, the pocket unit 320 that accommodates the above-described body sensor device 100 in a part of a surface opposite to a surface coming into contact with a part of the body on which the holder 300 is worn, that is, a part of a surface facing the outside in a case in which the holder 300 is mounted, is installed in the belt unit 310. That is, when the body sensor device 100 is accommodated in the pocket unit 320 of the holder 300 in a state in which the holder 300 is worn on a predetermined part of the body, the lower surface of each of the casings 111 and 121 of the body sensor device 100 is worn to come into contact with the part of the body via the belt unit 310. Note that a surface of a side on which the pocket unit 320 is installed among the surfaces of the belt unit 310 is also referred to as a "front surface" and a surface coming into contact with a part of the body is also referred to as a "rear surface" in the following description.

In the pocket unit 320, through holes 330 are formed at positions corresponding to the input unit 115 (for example, the input units 115a and 115b illustrated in FIG. 1) of the body sensor device 100 in a case in which the body sensor device 100 is accommodated inside. That is, in a case in which the body sensor device 100 is accommodated in the pocket unit 320, the input unit 115 of the body sensor device 100 is exposed via the through holes 330. In this configuration, even in a state in which the body sensor device 100 is accommodated in the pocket unit 320, the user can manipulate the input unit 115 exposed via the through holes 330.

Note that movements of a plurality of parts of the body can also be sensed by using the plurality of body sensor devices 100 according to the embodiment. As a specific example, in a case in which movements of the arm, the thorax, and the pelvis are sensed, the body sensor devices 100 associated with these parts in advance are worn on the parts of the arm, the thorax, and the pelvis. In view of such a situation, for example, casings with mutually different colors may also be applied as the casings 111 and 121 to the plurality of body sensor devices 100 associated with the mutually different parts of the body. In addition, in this case, at least a part of the holder 300 may be indicated with the same color as the casings of the body sensor device 100 associated with the part of the body on which the holder 300 is worn. As a more specific example, in a case in which the color of the casings of the body sensor device 100 associated with the pelvis (that is, the body sensor device 100 sensing a movement of the pelvis) is red, at least a part of the holder 300 worn on the pelvis may be indicated by red.

For example, in the example illustrated in FIG. 9, for the holder 300, the positions facing at least the through holes 330 are indicated with the same color as the casings of the body sensor device 100 (that is, the body sensor device 100 associated with the part of the body on which the holder 300 is worn) accommodated in the pocket unit 320 inside of the pocket unit 320. In this configuration, in a state in which the body sensor device 100 is not accommodated in the pocket unit 320, portions with the same color as the body sensor device 100 accommodated in the pocket unit 320 are exposed from the through holes 330. Thus, with the color of the portions exposed from the through holes 330, a user can recognize which body sensor device 100 may be accommodated in the pocket unit 320 of the holder 300.

The example of the holder for wearing the body sensor device according to the embodiment on a predetermined part of the body has been described above with reference to FIG. 9.

<1.4. Example of Application>

Figure 10:
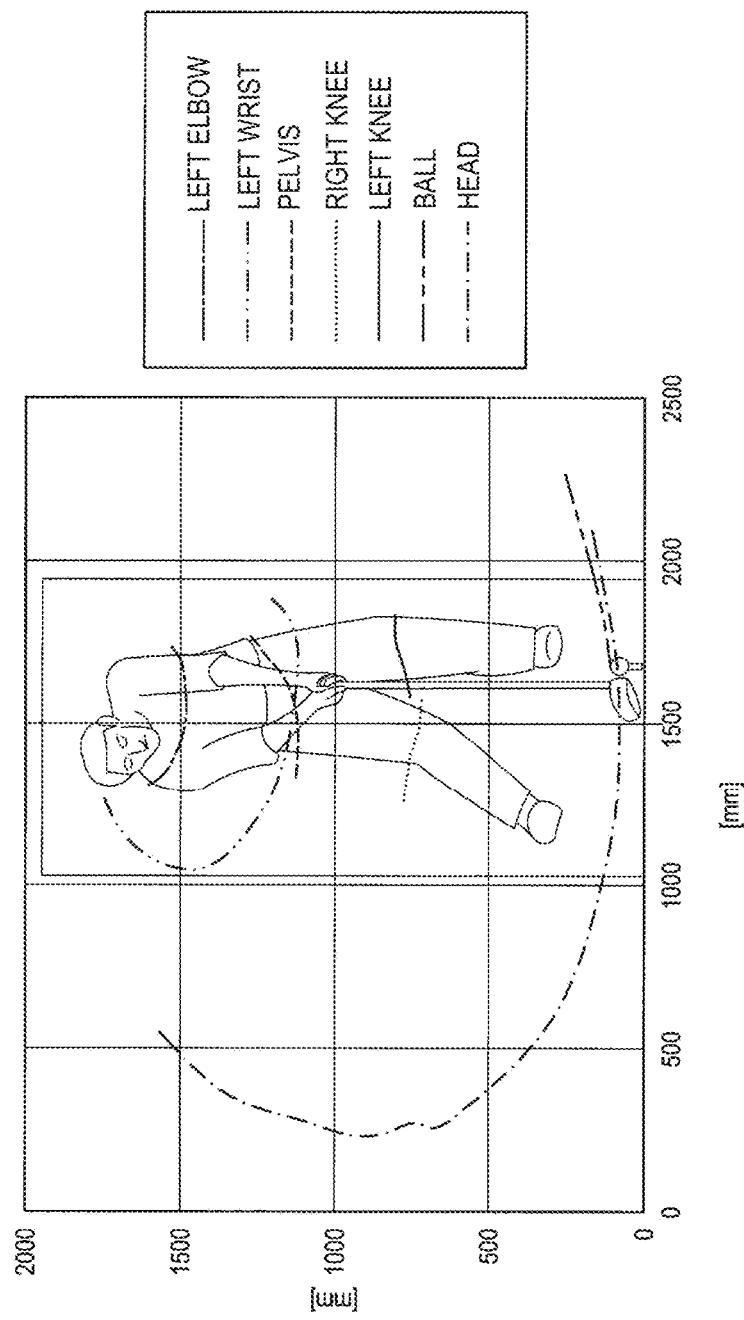
FIG. 10 is an explanatory diagram illustrating an example of an application in which the body sensor device according to the embodiment is used.

Next, an example of an application in which the body sensor device 100 according to the embodiment is used will be described with reference to FIG. 10. FIG. 10 is an explanatory diagram illustrating an example of an application in which the body sensor device 100 according to the embodiment is used.

As described above, the body sensor device 100 according to the embodiment senses a movement of a predetermined part of the body (for example, a change in a position or a direction of the part) when the lower surface of the casing is worn to come into contact with the part of the body. In addition, by using the plurality of body sensor devices 100, it is also possible to sense movements of a plurality of parts of the body. Therefore, for example, by sensing and visualizing a movement of each part of the body at the time of a golf or tennis swing by the body sensor device 100 according to the embodiment, it is also possible to confirm a swing form.

For example, FIG. 10 illustrates an example of a case in which a movement of each part of the body at the time of a golf swing is sensed and the movement of the part of the body (that is, a change in a position or a direction of the part of the body) is visualized as an image on the basis of a sensing result. Specifically, in the example illustrated in FIG. 10, trajectories of movements of parts of a left elbow, a left wrist, a pelvis, a right knee, and a left knee, are visualized on the basis of sensing results detected by the body sensor devices 100 worn on these parts of the body. In addition, a movement of the head of a club can also be estimated (simulated) on the basis of the sensing results of the movements of the parts of the body, and thus a trajectory of a ball can also be estimated (simulated) from an estimation result of the movement of the head. In addition, according to another embodiment, a movement of a club can also be sensed directly and visualized by using a shaft sensor device to be separately described below.

Note that an application to be described with reference to FIG. 10 may be installed in, for example, an information processing device capable of communicating with each body sensor device 100 via a wireless communication path, like a so-called smartphone, a table terminal, or the like. Thus, for example, the information processing device can visualize a movement of each part of the body as a video on the basis of a sensing result collected from each body sensor device 100 and present the video to a user via an output unit such as a display or the like.

Note that the above-described example is merely an example and a mode of the application in which the body sensor device 100 is used is not necessarily limited to the above-described example as long as various kinds of information can be presented using sensing results of the parts of the body by the body sensor devices 100 according to the embodiment. Note that an example of a user interface (UI) for presenting various kinds of information are presented to a user by using sensing results by the body sensor devices 100 according to the embodiment will be separately described below according to another embodiment.

The example of the application in which the body sensor devices 100 according to the embodiment is used has been described above with reference to FIG. 10.

<1.5. Evaluation>

As described above, the body sensor device 100 according to the embodiment includes the manipulation unit 110 that includes the substantially plate-shaped casing 111, the battery unit 120 that includes the substantially plate-shaped casing 121, and the connection unit 131 that connects the manipulation unit 110 to the battery unit 120. A detection unit such as any of various sensors, a communication unit that communicates with another device via a wireless communication path, and the like are installed in the manipulation unit 110. In addition, the battery 140 is held inside the battery unit 120. In addition, the connection unit 131 connects the end surface 114 to the end surface 124 so that the connection unit 131 bridges a gap between the end surface 114 extending in the longitudinal direction in the outer circumferential end surface of the casing 111 and the end surface 124 extending in the longitudinal direction among the outer circumferential end surface of the casing 111. In addition, at this time, the connection unit 131 connects the manipulation unit 110 to the battery unit 120 so that the surface direction of the lower surface 113 of the casing 111 substantially matches the surface direction of the lower surface 123 of the casing 121. In addition, the connection unit 131 is formed of a material (for example, an elastic body) with flexibility such as rubber or an elastomer, and thus is foldable. On this configuration, the body sensor device 100 is worn on a predetermined part of the body so that the lower surface 113 of the casing 111 and the lower surface 123 of the casing 121 come into contact to a part of the body.

In particular, in the body sensor device 100 according to the embodiment, supply of power to various sensors or the communication unit is performed by the battery, and thus the device can independently operate. In addition, the body sensor device 100 can communicate with another device (for example, a smartphone) via a wireless communication path, and thus transmits, for example, information indicating sensing results by various sensors to another device via the communication path. In this configuration, for example, the body sensor device 100 can prevent occurrence of a situation in which a movement of the body is inhibited because of wearing of the device compared to a case in which power is supplied from an external device connected in a wired manner. In addition, since the body sensor device 100 can independently operate, there is no restriction on a position at which the device is worn due to a wiring or the like compared to a configuration in which power is supplied in a wired manner. Therefore, the degree of freedom of the wearing position is higher and movements of various parts of the body can be sensed.

On the other hand, in a case in which a battery is contained like the body sensor device 100 according to the embodiment, an area or a volume occupied by a portion worn on a part of the body (that is, a portion in which the sensor or the like is contained) tends to further increase in proportion to the battery, compared to a case in which no battery is contained (for example, a configuration in which power is supplied from the outside in a wired manner). More specifically, in a case in which the battery and the sensor substrate in which the sensor and the like are installed are installed and piled up, the height of the device increases. Thus, in a case in which the body sensor device is worn on a part of the body, the sense of discomfort felt by the user further increases. However, for example, in a case in which the sensor substrate and the battery are arranged in the horizontal direction, the thickness of the device can be formed to be thin. However, the occupied area increases. For example, as described with reference to the left drawing of FIG. 3, the degree of close contact to a part of the body deteriorates in some cases.

In contrast, in the body sensor device 100 according to the embodiment, the connection unit 131 is formed of a material with flexibility such as rubber or an elastomer, and thus can be folded between the casing 111 of the manipulation unit 110 and the casing 121 of the battery unit 120. In this configuration, the body sensor device 100 according to the embodiment is formed to be thinner than the thickness of the body sensor device 100 and the degree of close contact to a part of the body can be further improved. In addition, as described with reference to FIG. 4, the body sensor device 100 can also operate in a direction in which the casing 111 can be twisted relatively with respect to the casing 111. Therefore, the body sensor device 100 can be worn in closer contact with a variety of curved surfaces, that is, can be worn in closer contact with a variety of parts of the body. Thus, in the body sensor device 100 according to the embodiment, for example, looseness of the body sensor device 100 can be suppressed. Therefore, it is also possible to prevent deterioration in precision of sensing accompanied due to the looseness.

In addition, as described with reference to FIG. 2, the body sensor device 100 according to the embodiment has a substantially square shape of which four sides are 36 mm when viewed from the upper surface side and can be formed with a thickness of about 5.75 mm in a thickest portion. In this way, the body sensor device 100 can be formed in a relatively small and thin form. Therefore, even in a case in which the body sensor device 100 is worn on a part of the body, the user can move the part of the body without the sense of discomfort. In addition, by forming the body sensor device 100 in a relatively small and thin form, it is also possible to further improve the degree of freedom of a wearing position.

In addition, the body sensor device 100 according to the embodiment can be worn on any of various parts of the body, and thus can directly sense a movement of the part of the body. In addition, by using the plurality of body sensor devices 100, it is possible to individually sense movements of a plurality of parts of the body. By integrating sensing results of the body sensor devices 100, it is also possible to analyze a movement of the body (for example, a swing form). Therefore, the body sensor device 100 according to the embodiment can sense a motion of the body more accurately than in a case in which a movement of the body is sensed indirectly, for example, on the basis of a sensing result by worn on an instrument such as a sensor a golf club or a racket.

In addition, the body sensor device 100 according to the embodiment can transmit a sensing result of a movement of a part of the body on which the device is worn to the communication terminal such as a so-called smartphone or a tablet terminal via a wireless communication path. Further, by installing a predetermined application in the communication terminal, it is also possible to realize a function of presenting various kinds of information on the basis of a sensing result by the body sensor device 100. In this way, according to the body sensor device 100 according to the embodiment, a system in which a movement of the body (for example, a swing) is sensed to carry out various kinds of analysis can be realized at lower cost with a simpler configuration without involving a large-scale device.

2. Second Embodiment: Shaft Sensor Device

<2.1. Exterior Example of Shaft Sensor Device>

Next, a shaft sensor device will be described according to a second embodiment of the present disclosure. First, an example of a schematic configuration of the shaft sensor device according to the embodiment will be described. A shaft sensor device 200 according to the embodiment includes various sensors such as an acceleration sensor or an angular velocity sensor inside a casing and is mounted on a member with a pillar shape like the shaft of a golf club or the like to sense a movement of the member (for example, a movement of the shaft).

Figure 11:
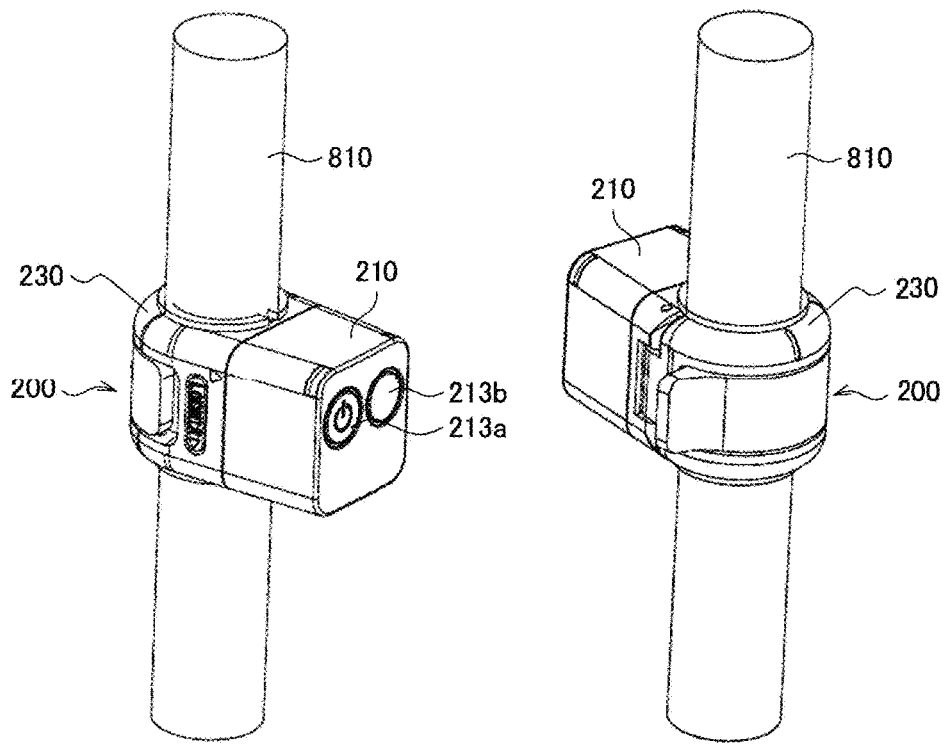
FIG. 11 is a perspective view illustrating an example of a structure of a shaft sensor device according to a second embodiment of the present disclosure.

For example, FIG. 11 is a perspective view illustrating an example of a structure of the shaft sensor device 200 according to a second embodiment.

As illustrated in FIG. 11, the shaft sensor device 200 according to the embodiment includes a body unit 210 and a mounting unit 230. The body unit 210 and the mounting unit 230 can be attached and detached. Note that the details of an example of a configuration in which the body unit 210 and the mounting unit 230 are attached and detached will be separately described below.

Various sensors (for example, an acceleration sensor, an angular velocity sensor, and a shock sensor), a communication unit communicating with another device via a wireless communication path on the basis of a communication standard such as Blutooth, and the like are installed inside the body unit 210. In addition, the body unit 210 contains a battery. The device can independently operate by causing the battery to supply power to the various sensors and the communication unit. In addition, the input unit 213 such as a button for manipulating the shaft sensor device 200 is installed in a part of the casing of the body unit 210. For example, in the example illustrated in FIG. 11, an input unit 213a for manipulating ON/OFF of power and an input unit 213b for manipulating the communication unit (for example, a manipulation such as turning ON/OFF or pairing the communication unit) are installed as the input unit 213.

The mounting unit 230 has a configuration in which the body unit 210 is mounted on a pillar member 810. As illustrated in FIG. 11, the mounting unit 230 is held in a part of the pillar member 810 by gripping the side surface of the pillar member 810. In this way, when the body unit 210 is mounted on the mounting unit 230 in a state in which the mounting unit 230 is held in the part of the pillar member 810, the body unit 210 is held in the part of the pillar member 810 via the mounting unit 230. In this configuration, the shaft sensor device 200 is mounted on the pillar member 810.

When the shaft sensor device 200 is mounted on the pillar member 810, as described above, as illustrated in FIG. 11, various sensors installed inside the shaft sensor device 200 can sense a movement (for example, a change in a position or a direction) of the member 810. In addition, when shock sensors are installed as various sensors, the shaft sensor device 200 can also detect, for example, a shock applied to the pillar member 810. Thus, for example, when the shaft sensor device 200 is mounted on the shaft of a golf club, the shaft sensor device 200 can also detect a timing at which a ball is hit by the head of the golf club (that is, an impact timing).

The example of the schematic configuration of the shaft sensor device according to the embodiment has been described above with reference to FIG. 11.

<2.2. Configurations of Body Unit and Mounting Unit>

Figure 12:
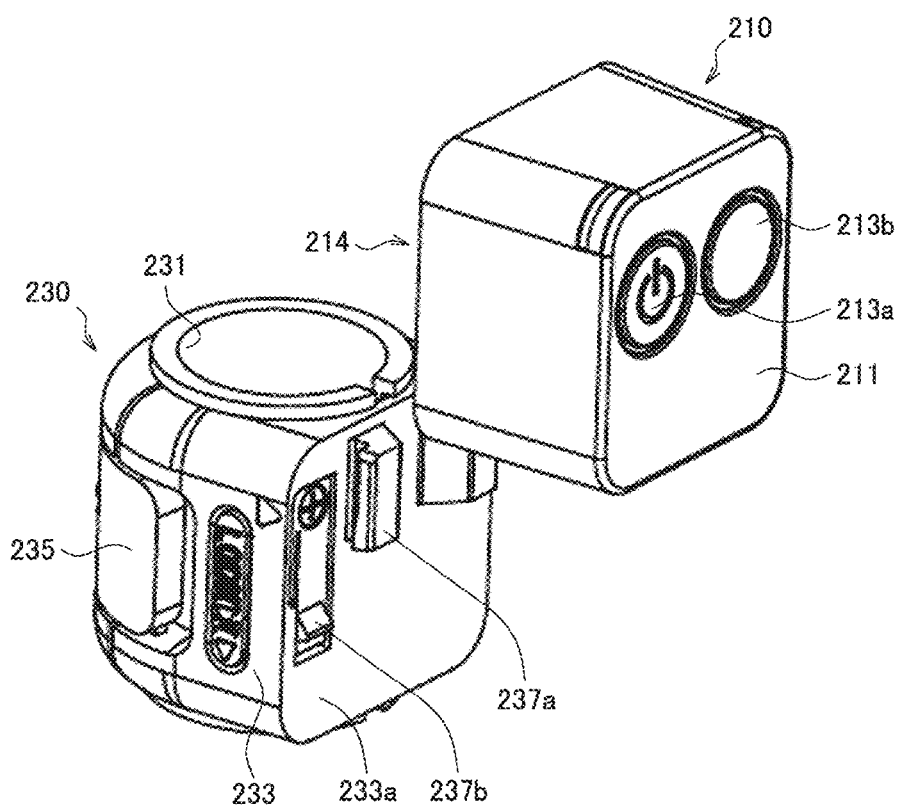
FIG. 12 is an explanatory diagram illustrating examples of configurations of a body unit and a mounting unit of a shaft sensor device according to the embodiment.
Figure 13:
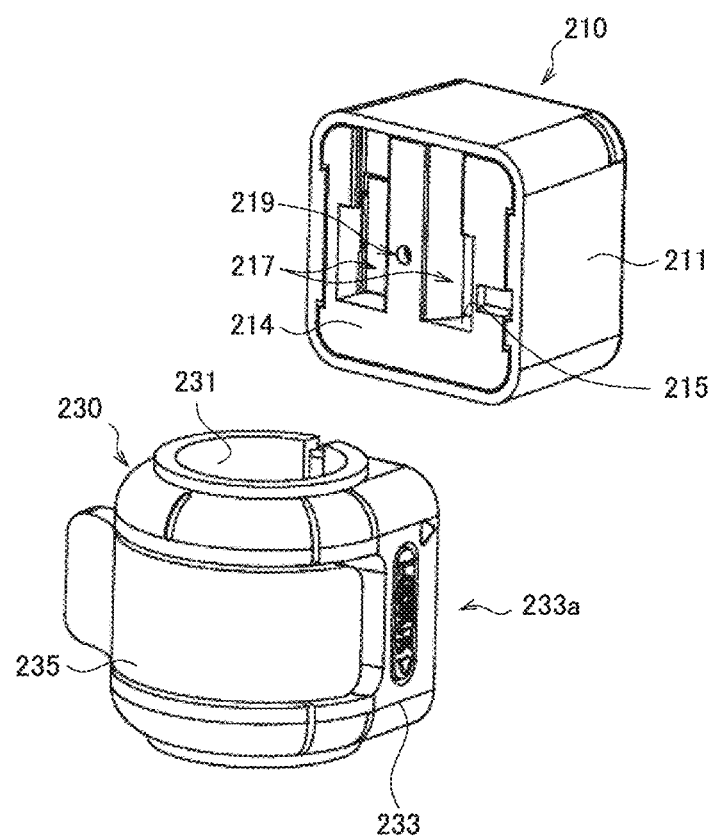
FIG. 13 is an explanatory diagram illustrating examples of configurations of a body unit and a mounting unit of a shaft sensor device according to the embodiment.

Next, examples of configurations of the body unit 210 and the mounting unit 230 of the shaft sensor device 200 according to the embodiment will be described in more detail. For example, FIGS. 12 and 13 are explanatory diagrams illustrating examples of configurations of the body unit 210 and the mounting unit 230 of the shaft sensor device 200 according to the embodiment. FIGS. 12 and 13 illustrate a state in which the body unit 210 is detached from the mounting unit 230.

For example, FIG. 12 is a perspective view in a case in which the body unit 210 and the mounting unit 230 are viewed from the side of the body unit 210 in a state in which the body unit 210 is detached from the mounting unit 230. Note that a surface of a side on which the input unit 213 is installed in the casing 211 of the body unit 210 is also referred to as a "front surface" and a surface opposite to the front surface is also referred to as a "rear surface" in the following description. That is, in the example illustrated in FIGS. 11 to 13, the body unit 210 is mounted on the mounting unit 230 so that a rear surface side of the casing 211 denoted by reference numeral 214 comes into contact with a part of the mounting unit 230.

As illustrated in FIG. 12, the mounting unit 230 includes a gripping member 231, a casing 233, and a lock mechanism 235.

The gripping member 231 is a hollow and substantially cylindrical member and a notch is formed in a part of a side surface in an axial direction. The gripping member 231 is formed of, for example, a metal or a resin. When the outer surface is pressed in a state in which the pillar member is inserted inside, the gripping member 231 is deformed so that the outer circumference is further shortened by a maximum of the width of the notch (that is, the inner diameter is further decreased), and thus the inner surface comes into contact with the outer surface of the pillar member with the deformation. That is, the outer surface of the pillar member is gripped by the inner surface of the gripping member 231.

In a state in which at least a part of the casing 233 engages with a part of the gripping member 231 and the part comes into contact with the outer surface of the gripping member 231, the outer surface of the gripping member 231 is gripped along with the lock mechanism 235 to be described below, so that the gripping member 231 is held in the part. That is, the lock mechanism 235 has a configuration for holding the gripping member 231 in the part of the casing 233 along with the casing 233. On the basis of this configuration, the gripping member 231 gripping the outer surface of the pillar member is held in the part of the casing 233, and thus the casing 233 is relatively held in the part of the pillar member. Note that an example of a detailed configuration in which the casing 233 and the lock mechanism 235 hold the gripping member 231 will be separately described below.

In addition, a configuration for mounting the body unit 210 on the mounting unit 230 is installed in a part of the casing 233. For example, in the example illustrated in FIG. 12, in a case in which the mounting unit 230 in the casing 233 is mounted on the pillar member, a mounting portion 237 for mounting the body unit 210 on the mounting unit 230 (that is, the casing 233) is installed at a position equivalent to a part of the outer circumferential surface located opposite to the member. For example, in the example illustrated in FIG. 11, fitting portions 237a and 237b fitted in parts (that is, a rear surface denoted by reference numeral 214) of the casing 211 of the body unit 210 are installed as the mounting portion 237 on an end surface denoted by reference numeral 233a in the casing 233. As a more specific example, in the example illustrated in FIG. 11, the fitting portions 237a and 237b are formed as projecting members. The fitting portions 237a and 237b are fitted in depressions formed on the side of the body unit 210, so that the body unit 210 is mounted on the mounting unit 230. Note that a lock mechanism for maintaining a state in which the body unit 210 is mounted on the mounting unit 230 is installed in the mounting portion 237.

Next, in particular, a configuration of the casing 211 on the side of the rear surface 213 in the configuration of the body unit 210 will be described mainly with reference to FIG. 13. FIG. 13 is a perspective view in a case in which the body unit 210 and the mounting unit 230 are viewed from the side of the rear surface 214 of the casing 211 of the body unit 210 in a state in which the body unit 210 is detached from the mounting unit 230.

As illustrated in FIG. 13, a mounting portion 215 for mounting the body unit 210 on the mounting unit 230 is installed on the side of the rear surface 214 of the casing 211. Specifically, in the example illustrated in FIG. 13, the mounting portion 215 is formed as a depression fitted in the fitting portions 237a and 237b with a projection shape described with reference to FIG. 12. In addition, a charging terminal 217 for charging a battery contained in the body unit 210 with power is installed inside (for example, an inner surface or a bottom surface) the mounting portion 215 formed as a depression. That is, the mounting portion 215 plays a role of mounting a charger on the body unit 210. In a case in which the body unit 210 is mounted on the charger, the charging terminal 217 installed on the side of the body unit 210 is electrically connected to a feeding terminal of the charger side.

In addition, a reset switch 219 for resetting various kinds of settings is installed on the side of the rear surface 214 of the casing 211. Specifically, in the example illustrated in FIG. 13, a hole is installed in a part of the rear surface 214 of the casing 211 and the reset switch 219 is installed inside the hole. In this configuration, even in a case in which the body unit 210 is mounted on the mounting unit 230, it is possible to prevent occurrence of a situation in which the reset switch 219 is manipulated by a part of the side of the mounting unit 230.

Figure 14:
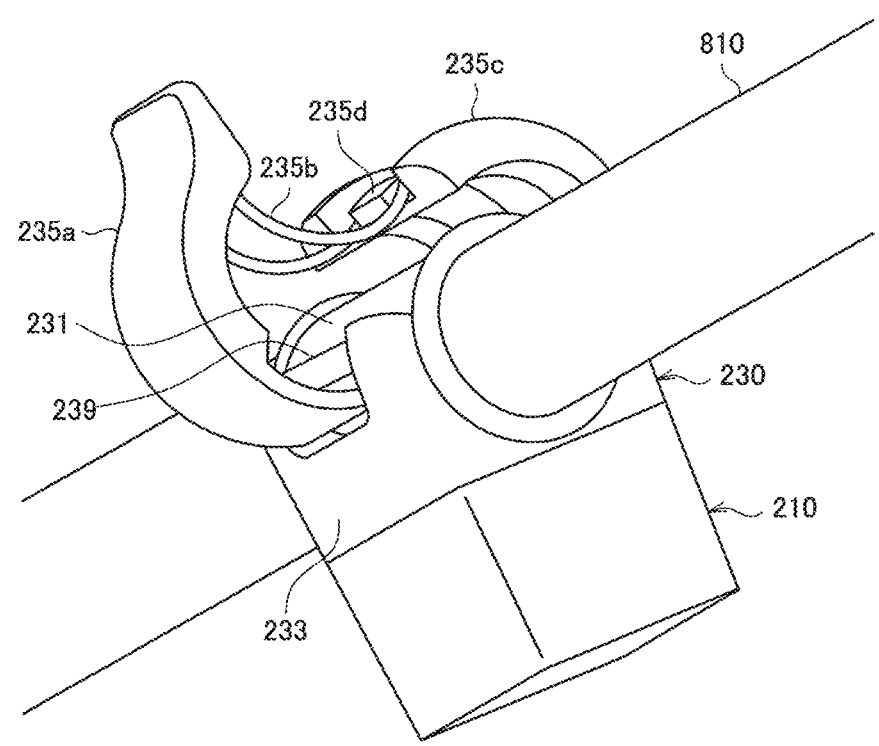
FIG. 14 is a perspective view illustrating an example of a configuration of the shaft sensor device according to the embodiment.

Next, an example of a configuration of the lock mechanism 235 of the mounting unit 230 in the shaft sensor device 200 according to the embodiment will be described with reference to FIG. 14. FIG. 14 is a perspective view illustrating an example of a configuration of the shaft sensor device 200 according to the embodiment. FIG. 14 illustrates an example of a configuration of the lock mechanism 235.

As illustrated in FIG. 14, the casing 233 includes a support portion 239 in which a depression is formed so that at least a part of the outer surface of the gripping member 231 comes into contact with the depression on the opposite side to a surface 233a on which the mounting portion 237 is installed.

In addition, the lock mechanism 235 is formed as, for example, a so-called three-fold buckle. That is, the lock mechanism 235 tightens the outer surface of the gripping member 231 along with the support portion 239 in the folded state and grips the outer surface of the pillar member 810 by the gripping member 231, so that the member 810 is supported. Thus, the shaft sensor device 200 is held by a part of the pillar member 810.

Here, the more detailed configuration of the lock mechanism 235 will be described. As illustrated in FIG. 14, the lock mechanism 235 includes a cover member 235a, a middle plate 235b, and a lower plate 235c. Each of the cover member 235a, the middle plate 235b, and the lower plate 235c is a long member and is curved in the longitudinal direction. In particular, the lower plate 235c continues from the position at which the support portion 239 is installed and is curved along the outer surface of the gripping member 231 in a state in which the lock mechanism 235 is folded (a three-folded state).

One end portion of the cover member 235a in the longitudinal direction is mounted to be rotatable with respect to one end side of the support portion 239 in a circumferential direction of the inner surface of a depression formed in the support portion 239. Similarly, the one end portion of the lower plate 235c in the longitudinal direction is mounted to be rotatable with respect to the other end side of the support portion 239 in the circumferential direction.

One end portion of the middle plate 235b in the longitudinal direction is mounted near an end portion opposite to the end portion in which the support portion 239 is mounted in the end portion of the cover member 235a in the longitudinal direction to be rotatable with respect to the cover member 235a. In addition, the other end portion of the middle plate 235b in the longitudinal direction is mounted in the end portion opposite to the end portion in which the support portion 239 is mounted in the end portion of the lower plate 235c in the longitudinal direction to be rotatable with respect to the lower plate 235c.

The lower plate 235c has a frame-shaped portion in which a notch 237d penetrating through the front and rear surfaces in the longitudinal direction is formed.

The middle plate 235b is formed to have a width narrower than the notch 237d of the lower plate 235c. In this configuration, the middle plate 235b is inserted into the notch 237d in the three-folded state so that the middle plate 235b and the lower plate 235c are substantially flush with each other.

The cover member 235a is disposed to overlap on the outer surfaces of the lower plate 235c and the middle plate 235b in a state in which the lock mechanism 235 is folded (a three-folded state).

When the lock mechanism 235 is folded in the above-described configuration, the inner surfaces of the lower plate 235c and the middle plate 235b come into contact with the outer surface of the gripping member 231 supported by the support portion 239. Then, the outer surface of the gripping member 231 is pressed by the lower plate 235c and the middle plate 235b, and the gripping member 231, and thus the gripping member 231 is deformed so that the outer circumference is further shortened (that is, the inner diameter is further decreased) by a maximum of the width of the notch formed on the outer surface. Thus, the inner surface of the gripping member 231 comes into contact with the outer surface of the pillar member 831, and thus the mounting unit 230 (furthermore, the shaft sensor device 200) is held in a part of the pillar member 831 by a frictional force generated by the inner surface of the gripping member 231 and the outer surface of the member 831.

Note that the configuration of the above-described lock mechanism 235 is merely an example. When the mounting unit 230 (furthermore, the shaft sensor device 200) can be held in the part of the pillar member like the shaft or the like of a golf club, the configuration of the lock mechanism 235 is not necessarily limited to the example illustrated in FIG. 14.

The examples of the configurations of the body unit 210 and the mounting unit 230 of the shaft sensor device 200 according to the embodiment have been described above in more detail with reference to FIGS. 11 to 14.

<2.3. Evaluation>

As described above, the shaft sensor device 200 according to the embodiment includes the mounting unit 230 that is held in the member by gripping the side surface of the pillar member like a shaft of golf or the like and the body unit 210 that can be attached to and detached from the mounting unit 230. Various sensors, a communication unit communicating with another device via a wireless communication path, and the like are installed inside the body unit 210. In addition, the mounting portion 215 with the depression shape fitted in the mounting portion 237 with the projection shape installed on the side of the mounting unit 230 is installed on the end surface (the rear surface 214) mounted on the mounting unit 230 in the casing 211 of the body unit 210. In addition, the charging terminal 217 for charging the battery contained in the body unit 210 with power is installed inside the mounting portion 215 formed as a depression. In addition, the reset switch 219 for resetting various kinds of settings may be installed on the side of the rear surface 214 of the casing 211 of the body unit 210.

In a case in which the body unit 210 is mounted on the mounting unit 230 in the above-described configuration, the shaft sensor device 200 according to the embodiment is in a state in which the charging terminal 217 or the reset switch 219 is shielded by the mounting unit 230 and is not exposed to the outside. In this configuration, the shaft sensor device 200 according to the embodiment can prevent, for example, occurrence of a situation in which the charging terminal 217 is short-circuited during sensing of a movement of an instrument such as a golf club or a situation in which the reset switch 219 is manipulated carelessly.

In addition, in the shaft sensor device 200 according to the embodiment, power is supplied to the various sensors or the communication unit by the battery so that the device can independently operate, like the body sensor device 100 according to the first embodiment. In addition, the shaft sensor device 200 can communicate with another device (for example, a smartphone) via a wireless communication path. For example, information indicating sensing results by the various sensors is transmitted to the other device via the communication path. In this configuration, the shaft sensor device 200 can prevent occurrence of a situation in which, for example, a movement of a member (for example, a shaft or the like of a golf club) on which the device is mounted or a movement of the body of a user holding the member is inhibited, compared to, for example, a case in which power is supplied from an external device connected in a wired manner.

In addition, as described above, the shaft sensor device 200 according to the embodiment can transmit a sensing result of a movement of a part of the body on which the device is worn to the communication terminal such as a so-called smartphone or a tablet terminal via a wireless communication path. Further, by installing a predetermined application in the communication terminal, it is also possible to realize a function of presenting various kinds of information on the basis of a sensing result by the shaft sensor device 200. In this way, according to the shaft sensor device 200 according to the embodiment, a system in which a movement of the body (for example, a swing) is sensed to carry out various kinds of analysis can be realized at lower cost with a simpler configuration without involving a large-scale device.

In addition, by using a sensing result by each of the shaft sensor device 200 according to the embodiment and the body sensor device 100 according to the above-described first embodiment, it is also possible to analyze a movement of the body of the user in more detail. Note that an example of a user interface (UI) for presenting various kinds of information to the user by using a sensing result by the shaft sensor device 200 according to the embodiment will be separately described below according to another embodiment.

3. Third Embodiment: Information Processing System

Next, an example of a system that analyzes a movement of a body on the basis of a sensing result by the body sensor device 100, the shaft sensor device 200, or the like according to the above-described embodiments and an example of a UI for presenting the analysis result to a user will be described according to a third embodiment of the present disclosure. In this description, note that an example of a case in which various kinds of information are presented by causing the body sensor device 100 or the shaft sensor device 200 to sense a movement of the body of a user or a golf club at the time of a s golf wing and performing various kinds of analysis or simulations on the basis of a sensing result will be described.

<3.1. System Configuration>

Figure 15:
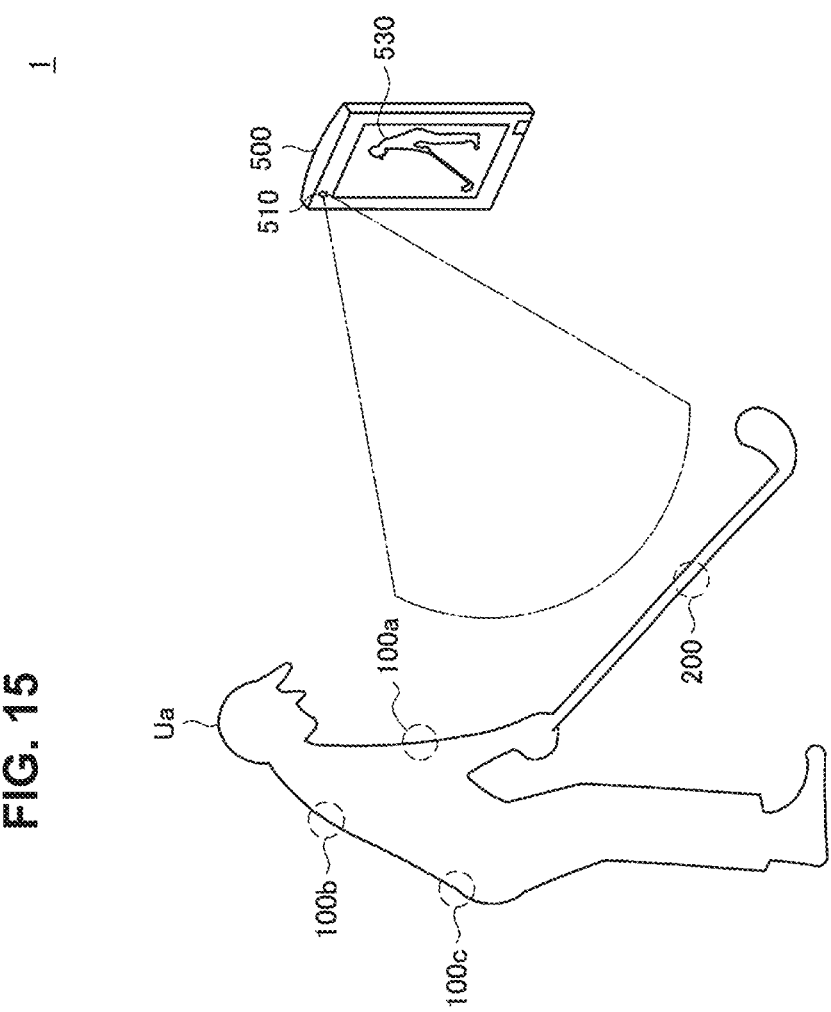
FIG. 15 is an explanatory diagram illustrating an example of a system configuration of an information processing system according to a third embodiment of the present disclosure.

First, an example of a system configuration of an information processing system 1 according to the embodiment will be described with reference to FIG. 15. FIG. 15 is an explanatory diagram illustrating an example of a system configuration of the information processing system 1 according to the embodiment. As illustrated in FIG. 15, the information processing system 1 according to the embodiment includes body sensor devices 100a to 100c, the shaft sensor device 200, and a terminal device 500. Each of the body sensor devices 100a to 100c and the shaft sensor device 200 are connected to the terminal device 500 via wireless communication paths.

The body sensor devices 100a to 100c are worn on mutually different parts among various parts of the body of a user Ua and sense motions of the parts of the body. For example, in the example illustrated in FIG. 15, the body sensor device 100a is worn on an arm (an arm opposite to a dominant arm) of a user Ua. In addition, the body sensor device 100b is worn on the thorax of the user Ua. In addition, the body sensor device 100c is worn on the pelvis of the user Ua. In addition, the shaft sensor device 200 is mounted on a golf club held by the user Ua.

On the basis of the above-described configuration, the body sensor devices 100a to 100c sense movements of the parts of the body on which the devices are worn and transmit information indicating sensing results to the terminal device 500 via wireless communication paths. Similarly, the shaft sensor device 200 senses a movement of the golf club and transmits information indicating a sensing result to the terminal device 500 via a wireless communication path.

The terminal device 500 is, for example, an information processing device such as a smartphone or a tablet terminal. Note that in the example illustrated in FIG. 15, the terminal device 500 includes an imaging unit 510 and an output unit 530. The output unit 530 is an output interface that presents various kinds of information to a user by displaying display information on a screen like a so-called display or the like. The imaging unit 510 images a video such as a still image or a moving image like a so-called digital camera. Note that in the example illustrated in FIG. 15, the imaging unit 510 is a so-called in-camera and can image an image of a region facing the screen of the output unit 530.

On the basis of this configuration, in the information processing system 1 illustrated in FIG. 15, the imaging unit 510 captures a video of the user Ua (in particular, indicating a movement of the body of the user Ua) and various kinds of information are presented to the user Ua via the output unit 530 oriented to the side of the user Ua. In this configuration, the user Ua can also confirm, for example, a video (for example, a moving image) based on an imaging result of the movement of the body of the user Ua by the imaging unit 510 of the terminal device 500 via the output unit 530 of the terminal device 500.

In addition, the terminal device 500 has a function of analyzing a movement of the body of the user on the basis of a sensing result of a movement of each part of the body by the body sensor device 100 or the shaft sensor device 200. Thus, the terminal device 500 can analyze, for example, a form of a swing of the user Ua by acquiring sensing results from the body sensor devices 100a to 100c or the shaft sensor device 200 and can also present an analysis result to the user Ua via the output unit 530. Note that an example of a function of analyzing a movement of the body of the user will be separately described below. In addition, the foregoing function can be realized, for example, by installing a predetermined application in the terminal device 500.

Note that the configuration illustrated in FIG. 15 is merely an example and the system configuration of the information processing system 1 according to the embodiment is not necessarily limited. As a specific example, a different imaging device from the terminal device 500 may be applied as the imaging unit that captures a video of the user Ua. In addition, another output device (for example, an externally detached display) different from the output unit 530 may be applied as an output destination to which various kinds of information are output by the terminal device 500.

The example of the system configuration of the information processing system 1 according to the embodiment has been described above with reference to FIG. 15.

<3.2. UI>

Next, an example of a UI for presenting an analysis result of a movement of the body of the user by the information processing system according to the embodiment will be described. Note that an example of a case in which the terminal device 500 analyzes a movement (for example, a swing form) of the body of the user at the time of a swing of golf on the basis of a sensing result by the body sensor device 100 or the shaft sensor device 200 and presents information based on an analysis result to the user will be described in this section.

(1) Menu Screen

Figure 16:
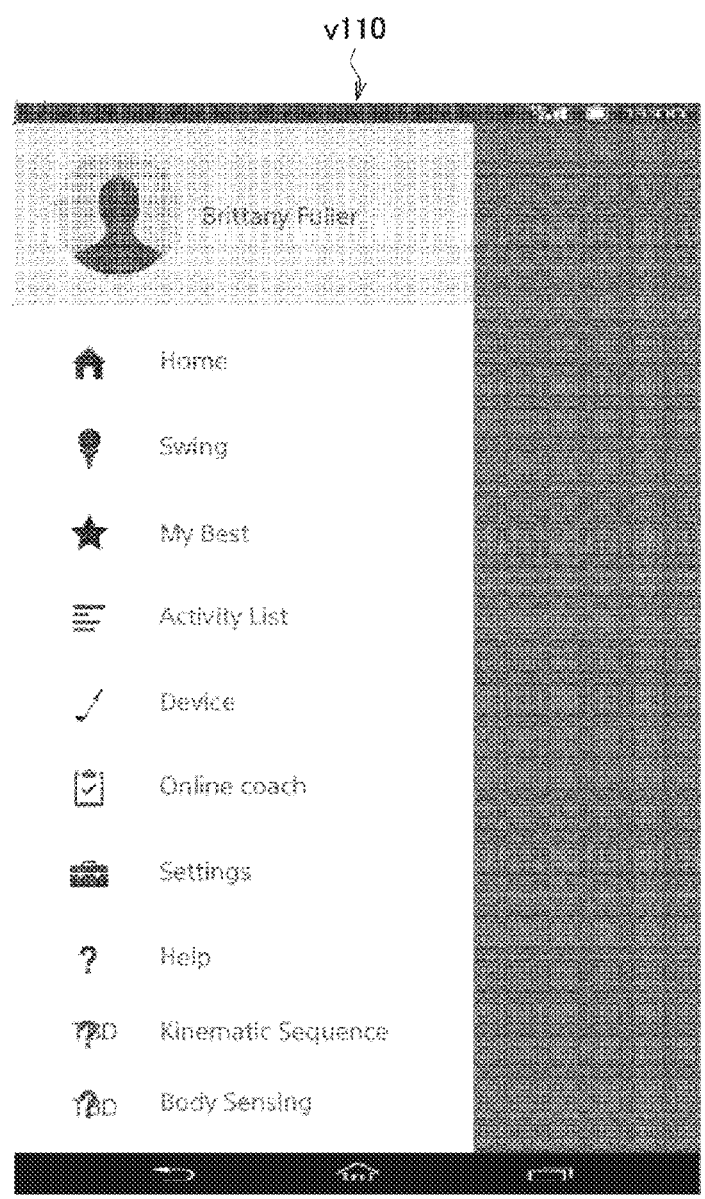
FIG. 16 is a diagram illustrating an example of a menu screen in a UI according to the embodiment.

First, an example of a menu screen in the UI according to the embodiment will be described with reference to FIG. 16. FIG. 16 is a diagram illustrating an example of the menu screen in the UI according to the embodiment. As illustrated in FIG. 16, various functions supplied to the user by the terminal device 500 via the UI according to the embodiment are presented as a list on a menu screen v110.

When an item presented on the menu screen v110 is selected on the basis of a manipulation via a predetermined input unit, the terminal device 500 presents a screen corresponding to the item (that is, a screen of a function indicating the item) to the user via the output unit 530.

Note that an example of a function corresponding to an item presented on the menu screen v100 and an example of a screen corresponding to the function will be separately described below.

(2) Home Screen

Figure 17:
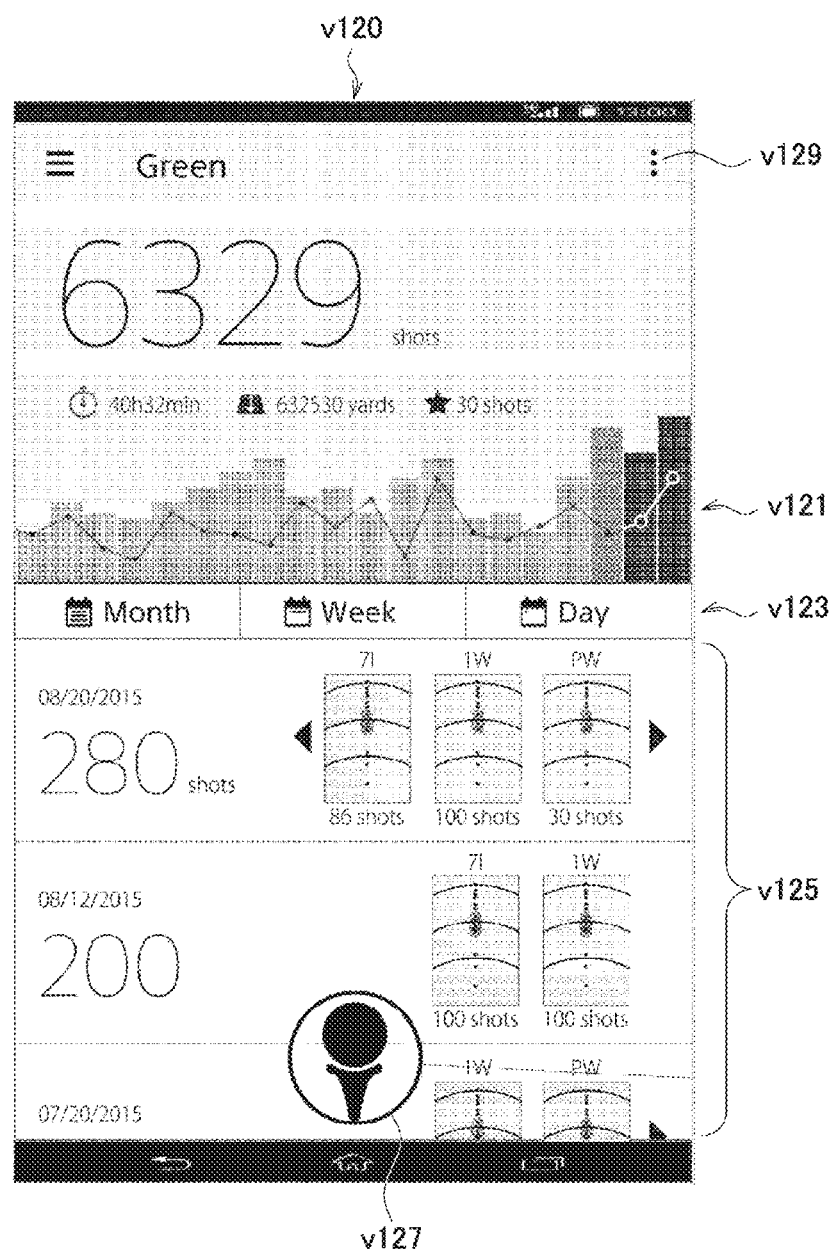
FIG. 17 is a diagram illustrating an example of a home screen in the UI according to the embodiment.

Next, an example of a home screen in the UI according to the embodiment will be described with reference to FIG. 17. FIG. 17 is a diagram illustrating an example of the home screen in the UI according to the embodiment. As illustrated in FIG. 17, data accumulated as an analysis result of a swing form, information based on an aggregate result of the accumulated data, and the like are presented as a summary on a home screen v120.

For example, in a region denoted by reference numeral v121, the number of shots (that is, the number of analyzed swings) or a practice time of a swing performed using the body sensor device 100 or the shaft sensor device 200 is presented as a graph for each predetermined unit. More specifically, in the example illustrated in FIG. 17, a bar graph indicates a transition of the number of shots for each predetermined period (for example, a month, a week, or every day). A line graph indicates a transition of the practice time for each predetermined time. Note that the presenting unit of the graph indicating the transition of the number of shots or the practice time may be switched on the basis of a predetermined manipulation. For example, in the example illustrated in FIG. 17, as denoted by reference numeral v123, a tab for switching a period serving as a presenting unit of various kinds of information among "Month," "Week," and "Day" is presented. That is, when the tab v123 is manipulated, the graph indicating the transition of the number of shots or the practice time is presented in the region v121 using a period corresponding to the manipulation target tab v123 as the presenting unit of the information.

In addition, in a region denoted by reference numeral v125, a summary of data accumulated as an analysis result of the swing form is presented using the period designated on the basis of the tab v123 as the presenting unit. For example, in the example illustrated in FIG. 17, the information indicating the number of shots is presented in the region v125. In addition, in the region v125, a carry map indicating a distribution of a carry distance of a ball simulated on the basis of an analysis result of a swing is presented for each golf club used in a practice as another piece of information. Note that the example illustrated in FIG. 17 is merely an example and types of information presented for each predetermined period are not necessarily limited. In addition, the types of presenting target information may be switched selectively in response to, for example, a change in various kinds of settings.

An icon denoted by reference numeral v129 is an input interface for selectively switching at least a part of information presented on the home screen v120. As a specific example, information presented as a simulation result of the carry distance of the ball based on the analysis result of the swing form may selectively switched among a total sum, a maximum value, and an average value between a plurality of pieces of data through a manipulation on the icon v129. Of course, types of information switched through a manipulation on the icon v129 or types of switching target options are not necessarily limited to the example described above, but may be appropriately set in accordance with a use scene of the UI according to the embodiment.

An icon denoted by reference numeral v127 is an input interface used for the user to support start of a practice on the terminal device 500. That is, when a manipulation on the icon v127 is accepted, the terminal device 500 starts, for example, various processes related to analysis of a swing form such as various kinds of settings for starting the analysis of the swing form and acquisition of the sensing result from the body sensor device 100 or the shaft sensor device 200.

The example of the home screen on the UI according to the embodiment has been described above with reference to FIG. 17.

(3) Suggestion of Information for Each Golf Club

Figure 20:
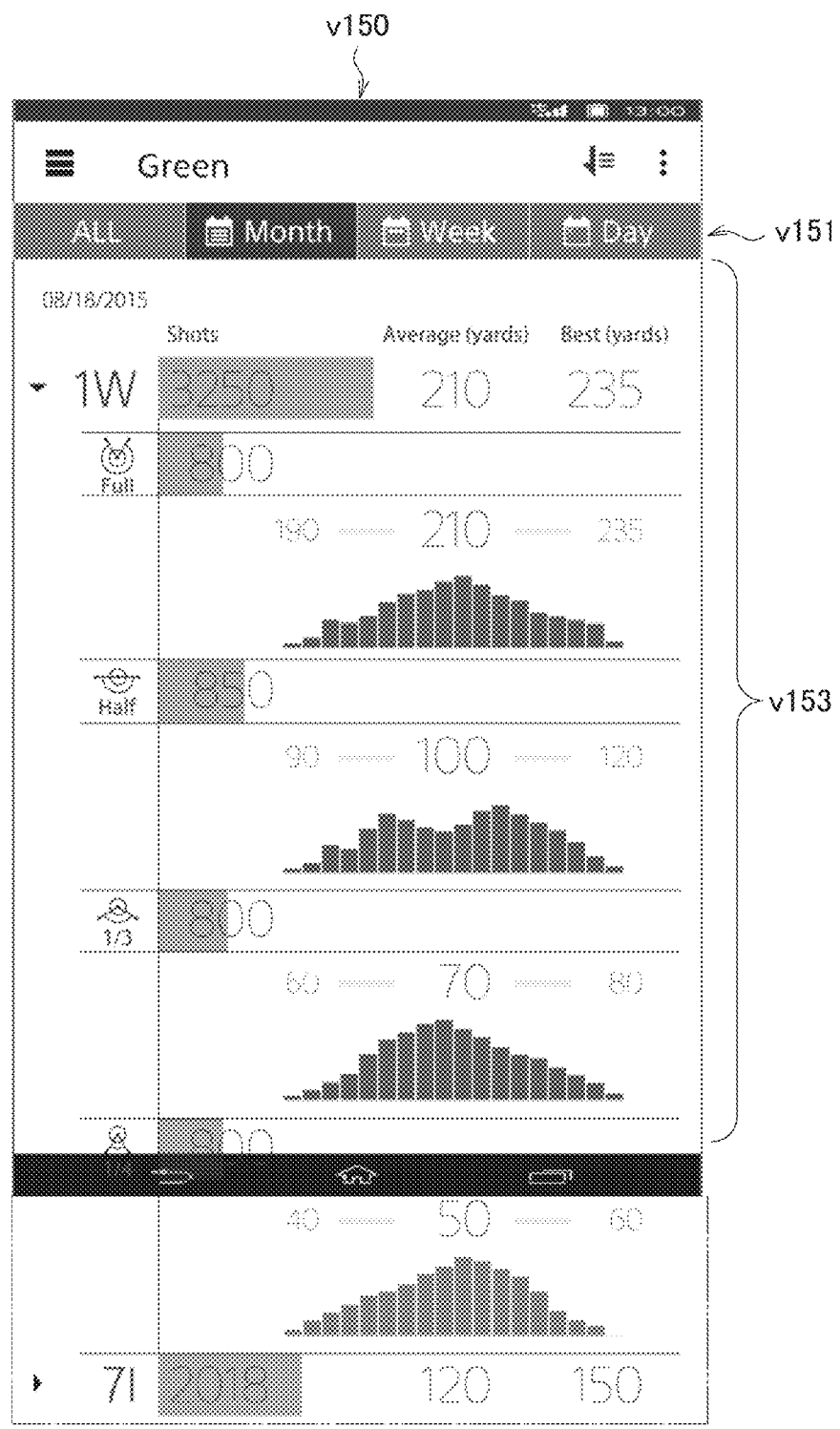
FIG. 20 is a diagram illustrating another example of the suggestion screen of information based on the accumulated data in the UI according to the embodiment.

Next, examples of screens for suggesting information based on data accumulated as an analysis result for each golf club will be described with reference to FIGS. 18 to 20.

Figure 18:
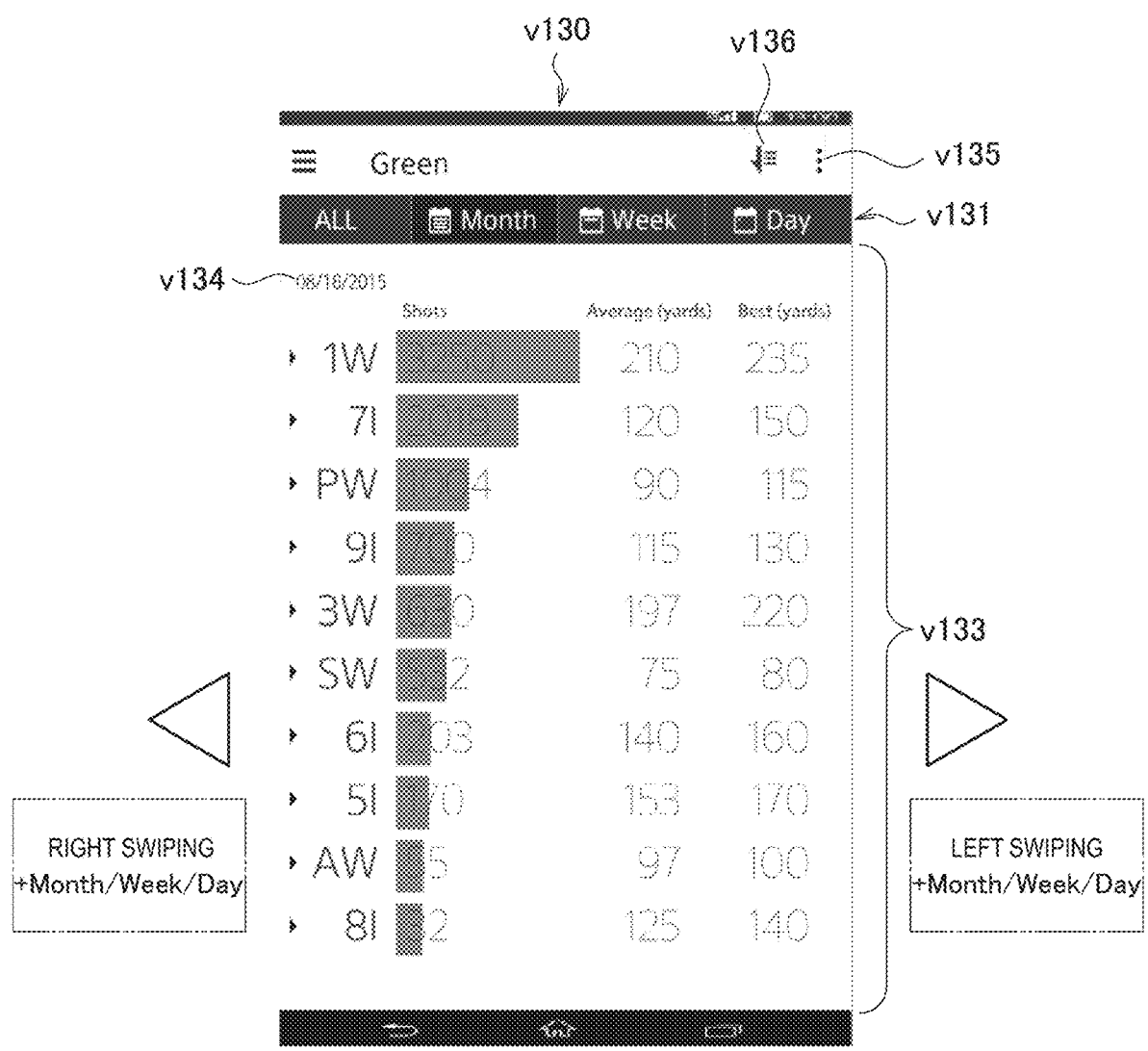
FIG. 18 is a diagram illustrating an example of a suggestion screen of information based on accumulated data in the UI according to the embodiment.

For example, FIG. 18 is a diagram illustrating an example of a suggestion screen of information based on accumulated data in the UI according to the embodiment. Specifically, on a screen v130 illustrated in FIG. 18, information indicating each of the number of shots and a simulation result of a carry distance of a ball is presented for each golf club in a region denoted by reference numeral v133. Note that information regarding the number of shots and the carry distance for each golf club is presented in order in which the number of shots is more on the screen v130.

In addition, a tab denoted by reference numeral v131 is an input interface for designating a presenting unit of the information regarding the number of shots and the carry distance presented for each golf club. For example, in the example illustrated in FIG. 18, the tab v131 for switching the presenting unit of the information regarding the number of shots or the carry distance between "ALL," "Month," "Week," and "Day" is presented. That is, when the tab v131 is manipulated, the information regarding the number of shots and the carry distance is presented for each golf club in the presenting unit corresponding to the manipulation target tab v131 in the region v133. Note that the tab v131 shown as "ALL" means that all the previously accumulated data is designated as a presenting target.

In addition, in the region v133, information indicating a date which is a presenting target of information regarding the number of shots and the carry distance may be presented, as denoted by reference numeral v134. For example, in a case in which monthly information is presented in the region v133, information (for example, information indicating a year and a month) indicating a month which is a presenting target of information is presented as the information v134 indicating the date. In addition, in a case in which weekly information is presented in the region v133, information (for example, information indicating a year, a month, and a week) indicating a week which is a presenting target of the information is presented as the information v134 indicating the date. Similarly, in a case in which daily information is presented in the region v133, information (for example, information indicating a year, a month, and a day) indicating a day which is a presenting target of the information is presented as the information v134 indicating the date. Note that in a case in which the previously accumulated data is all selected as a presenting target, the information v134 indicating the date may not be displayed.

In a case in which one of "Month," "Week," and "Day" is selected as the presenting unit of the information regarding the number of shots and the carry distance on the screen v130, the date which is the presenting target of the information may be changed in a case in which a predetermined manipulation (for example, a swiping manipulation) related to the switching of the screen is accepted. Specifically, in a case in which a swiping manipulation is performed leftwards in a situation in which the monthly information is presented in the region v133, information corresponding to a month later than a month which is the presenting target of the information before a manipulation may be presented in the region v133. In addition, in a case in which a swiping manipulation is performed rightwards, information corresponding to a month earlier than the month which is the presenting target of the information before a manipulation may be presented in the region v133. In addition, in a case in which a swiping manipulation is accepted in a situation in which the weekly information is presented in the region v133, information corresponding in a direction of the swiping manipulation may be presented in the region v133 between information corresponding to an earlier week and information corresponding to a later week than a week which is the presenting target of the information before a manipulation. The same also applies to a case in which daily information is presented in the region v133.

Information indicating an average value of carry distances for a period designated as the presenting unit of the information and information indicating a maximum value of the carry distance for the period are presented on the screen v130 as information regarding a carry distance of each golf club. On the other hand, types of information regarding the carry distance presented in the region v133 may be selectively switched. For example, a pull-down menu denoted by reference numeral v135 is an input interface for selectively switching at least a part of information presented in the region v133. As a specific example, at least a part of information regarding the carry distance presented in the region v133 may be selectively switched, for example, among a total sum, a maximum value, and an average value for a period designated as the presenting unit of the information through a manipulation on the pull-down menu v135.

An icon denoted by reference numeral v136 is an input interface for designating a condition for rearranging information for each golf club presented in the region v133. For example, on the screen v130 illustrated in FIG. 18, the information for each golf club is presented in the order in which the number of shots is more. However, the information for each golf club may be rearranged on the basis of a different condition from the number of shots through a manipulation on the icon v136.

For example, FIG. 19 is a diagram illustrating another example of the suggestion screen of information based on the accumulated data in the UI according to the embodiment. Specifically, a screen v140 illustrated in FIG. 19 shows an example of a case in which the information for each golf club presented on the screen v130 illustrated in FIG. 18 is rearranged and presented in a number order of golf clubs.

In addition, more detailed information corresponding to a gold club may be presented by selecting the information for each golf club presented in the region v133 of the screen v130 illustrated in FIG. 18. For example, FIG. 20 is a diagram illustrating still another example of the suggestion screen of information based on the accumulated data in the UI according to the embodiment and illustrates an example of a screen in a case in which more detailed information for each golf club is suggested. For example, on a screen v150 illustrated in FIG. 20, information indicating a total number of shots and information indicating a distribution of the number of shots for each carry distance are presented for each type of swing (for example, "Full," "Half," "⅓," and "¼") in accordance with an amplitude in a region denoted by reference numeral v153 with regard to the selected golf club. In addition, the presenting unit of the information presented in the region v153 can be switched in a tab denoted by reference numeral v151, like the screen v130 illustrated in FIG. 18.

The examples of the screens for presenting the information based on the data accumulated as the analysis result for each golf club has been described above with reference to FIGS. 18 to 20.

(4) Initial Setting Screen for Analyzing Swing Form

Next, examples of screens related to initial setting for sensing a movement of the body of the user at the time of a swing by the body sensor device 100 or the shaft sensor device 200 and analyzing a swing form will be described.

Figure 21:
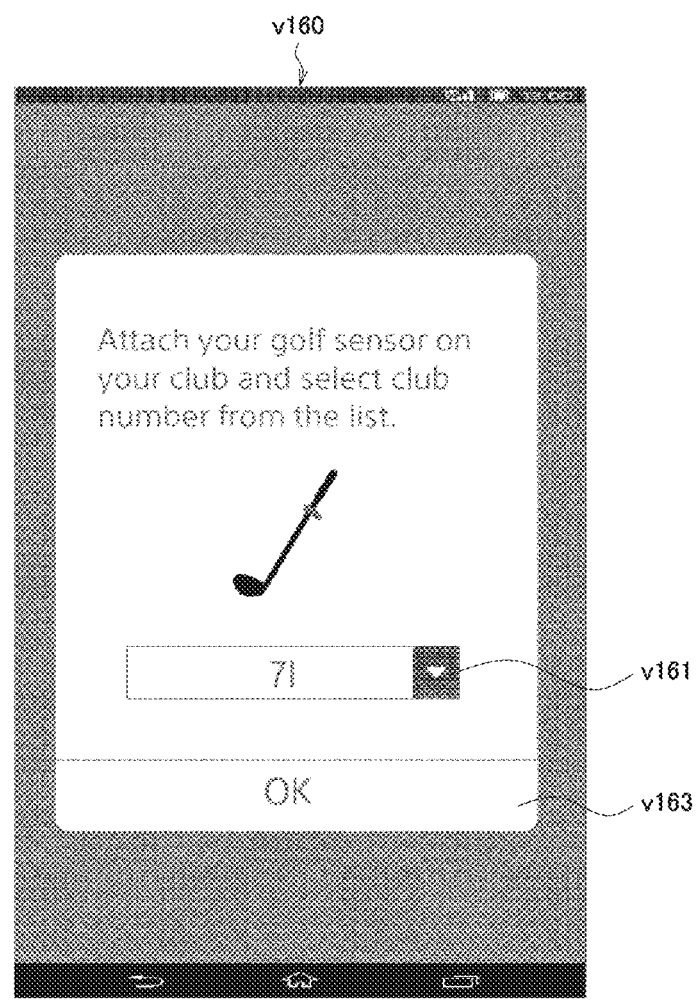
FIG. 21 is a diagram illustrating an example of an initial setting screen for analyzing a swing form in the UI according to the embodiment.

For example, FIG. 21 is a diagram illustrating an example of an initial setting screen for analyzing a swing form in the UI according to the embodiment. FIG. 21 illustrates an example of a screen on which a golf club to be used is selected. The user designates a golf club number to be used by manipulating a pull-down denoted by reference numeral v161 and decides a golf club to be used by manipulating an OK button denoted by reference numeral v163. By designating the golf club to be used in this way, the terminal device 500 can perform various simulations on the basis of a sensing result by the body sensor device 100 or the shaft sensor device 200. As a specific example, the terminal device 500 can calculate a swing speed or the position of an impact on the basis of the sensing result by the body sensor device 100 or the shaft sensor device 200. Therefore, the terminal device 500 can also simulate a ball flight or a carry distance, for example, on the basis of a calculation result of a swing speed or the position of an impact and setting of the golf club to be used (for example, a face angle of the selected golf club).

Figure 22:
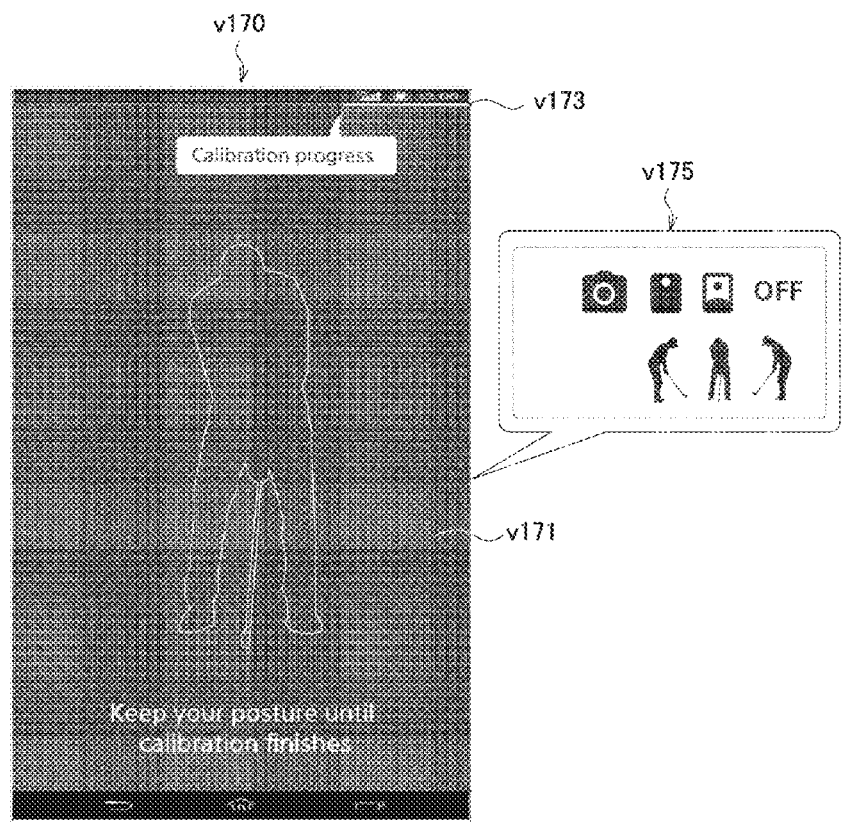
FIG. 22 is a diagram illustrating another example of the initial setting screen for analyzing a swing form in the UI according to the embodiment.

In addition, FIG. 22 is a diagram illustrating another example of the initial setting screen for analyzing a swing form in the UI according to the embodiment. FIG. 22 illustrates an example of a screen on which various sensors installed in the body sensor device 100 or the shaft sensor device 200 are calibrated. Specifically, on a screen v170 illustrated in FIG. 22, image information (for example, a silhouette) indicating a posture state of the golf club is presented in a region denoted by reference numeral v171 so that the user is notified that the posture state of the golf club is kept, like the image information. In this way, the terminal device 500 presents the screen v170 to the user so that the user performs initial setting (for example, recognition of an initial position) of the body sensor device 100 or the shaft sensor device 200 for a period in which the posture state of the golf club is kept. In addition, as denoted by reference numeral v173 at this time, information indicating progress situations of calibration of various sensors may be presented as a progress bar.

In addition, as denoted by reference numeral v173, an option menu for selectively switching information to be presented in the region v171 may be installed. As a specific example, an image captured by a predetermined imaging unit (for example, the imaging unit 510 of the terminal device 500) may be displayed in the region v171 by designation from the option menu v173. For example, when an image of the user captured by a predetermined imaging unit is displayed in the region v171, the user can adjust the position of the body or a posture of the golf club so that an imaging result of the user substantially matches the silhouette presented in the region v171.

In addition, as another example, an imaging unit that captures an image to be displayed in the region v171 may be selectively switched by designation from the option menu v173. For example, in the example illustrated in FIG. 22, one of an imaging unit (in-camera) installed on the side of the output unit 530 of the terminal device 500, an imaging unit (an out-camera) installed on the opposite side to the output unit 530 of the terminal device 500, and another imaging device different from the terminal device 500 can be selected as the imaging unit that captures the image.

In addition, image information (for example, a silhouette) presented in the region v171 and indicating the posture state of the golf club may be selectively switched in accordance with a positional relation between the user and the imaging unit that captures an image of the user. For example, in a case in which a form of a swing is imaged from the rear side of the swing (that is, an opposite side to a direction in which a ball flies), a silhouette in which a posture of the user taking the golf club is imaged from the rear side of a swing may be presented as the image information.

The examples of the screens related to the initial setting for sensing the movement of the body of the user at the time of the swing by the body sensor device 100 or the shaft sensor device 200 and analyzing the swing form have been described above with reference to FIGS. 21 and 22.

(5) Suggestion of Simulation Results of Carry Distances or Ball Flights

Next, examples of screens for simulating ball flights or carry distances on the basis of sensing results by the body sensor device 100 or the shaft sensor device 200 and presenting simulation results will be described with reference to FIGS. 23 to 31. FIGS. 22 to 33 are diagrams illustrating examples of screens for suggesting simulation results of ball flights or carry distances in the UI according to the embodiment.

Figure 23:
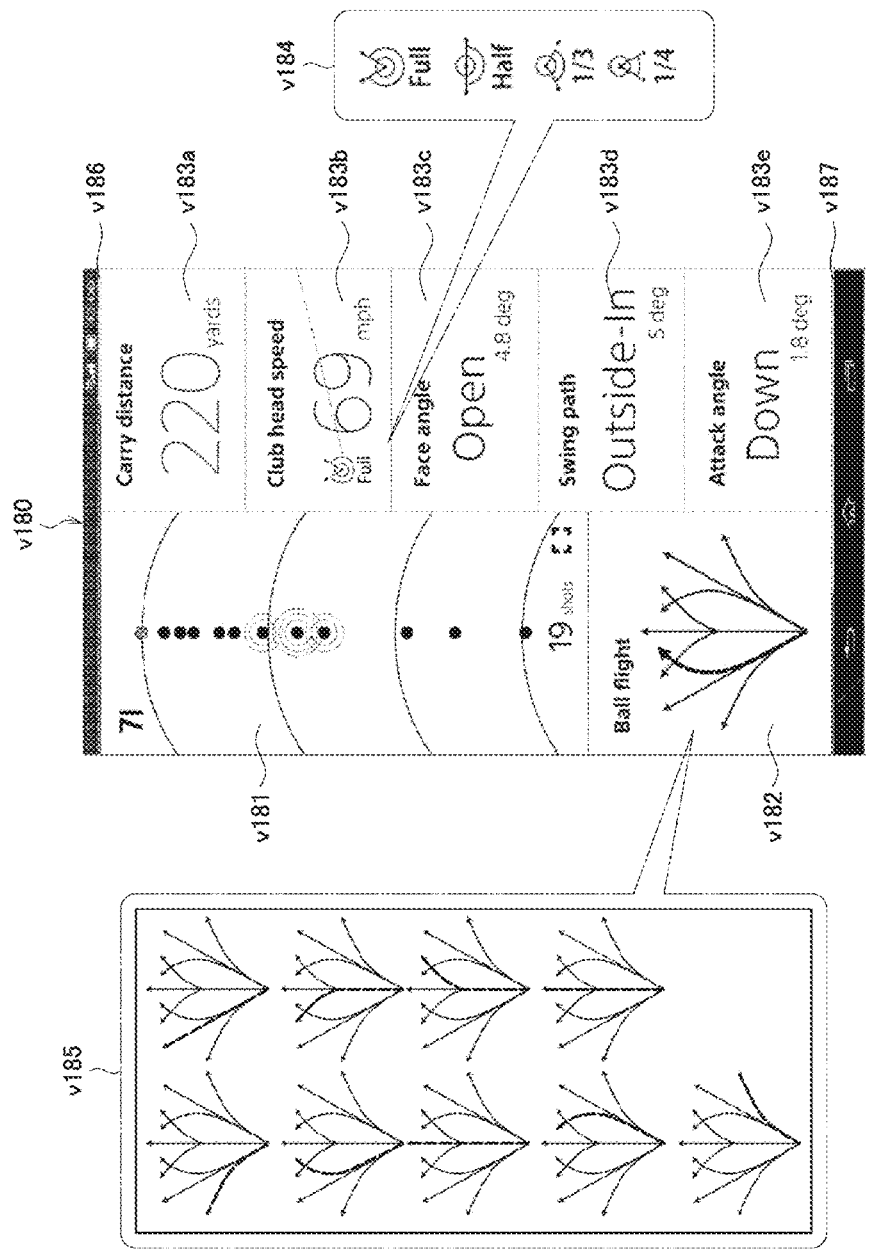
FIG. 23 is a diagram illustrating an example of a screen for suggesting a simulation result of a ball flight or a carry distance in the UI according to the embodiment.

For example, distributions of simulated carry distances, ball flights, and information based on analysis results of swings are shown on a screen v180 illustrated in FIG. 23.

As a specific example, in a region denoted by reference numeral v181, a carry map indicating a distribution of carry distances of balls simulated for each shot is shown on the basis of an analysis result of the swing equivalent to a plurality of shots. Specifically, each circular plot shown in the carry map corresponds to a simulation result of each shot. That is, a position indicated by the circular plot represents a carry distance of a shot corresponding to the plot.

In addition, in a case in which there are a plurality of shots indicating that the simulation results of the carry distances are the same value, concentric circles are added to the circular plots and are presented in the carry map in accordance with the number of shots indicating that the carry distances are the same value. In this configuration, the user can intuitively recognize the number of shots indicating the carry distances corresponding to the plots in accordance with the number of concentric circles added to the circular plots.

On the basis of the above-described configuration, the user can refer to information regarding the shots corresponding to the plots (for example, simulation results of the ball flights or analysis results of swings), for example, by selecting the plots presented in the carry map.

For example, in a region denoted by reference numeral v182, information indicating a simulation result of a ball flight is presented with regard to the shots corresponding to the plot selected on the carry map. As a specific example, the terminal device 500 simulates a ball flight on the basis of a positional relation between the ball and the head of a golf club at the time of an impact and information such as an inclination angle of a face of the selected golf club on the basis of an analysis result of a swing. Then, the terminal device 500 presents display information visually indicating a ball flight in the region v182 on the basis of the simulation result of the ball flight. For example, in the example illustrated in FIG. 23, display information in which an arrow indicating a simulation result is emphasized and displayed among arrows indicating a plurality of kinds of ball flights is presented as the display information displayed in the region v182. Note that, for example, an example denoted by reference numeral v185 can be given as a variation of the display information visually indicating the simulation results of the ball flights.

In addition, as denoted by reference numerals v183a to v183e, various kinds of information indicating analysis results of swings are presented with regard to shots corresponding to the plots selected on the carry map. For example, in the region v183a, a simulation result of the carry distance of a corresponding shot is shown as a numerical value. In addition, in the region v183b, information indicating a type of a swing in accordance with amplitude and information indicating a calculation result of a head speed of the golf club are presented. Note that, for example, examples denoted by reference numeral v184 (that is, "Full," "Half," "⅓," "¼," and the like) can be given as information indicating the types of swings. In addition, in the region v183c, information indicating an inclination angle of the face of a golf club is presented. In addition, in the region v183d, information indicating trajectories of swings (for example, "Outside-In," "Inside-In," "Inside-Out," and the like) is presented. In addition, information indicating a calculation result of an angle at which a ball collides with a face portion of a golf club (that is, an attach angle) is presented in the region v183e.

In addition, a plurality of kinds of screens (for example, a screen for each golf club) may be selectively switched by a tab or the like on the screen v180. Therefore, for example, in the example illustrated in FIG. 23, a tab indicator indicating a displayed screen among a plurality of kinds of screens may be presented as denoted by reference numeral v187.

In addition, an indicator indicating an analysis preparation situation of a subsequent swing may be presented as denoted by reference numeral v186 on the screen v180.

Figure 24:
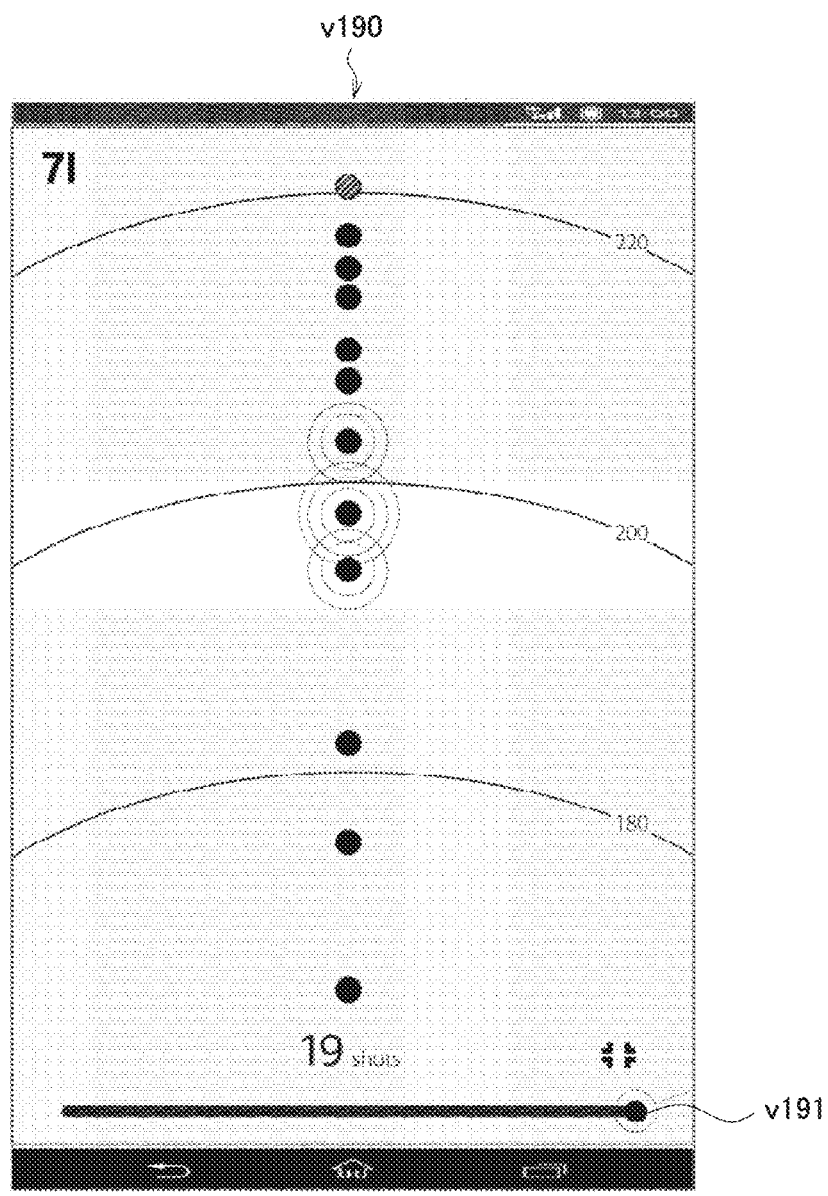
FIG. 24 is a diagram illustrating an example of a screen for suggesting a simulation result of a ball flight or a carry distance in the UI according to the embodiment.

In addition, a screen v190 illustrated in FIG. 24 shows an example of a case in which the carry map presented in the region v181 of the screen v180 illustrated in FIG. 23 is expanded and displayed. As illustrated in FIG. 24, a seeking bar v191 formed so that a slider can be manipulated in the horizontal direction is presented on the screen v190. Among the position of the seeking bar v191 in the horizontal direction, the left end corresponds to oldest data among data of each shot which is an information presenting target and the right end corresponds to newest data. That is, when the slider of the seeking bar v191 is manipulated from the left end to the right end, the plots corresponding to the data are added to the carry map in the order in which the data is acquired. In addition, when the slider of the seeking bar v191 is manipulated from the right end to the left end, the plots corresponding to the newest data are deleted in sequence from the carry map among the plots presented on the carry map. In this configuration, the user can visually confirm a transition of shots during practice chronologically, for example, by manipulating the seeking bar v191 rightwards or leftwards.

Figure 25:
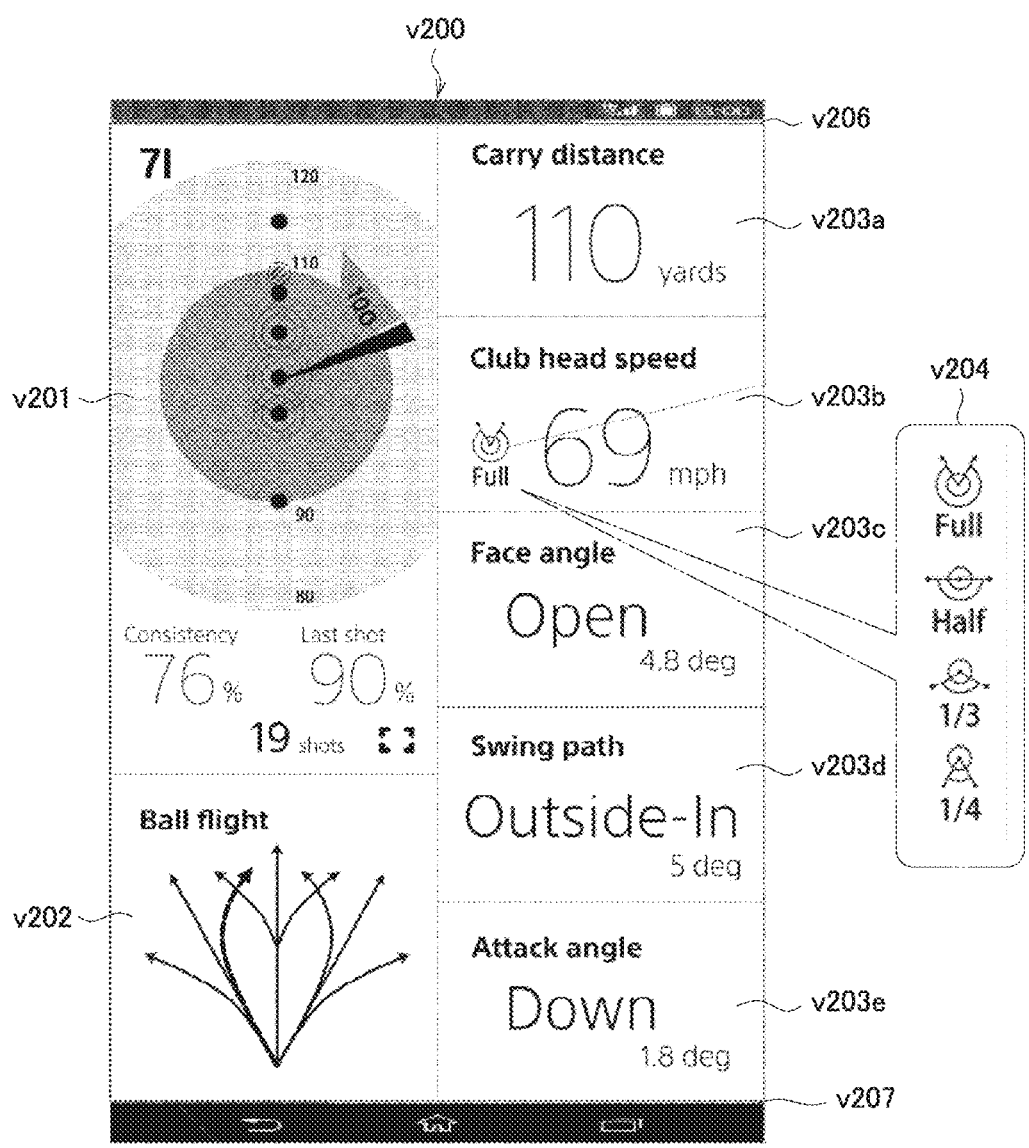
FIG. 25 is a diagram illustrating an example of a screen for suggesting a simulation result of a ball flight or a carry distance in the UI according to the embodiment.

In addition, a screen v200 illustrated in FIG. 25 is diagram illustrating a mode of information presented as the carry map. The screen v200 illustrated in FIG. 25 is different from the screen v180 illustrated in FIG. 23 in the mode of the carry map presented in a region denoted by reference numeral v201. Specifically, in the example illustrated in FIG. 25, for example, information indicating accuracy of shots (in other words, information indicating a dispersion of the carry distance for each shot) using a predetermined carry distance as a reference or information indicating divergence of the carry distance for each shot from the carry distance serving as a reference is presented as a score. Note that information denoted by reference numerals v202 to v207 is the same information denoted by reference numerals v182 to v187 on the screen v180 illustrated in FIG. 23.

Figure 26:
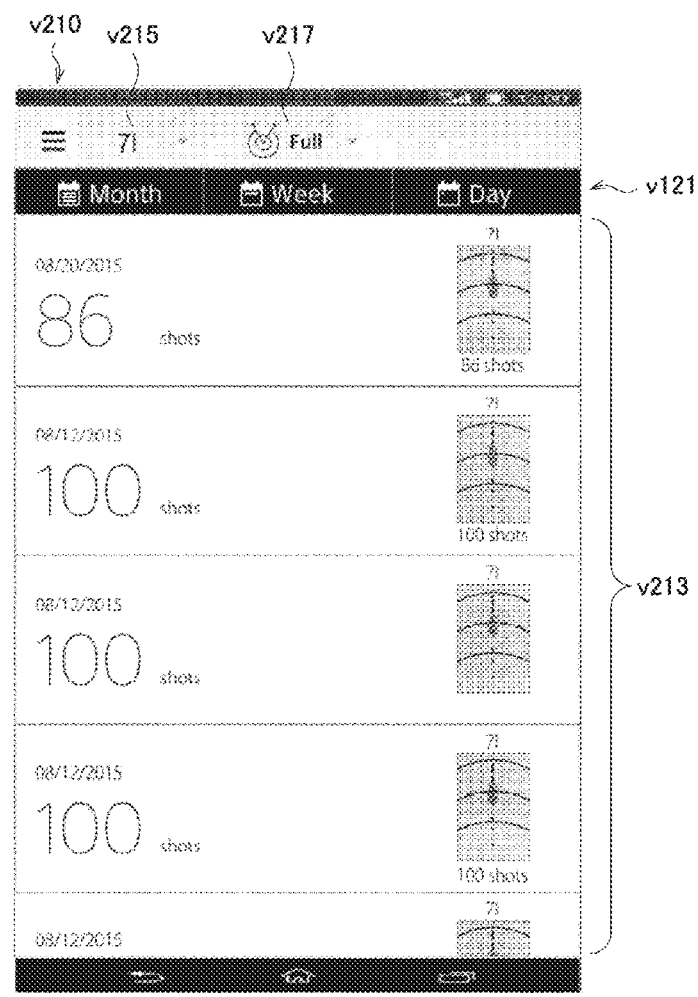
FIG. 26 is a diagram illustrating an example of a screen for suggesting a simulation result of a ball flight or a carry distance in the UI according to the embodiment.

In addition, a screen v210 illustrated in FIG. 26 is an example of a screen on which a list of data acquired previously and indicating simulation results of the carry distances or the ball flights is presented as a history. Specifically, on the screen v210 illustrated in FIG. 26, a carry map and information indicating the number of shots is presented as a list for each period set as a presenting unit of information in a region denoted by reference numeral v213. Note that the presenting unit of the information presented in the region v213 can be switched by, for example, a tab denoted by reference numeral v211. As a specific example, on the screen v210 illustrated in FIG. 26, "Month," "Week," and "Day" can be designated as the presenting unit of the information.

In addition, a function of filtering information presented in the region v213 on the basis of a predetermined condition may be installed. For example, a pull-down menu illustrated by reference numeral v215 is an input interface for filtering the information presented in the region v213 using a golf club number as a condition. That is, when the golf club number is designated on the basis of a manipulation on the pull-down menu v215, data corresponding to the designated golf club number is extracted and presented as a list in the region v213. In addition, a pull-down menu denoted by reference numeral v217 is an input interface for filtering the information presented in the region v213 using a type of swing in accordance with the amplitude as a condition. That is, when a type of swing is designated on the basis of a manipulation on the pull-down menu v217, data corresponding to the designated type of swing is extracted and presented as a list in the region v213.

Figure 27:
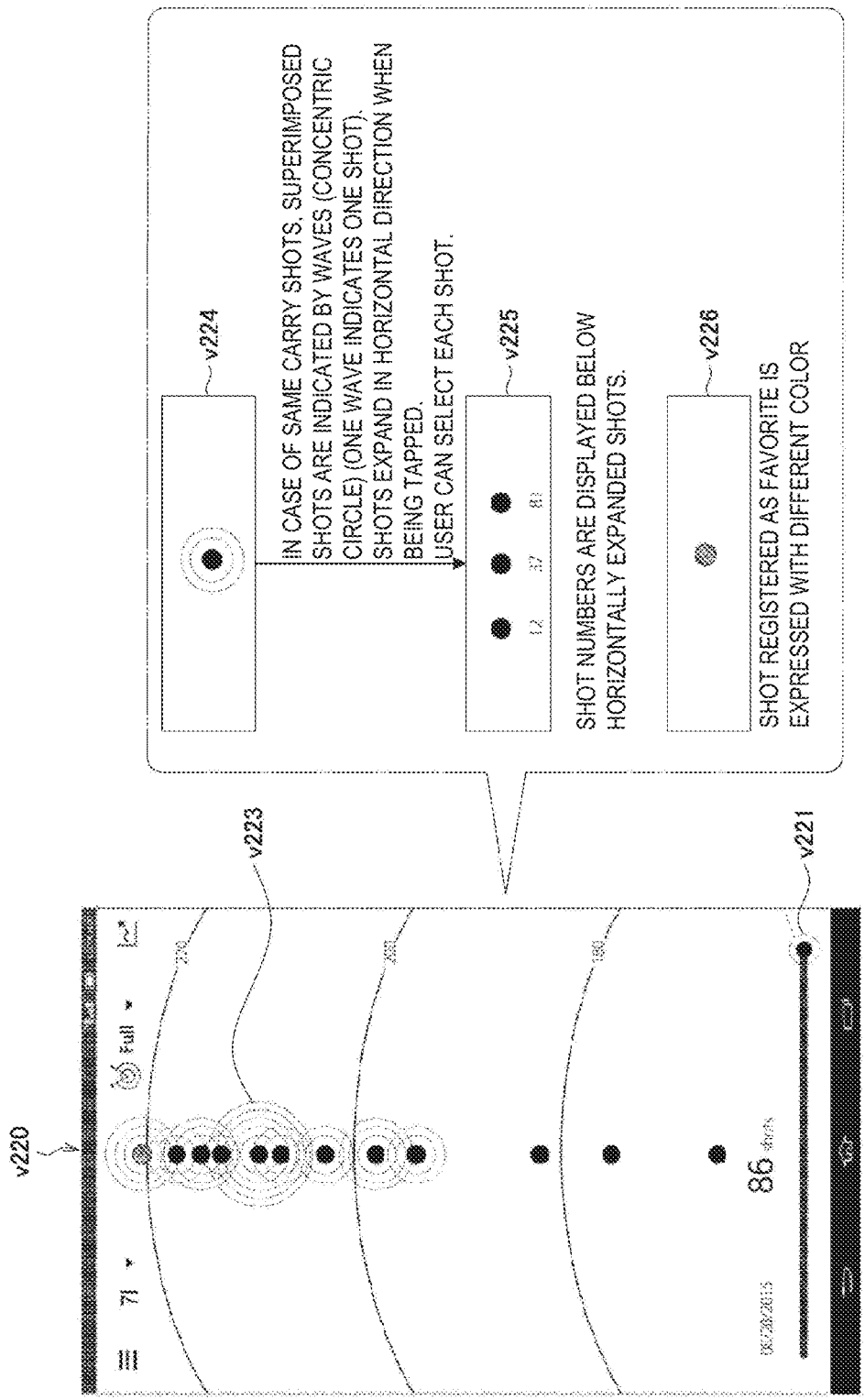
FIG. 27 is a diagram illustrating an example of a screen for suggesting a simulation result of a ball flight or a carry distance in the UI according to the embodiment.

Next, an example of a screen for presenting the carry map selected from the history illustrated in FIG. 26 will be described with reference to FIG. 27. As illustrated in FIG. 27, a distribution of the carry distance of the ball simulated for each shot is presented on a screen v220 on which the carry map selected from the history is presented, like the screen v190 described with reference to FIG. 24.

In addition, as illustrated in FIG. 27, a seeking bar v221 formed so that a slider can be manipulated in the horizontal direction is presented on the screen v220. The seeking bar v221 is an input interface for designating a date which is a presenting target of a carry map. Among the position of the seeking bar v221 in the horizontal direction, the left end corresponds to oldest data of the date in each piece of data which is a presenting target of the information and the right end corresponds to data of a newest date. That is, when the seeking bar v221 is manipulated, a carry map based on data corresponding to a date in accordance with a position of the slider is displayed. In this configuration, the user can chronologically confirm a transition of the carry map for each date, for example, by manipulating the seeking bar v221 rightwards or leftwards.

In addition, in a case in which there are a plurality of shots indicating that the simulation results of the carry distances are the same value, concentric circles are added to the circular plots and are presented in the carry map in accordance with the number of shots indicating that the carry distances are the same value, as denoted by reference numeral v223. More specifically, each concentric circle added to the circular plot corresponds to data equivalent to one shot. In this configuration, the user can intuitively recognize the number of shots indicating the carry distances corresponding to the plots in accordance with the number of concentric circles added to the circular plots.

In addition, when the plots to which the concentric circles are added are selected through a tapping manipulation or the like, data corresponding to each of the plurality of shots indicated by the plots and the concentric circles is presented to be developed as mutually different plots in the horizontal direction. For example, a plot denoted by reference numeral v224 indicates that data equivalent to 3 shots is included. When this plot is selected through a tapping manipulation or the like, as denoted by reference numeral v225, the plots respectively corresponding to data equivalent to 3 shots are presented to be developed in the horizontal direction. At this time, information indicating a shot number may be associated with the plot corresponding to each shot to be presented.

In addition, as will be described in detail, a simulation result (for example, a swing analysis result) of a desired shot can also be registered as a favorite. Therefore, a plot corresponding to the shot registered as the favorite may be presented in a different display mode from the plots corresponding to the other shots. For example, in the example illustrated in FIG. 27, as denoted by reference numeral v226, the plot corresponding to the shot registered as the favorite is presented with a different color from the plots corresponding to the other shots.

Note that a function of filtering information which is a presenting target on the basis of various conditions (for example, a golf club number or a type of swing) may be installed on the screen v220 like the screen v210 described with reference to FIG. 26. In this case, the input interfaces (for example, the input interfaces equivalent to the pull-down menus v215 and v217 illustrated in FIG. 26) for designating a filtering condition may be presented on the screen v220.

Figure 28:
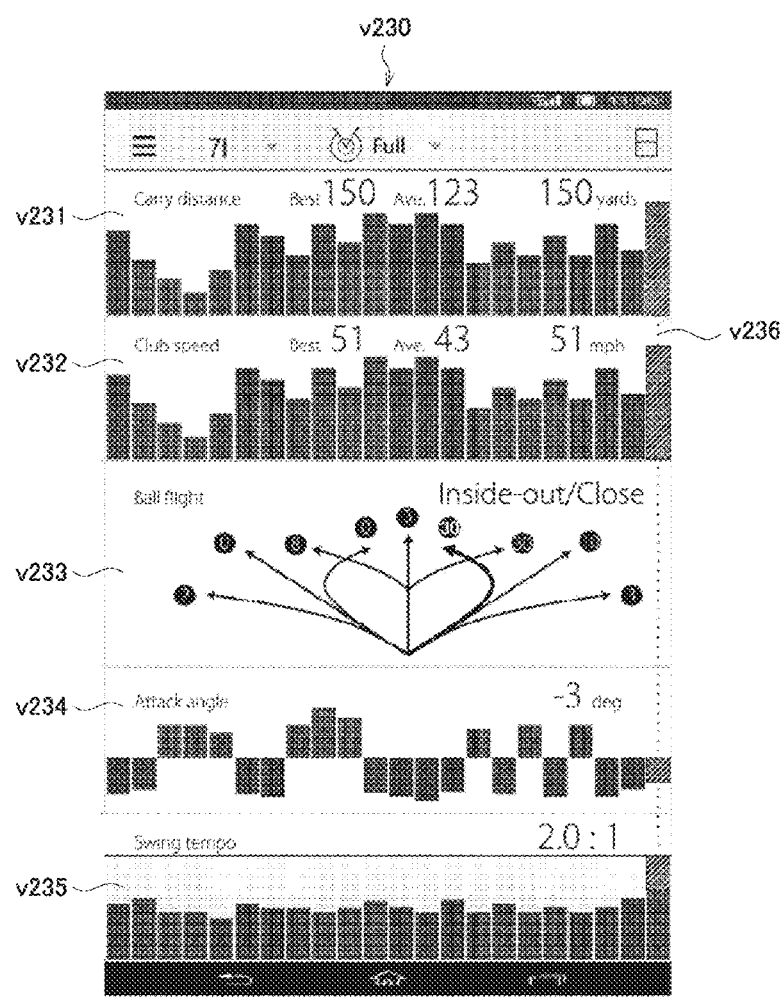
FIG. 28 is a diagram illustrating an example of a screen for suggesting a simulation result of a ball flight or a carry distance in the UI according to the embodiment.

Next, an example of a screen for presenting a simulation result of a ball flight or a carry distance or an analysis result of a swing as a history will be described with reference to FIG. 28. For example, a history of information indicating each of a carry distance, a head speed of a golf club, a ball flight, an attack angle, and a swing tempo is presented on a screen v230 illustrated in FIG. 28 on the basis of a simulation result of a ball flight or a carry distance accumulated previously or data indicating an analysis result of a swing.

Specifically, in a region denoted by reference numeral v231, a history of information indicating a simulation result of a carry distance is presented chronologically as a bar graph for each shot. In addition, in a region denoted by reference numeral v232, a history of information indicating a calculation result of a head speed of a golf club is presented chronologically as a bar graph for each shot. In addition, in a region denoted by reference numeral v234, a history of information indicating a calculation result of an attack angle is presented chronologically as a bar graph for each shot. In addition, in a region denoted by reference numeral v235, a history of information indicating an analysis result of a swing tempo is presented chronologically as a band graph for each shot. In this configuration, the user can chronologically confirm various kinds of analysis of swings and a transition of the simulation results of the carry distances in accordance with previous practice results.

In addition, in a region denoted by reference numeral v233, a history of information indicating simulation results of the ball flights is presented as a distribution of data for each ball flight. In this configuration, the user can confirm a tendency of the simulation results of the ball flights in accordance with the previous practice results.

In addition, a function of filtering information which is a presenting target on the basis of various conditions (for example, a golf club number or a type of swing) may be installed on the screen v230 like the screen v210 described with reference to FIG. 26. In this case, the input interfaces (for example, the input interfaces equivalent to the pull-down menus v215 and v217 illustrated in FIG. 26) for designating a filtering condition may be presented on the screen v230.

Note that the examples of the screens described with reference to FIGS. 22 to 28 are merely examples, and the types and modes of the information displayed in the screens or positions at which various kinds of information are presented (that is, layouts of the screens) are not necessarily limited to the examples described with reference to FIGS. 22 to 28.

Figure 29:
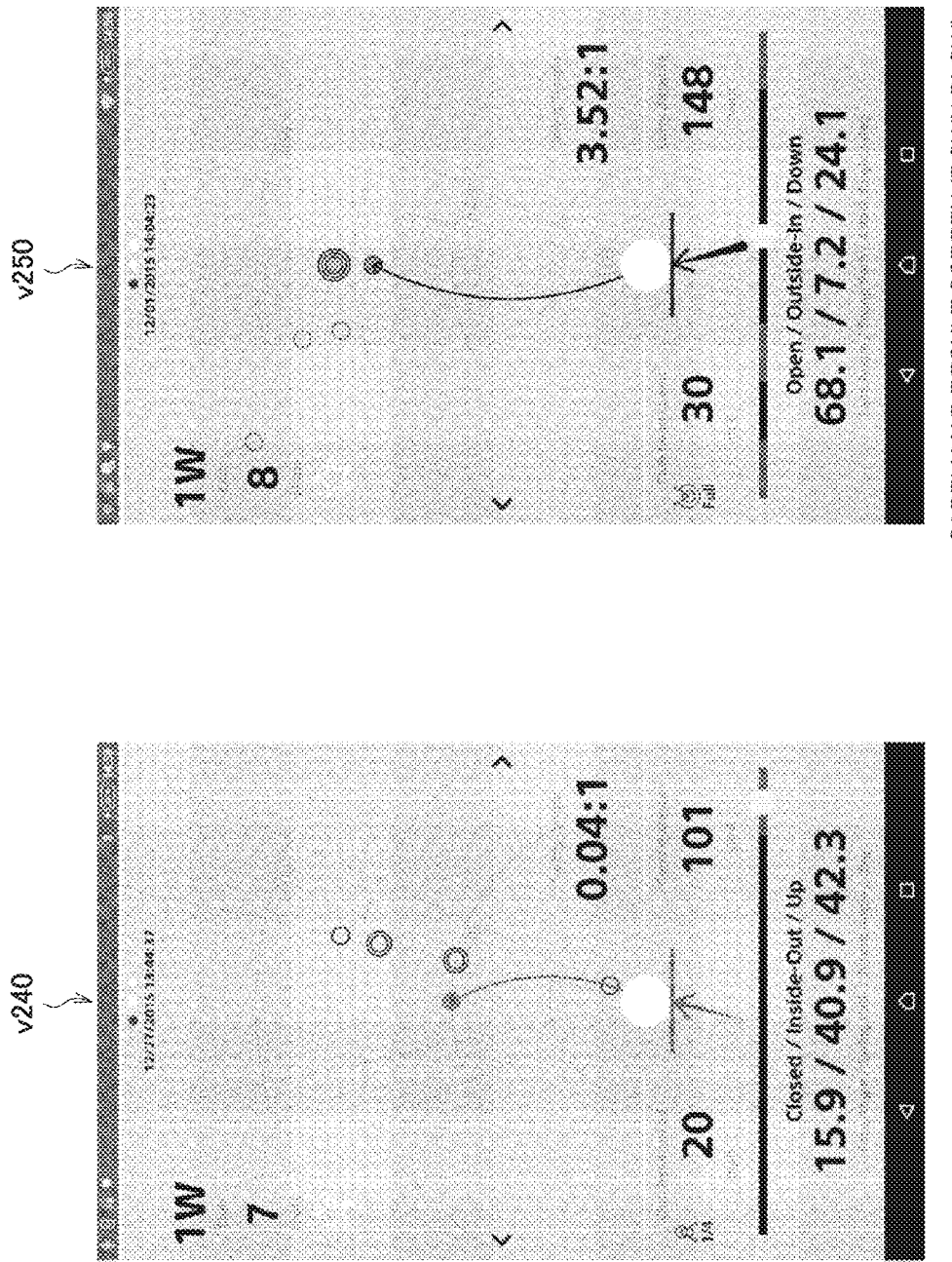
FIG. 29 is a diagram illustrating an example of a screen for suggesting a simulation result of a ball flight or a carry distance in the UI according to the embodiment.

For example, FIG. 29 illustrates examples of screens on which carry maps based on simulation results of ball flights or carry distances are presented. As a specific example, as illustrated in FIG. 29, a screen v240 on which information is presented in a case in which an upper blow swing is performed and a screen v250 on which information is presented in a case in which a down blow swing is performed may be presented to be selectively switched as a screen on which the carry map is presented.

In addition, in the example illustrated in FIG. 29, in a presenting mode of the carry map, information indicating a distribution of carry distances is presented for each ball direction unlike the carry maps described with reference to FIGS. 23 and 24. Specifically, in the example illustrated in FIG. 29, a plot in accordance with the simulation result of the carry distance for each swing is presented in each of 5 right and left directions when the front is a reference. In addition, even in the example illustrated in FIG. 29, as in the example described with reference to FIG. 27, a concentric circle may be added to a circular plot to be presented in accordance with the number of shots indicating that the carry distances are the same value in the carry map in a case in which there are a plurality of shots indicating that the simulation results of the carry distances are the same value in each direction.

In addition, in the example illustrated in FIG. 29, an upper region of the screen is used to present the carry map, and information indicating a swing temp, a head speed of a golf club, a numerical value indicating a carry distance, an inclination angle of a face of the golf club, a trajectory of a swing, an attack angle, and the like is presented in a lower region.

Figure 30:
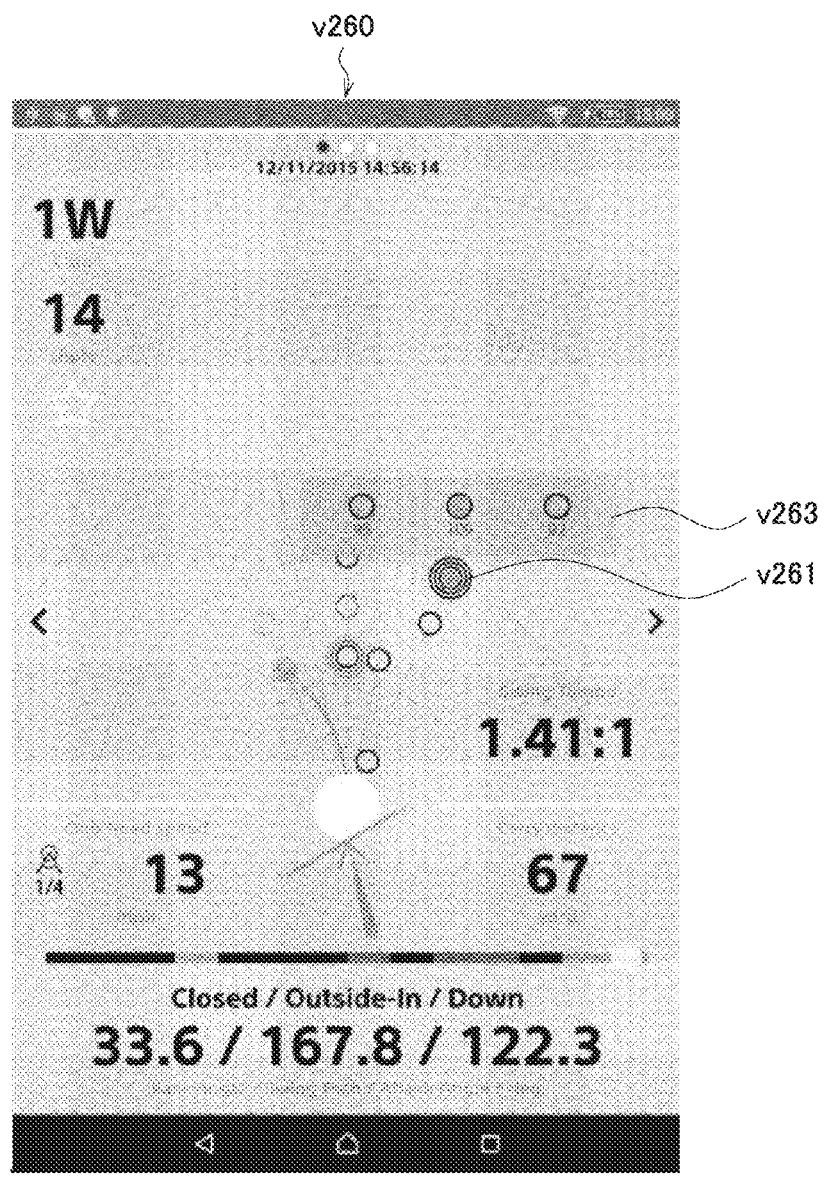
FIG. 30 is a diagram illustrating an example of a screen for suggesting a simulation result of a ball flight or a carry distance in the UI according to the embodiment.

In addition, a screen v260 illustrated in FIG. 30 shows an example of a case in which data for each shot is developed in a case in which there are a plurality of shots indicating that the simulation results of the carry distances are the same value in each direction in the example of the carry map illustrated in FIG. 29, as described with reference to FIG. 27. Specifically, a plot denoted by reference numeral v261 indicates that data equivalent to 3 shots is included. When this plot is selected through a tapping manipulation or the like, as denoted by reference numeral v263, a plot corresponding to each piece of data equivalent to 3 shots is presented to be developed in the horizontal direction. In addition, at this time, information indicating a shot number may be associated and presented in the plot corresponding to each shot. In addition, a plot corresponding to a shot registered as a favorite may be presented in a different display mode (for example, a different color) from plots corresponding to the other shots.

Figure 31:
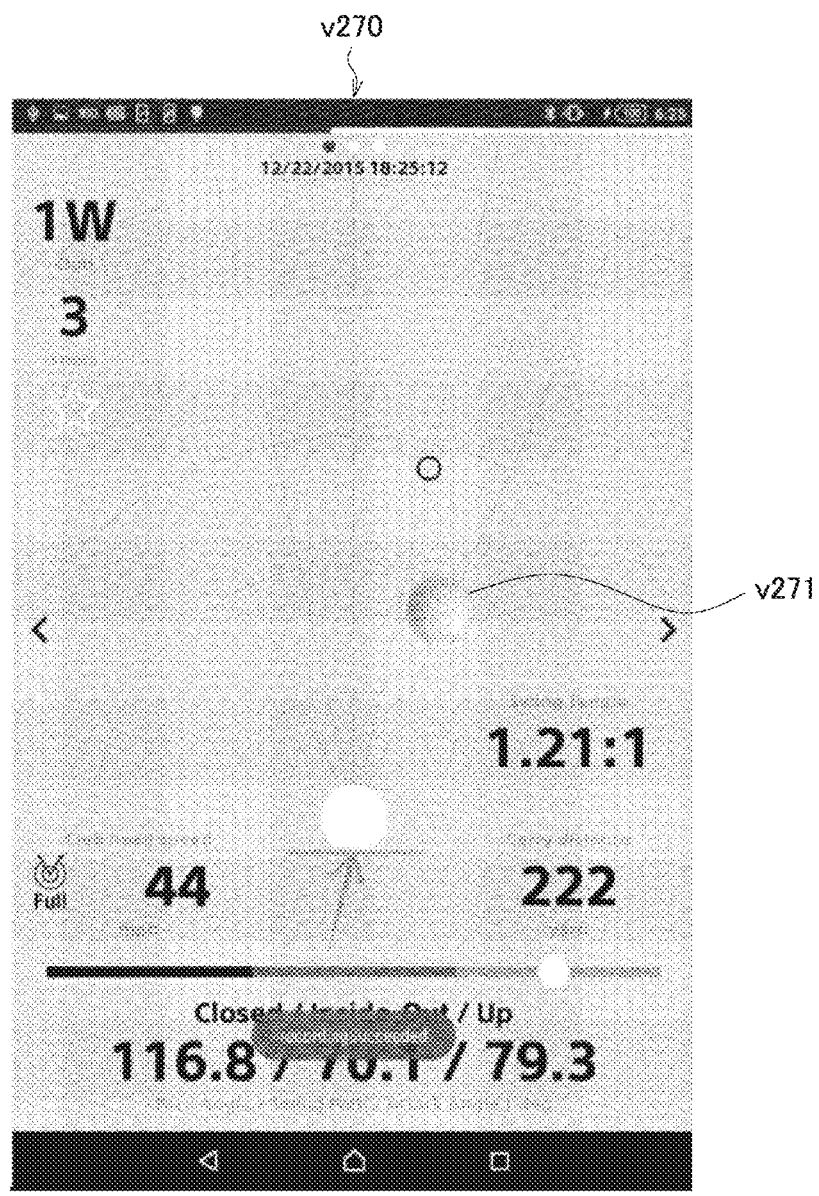
FIG. 31 is a diagram illustrating an example of a screen for suggesting a simulation result of a ball flight or a carry distance in the UI according to the embodiment.

In addition, a screen v270 illustrated in FIG. 31 shows an example of a presenting mode of a simulation result of a ball flight or a carry distance in the example of the carry map illustrated in FIG. 29. Specifically, in the example shown on the screen v270, in a case in which a desired plot is selected through a predetermined manipulation, as denoted by reference numeral v271, a simulation result of a ball flight or a carry distance corresponding to this plot is reproduced and presented as an animation. From this configuration, the user can intuitively recognize the simulation result of the ball flight or the carry distance.

The examples of the screens for simulating the ball flights or the carry distances on the basis of the sensing results by the body sensor device 100 or the shaft sensor device 200 and presenting simulation results have been described above with reference to FIGS. 23 to 31.

(6) Suggestion of Analysis Results of Swing Forms

Next, examples of screens for analyzing a swing form on the basis of a sensing result by the body sensor device 100 or the shaft sensor device 200 and presenting an analysis result will be described with reference to FIGS. 32 to 38. FIGS. 32 to 38 are diagrams illustrating examples of screens for presenting an analysis result of a swing form in the UI according to the embodiment.

Figure 32:
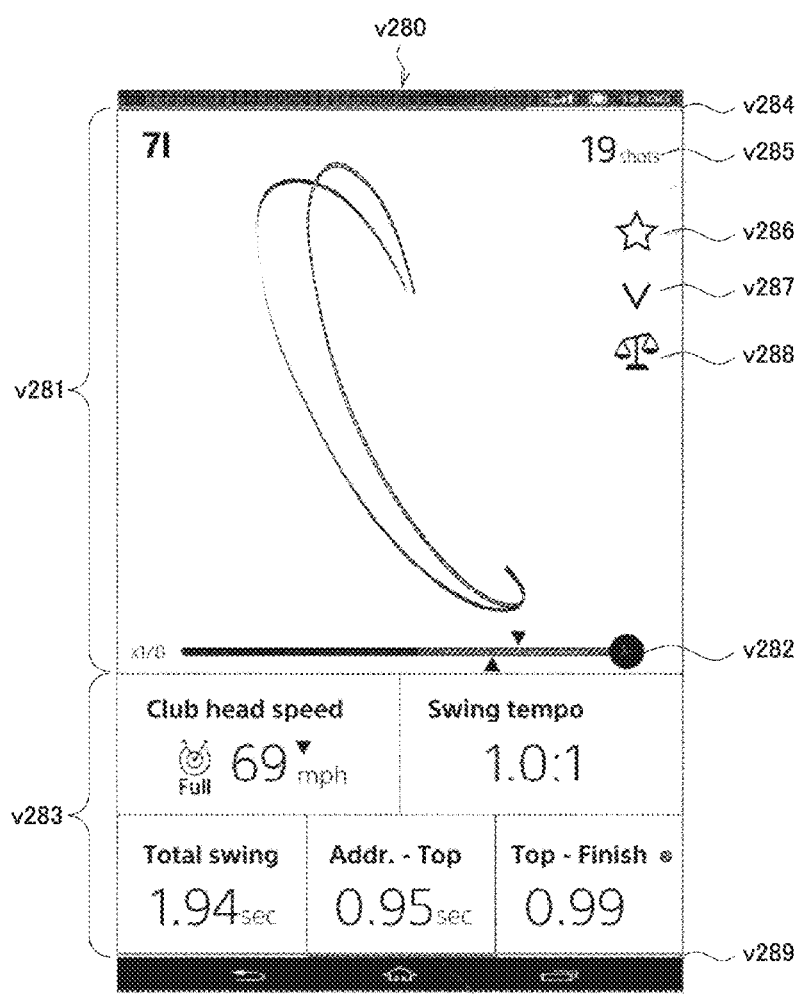
FIG. 32 is a diagram illustrating an example of a screen for suggesting a simulation result of a ball flight or a carry distance in the UI according to the embodiment.

For example, various kinds of information based on an analysis result of a swing are presented on a screen v280 illustrated in FIG. 32.

As a specific example, a trajectory (for example, a trajectory of a club head) of a swing calculated on the basis of a sensing result by the body sensor device 100 or the shaft sensor device 200 is presented to be visually identifiable as an image in a region denoted by reference numeral v281. In this case, the terminal device 500 calculates a change in a position or a direction of a part of a golf club chronologically on the basis of a sensing result of a movement of a part of the body (for example, the head) or a golf club by the body sensor device 100 or the shaft sensor device 200. Then, the terminal device 500 may visualize and present a calculation result of a change in the position or the direction of the part of the golf club chronologically as a trajectory. For example, in the example illustrated in FIG. 32, the calculation result of the change in the position of the head of the golf club at the time of a swing is presented as a 3-dimensional image in a region v281 by, for example, computer graphics (CG) or the like. In addition, the image indicating the trajectory of the swing presented in the region v281 may be presented to be rotatable 3-dimensionally on the basis of a manipulation such as tapping or dragging.

In addition, the image indicating the trajectory of the swing presented in the region v281 may be presented so that a chronological flow of the swing can be reproduced as a moving image (for example, an animation). As a specific example, when reproduction of the trajectory of the swing starts, the image indicating the trajectory of the swing may be presented as an animation extending chronologically from a start position to an end position of the swing. In addition, at this time, an input interface for controlling reproduction or stop of the moving image indicating the trajectory of the swing may be presented in the region v281. For example, in the example illustrated in FIG. 32, as denoted by reference numeral v282, a progress bar is presented as an input interface for controlling reproduction or stop of the moving image indicating the trajectory of the swing. In addition, a marker indicating a predetermined timing during the swing may be presented on the progress bar. For example, in the example illustrated in FIG. 32, an inverted triangular marker presented on the upper side of the progress bar indicates a timing at which a head speed of the golf club is a top speed. In addition, a triangular marker presented on the lower side of the progress bar indicates an impact timing.

In addition, in a region denoted by reference numeral v283, various kinds of information based on the analysis result of the swing are presented as numerical information. For example, in the example illustrated in FIG. 32, each of a "head speed of the golf club (Club head speed)," a "swing tempo (Swing tempo)," a "time necessary for the whole swing (Total swing)," a "time necessary from an address to a top (Addr.-Top)," and a "time taken from the top to end of the swing (Top-Finish)" is presented as numerical information.

In addition, for each piece of information presented in the region v283, a presenting timing may be controlled such that the presenting timing synchronizes with a timing of at least part of the series of flows of the swing. As a specific example, the "time necessary from an address to a top (Addr.-Top)" may be presented at a timing at which a back swing reaches the top. In addition, for the "time taken from the top to end of the swing (Top-Finish)" and the "swing tempo (Swing tempo)," a timing at which the swing ends may be presented.

In addition, a video (for example, a moving image of the swing) captured by a predetermined imaging unit may be presented along with an image indicating the trajectory of the swing presented in the region v281.

In addition, as denoted by reference numeral v285, information indicating the number of shots may also be presented. Note that, for example, a shot number corresponding to the information presented in the regions v281 and v283 may be presented as information v285 indicating the number of shots. In addition, as another example, the total number of shots for a period (for example, "Month," "Week," and "Day") which is a presenting target of information may be presented as the information v285 indicating the number of shots. In addition, the information v285 indicating the number of shots may be presented in a case in which a predetermined screen transitions to the screen v280 illustrated in FIG. 32. As a specific example, in a case in which information corresponding to data selected from a screen on which a list of data acquired previously and indicating analysis results or simulation results is presented as a history is presented as the screen v280, like the screen v200 illustrated in FIG. 26, the information v285 indicating the number of shots may be presented.

An icon denoted by reference numeral v286 is an input interface for selectively switching whether information presented on the screen v280 (that is, information indicating an analysis result of a swing) is registered as a "favorite." In addition, an icon denoted by reference numeral v287 is an input interface for selectively switching between display and non-display of a video (for example, a moving image of a swing) captured by the predetermined imaging unit. In addition, an icon denoted by reference numeral v288 is an input interface for calling a screen corresponding to a function of comparing information presented on the screen v280 (that is, information indicating an analysis result of a swing) with another information (that is, information indicating an analysis result of another swing). Note that the details of the comparison function will be separately described below.

In addition, a plurality of kinds of screens (for example, a screen for each golf club) may be selectively switched by a tab or the like on the screen v280. Therefore, for example, in the example illustrated in FIG. 32, a tab indicator indicating a displayed screen among a plurality of kinds of screens may be presented as denoted by reference numeral v289.

In addition, an indicator indicating an analysis preparation situation of a subsequent swing may be presented as denoted by reference numeral v284 on the screen v280.

Note that information presented as an analysis result of a swing on the screen v280 is not necessarily limited to only information based on the previously acquired data. As a specific example, the terminal device 500 may analyze a swing in real time on the basis of a sensing result acquired from the body sensor device 100 or the shaft sensor device 200 and may present various kinds of information on the screen v280.

In addition, the example of the screen described with reference to FIG. 32 and showing the analysis result of the swing is merely an example, and the type and the mode of the information displayed on the screen or positions at which various kinds of information are presented (that is, an layout of the screen) are not necessarily limited to the example described with reference to FIG. 32.

Figure 33:
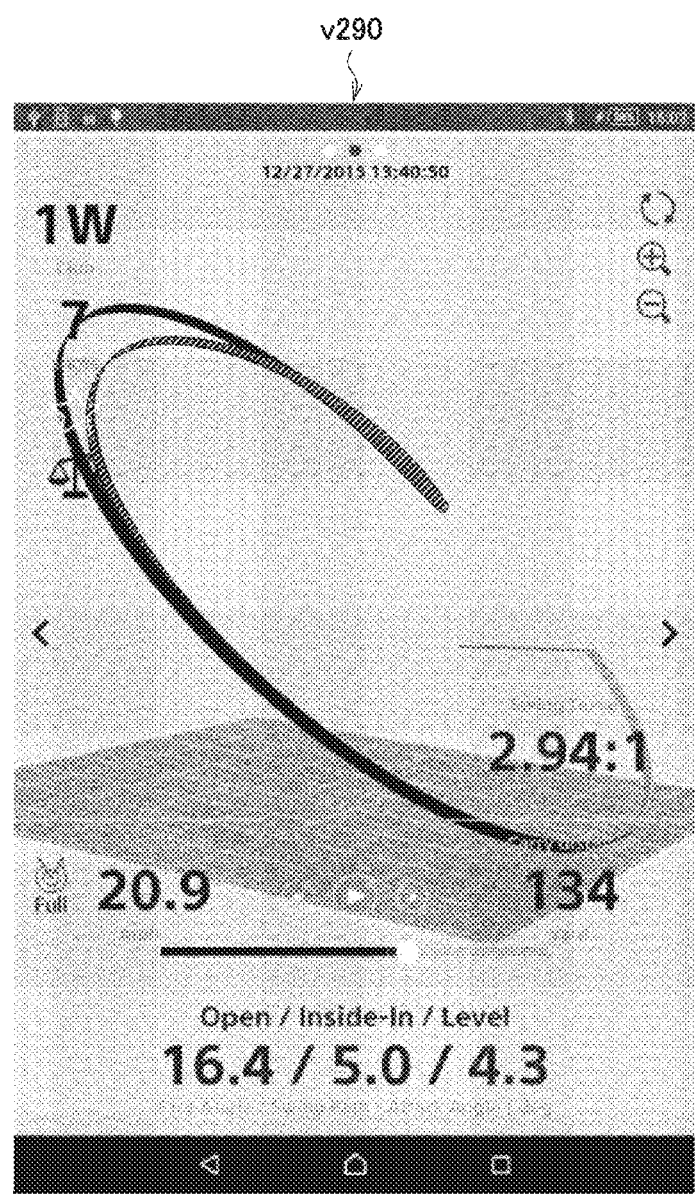
FIG. 33 is a diagram illustrating an example of a screen for suggesting a simulation result of a ball flight or a carry distance in the UI according to the embodiment.

For example, a screen v290 illustrated in FIG. 33 is another example of the screen on which an analysis result of a swing is presented. On the screen v290 illustrated in FIG. 33, a region on the upper side of the screen is used to present an image indicating a trajectory of a swing, and information indicating a swing temp, a head speed of a golf club, a numerical value indicating a carry distance, an inclination angle of a face of the golf club, a trajectory of a swing, an attack angle, and the like is presented in a lower region.

Figure 34:
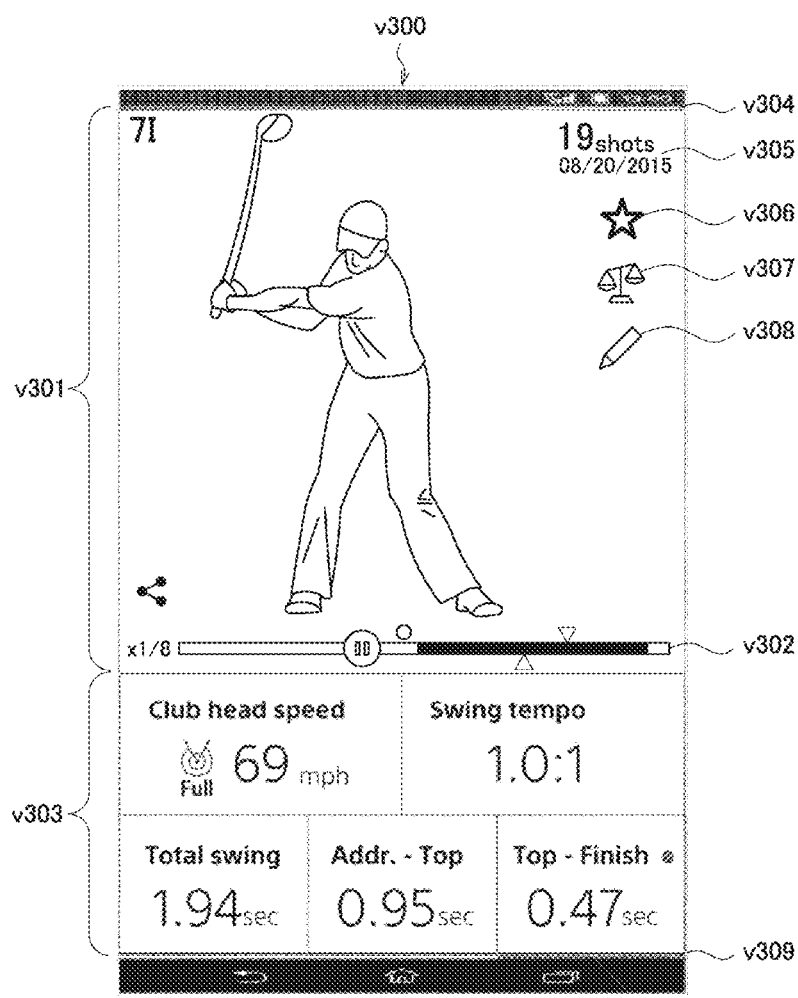
FIG. 34 is a diagram illustrating an example of a screen for suggesting a simulation result of a ball flight or a carry distance in the UI according to the embodiment.

A screen v300 illustrated in FIG. 34 shows an example of a case in which a video (for example, a moving image of a swing) captured by a predetermined imaging unit is presented along with information indicating an analysis result of a swing. As a specific example, on the screen v300, an image is switched to an image indicating a trajectory of a swing presented in the region v281 on the screen v280 illustrated in FIG. 32, and a moving image of a swing captured by a predetermined imaging unit is presented in a region denoted by reference numeral v301. Note that on the screen v300, information presented in a region denoted by reference numeral v303 is the same as information presented in a region shown as the region v283 on the screen v280 illustrated in FIG. 32.

In addition, the progress bar denoted by reference numeral v302 is an input interface for controlling reproduction or stop of the moving image presented in the region v301. In the progress bar v302, for example, a marker indicating a timing at which a head speed of a golf club is a top speed or a marker indicating an impact timing may also be presented, like the progress bar v282 described with reference to FIG. 32.

Since various kinds of information denoted by reference numerals v304, v305, v306, v307, and v309 are the same as the information denoted by reference numerals v284, v285, v286, v288, and v289 in the example illustrated in FIG. 32, the detailed description thereof will be omitted.

In addition, for example, a function of associating various kinds of information with a moving image presented in the region v301 through a predetermined manipulation by the user may be installed on the screen v300. As a specific example, an icon denoted by reference numeral v308 is an input interface for activating a so-called drawing tool for writing information by hand in the moving image presented in the region v301.

Note that the moving image of the swing presented on the screen v300 is not necessarily limited to only a previously recorded moving image. As a specific example, the terminal device 500 may present an image captured by a predetermined imaging unit in real time in the region v301 of the screen v300. Note that at this time, the terminal device 500 may present a moving image transmitted from an external imaging device in the region v301. In addition, at this time, the terminal device 500 may analyze a swing in real time on the basis of a sensing result acquired from the body sensor device 100 or the shaft sensor device 200 and may present various kinds of information based on the analysis result in the region v303.

In addition, the example of the screen which is described with reference to FIG. 34 and on which the moving image of the swing captured by the predetermined imaging unit is presented is merely an example, and the type and the mode of the information displayed on the screen or positions at which various kinds of information are presented (that is, an layout of the screen) are not necessarily limited to the example described with reference to FIG. 34.

Figure 35:
FIG. 35 is a diagram illustrating an example of a screen for suggesting a simulation result of a ball flight or a carry distance in the UI according to the embodiment.

For example, a screen v310 illustrated in FIG. 35 shows another example of a screen on which a moving image of a swing captured by a predetermined imaging unit is presented. On the screen v310 illustrated in FIG. 35, a region on the upper side of the screen is used to present a video (that is, a moving image of a swing) captured by a predetermined imaging unit, and information indicating a swing tempo, a head speed of a golf club, a numerical value indicating a carry distance, an inclination angle of a face of the golf club, a trajectory of a swing, an attack angle, and the like is presented in a lower region.

Figure 36:
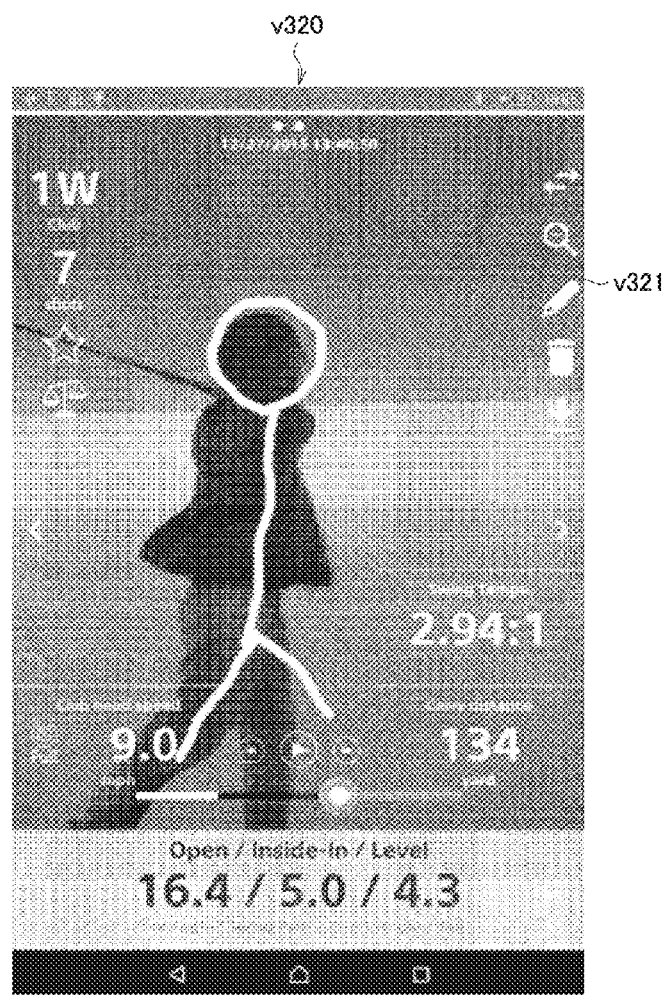
FIG. 36 is a diagram illustrating an example of a screen for suggesting a simulation result of a ball flight or a carry distance in the UI according to the embodiment.

In addition, a screen v320 illustrated in FIG. 36 shows an example of a case in which information is additionally written in the presented moving image by hand using a so-called drawing tool on the screen v310 illustrated in FIG. 35. Specifically, the user can additionally write desired information by hand so that the desired information is superimposed on the presented video of the swing by manipulating an icon denoted by reference numeral v321 to active the drawing tool and trace a line on the screen with a manipulator such as a finger.

Next, examples of progress bars used to manipulate reproduction or stop of various moving images, like the progress bar v282 described with reference to FIG. 32 and the progress bar v302 described with reference to FIG. 34, will be described in more detail with reference to FIGS. 37 and 38. Note that in the description, each of progress bars v331a to v331f illustrated in FIGS. 37 and 38 is simply referred to as "progress bars v331" in some cases in a case in which the progress bars v331a to v331f are generally indicated.

Figure 37:
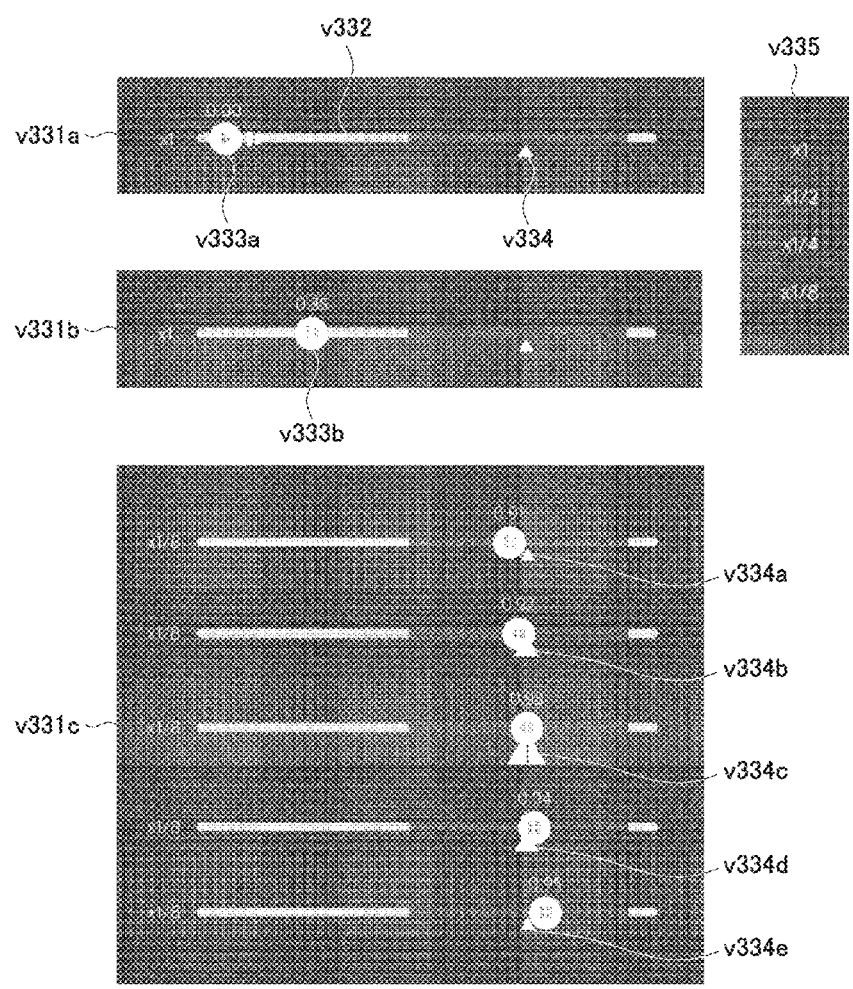
FIG. 37 is a diagram illustrating an example of a screen for suggesting a simulation result of a ball flight or a carry distance in the UI according to the embodiment.
Figure 38:
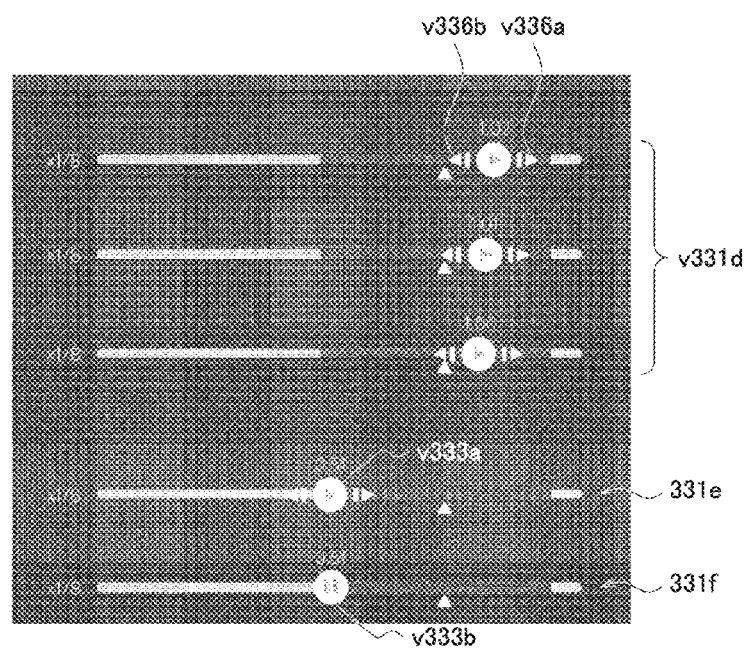
FIG. 38 is a diagram illustrating an example of a screen for suggesting a simulation result of a ball flight or a carry distance in the UI according to the embodiment.

For example, in FIG. 37, reference numeral v331a denotes a state of the progress bar v331 during temporary stop of a moving image and reference numeral v331b denotes a state of the progress bar v331 during reproduction of the moving image. As illustrated in FIG. 37, in the progress bar v331, a position of an icon in the horizontal direction presented on a bar denoted by reference numeral v332 corresponds to a position (that is, a reproduction time) of a moving image to be reproduced on a time axis. Note that, as denoted by reference numeral v331a, an icon v333a with a reproduction mark is presented as an icon presented on the bar v332 during temporary stop of the moving image. That is, the reproduction of the moving image starts when the icon v333a is manipulated. In addition, as denoted by reference numeral v331b, an icon v333b with a temporary stop mark is presented as an icon presented on the bar v332 during the reproduction of the moving image. That is, the reproduction of the moving image temporarily stops when the icon v333b is manipulated. Note that in the following description, the icons v333a and v333b are simply referred to as "icons v333" in some cases in a case in which the icons v333a and v333b are not particularly distinguished from each other.

In addition, a reproduction speed of a moving image may be selectively switched. For example, as denoted by reference numeral v335, an input interface for designating a reproduction speed of a moving image may be installed. As a more specific example, in the example illustrated in FIG. 37, one of "×1," "×½," "×¼," and "×⅛" can be selected as a reproduction speed.

In addition, the bar v332 may be presented so that each course (for example, a takeback, a top, a downswing, an impact, follow, and a finish) in a series of swing movements can be identified by a difference in a display mode. For example, in the example illustrated in FIG. 37, an impact timing is shown by presenting a marker denoted by reference numeral v334. In addition, in the example illustrated in FIG. 37, a portion corresponding to a period before and after the impact timing is presented with a different color from portions corresponding to other periods in the bar v332 so that the period is further emphasized In addition, a display mode may be controlled such that the marker v334 is further emphasized and displayed as the reproduction time of the moving image is closer to the impact timing. For example, in an example denoted by reference numeral v331c, the display mode of the marker v334 is controlled such that the size of the marker v334 is further expanded as the reproduction time of the moving image is closer to the impact timing. Specifically, a state denoted by reference numeral v334c is a state in which the reproduction time substantially matches the impact timing. That is, the size of the marker v334 is controlled such that the size of the marker v334 is further expanded as the reproduction time of the moving image is closer to the impact timing, as denoted by reference numerals v334c to v334c. Then, when the reproduction time of the moving image passes through the impact timing, the size of the marker v334 is controlled such that the size of the marker v334 is further contracted as the reproduction time progresses, as denoted by reference numeral v334c to v334e.

In addition, in a state in which the reproduction of the moving image is temporarily stopped, as denoted by reference numeral v331d in FIG. 38, an input interface for frame-by-frame playback of the moving image may be displayed, as denoted by reference numerals v336a and v336. Specifically, an icon denoted by reference numeral v336a is an input interface for moving a reproduction time of the moving image in a chronological direction by a predetermined number of frames (for example, one frame) (that is, frame-by-frame playback in the chronological direction). In addition, an icon denoted by reference numeral v336b is an input interface for moving the reproduction time of the moving image in the opposite direction to the chronological direction by a predetermined number of frames (for example, one frame) (that is, frame-by-frame playback in the opposite direction to the chronological direction).

In addition, on the progress bar v331, the reproduction time of the moving image can also be explicitly designated by dragging the icon v333. Note that in a case in which a dragging manipulation is performed on the icon v333a in a state in which the moving image is temporarily stopped, as denoted by reference numeral v331e, the state of the progress bar v331 after the manipulation may be controlled such that the moving image is temporarily stopped. Similarly, in a case in which a dragging manipulation is performed on the icon v333b in a state in which the moving image is reproduced, as denoted by reference numeral v331f, the state of the progress bar v331 after the manipulation may also be controlled such that the moving image is being reproduced.

The examples of the screens for analyzing the swing form on the basis of the sensing result by the body sensor device 100 or the shaft sensor device 200 and presenting the analysis result has been described above with reference to FIGS. 32 to 38.

(7) Comparison of Swing Forms

Next, examples of screens for comparing analysis results of swing forms corresponding to mutually different shots will be described with reference to FIGS. 39 to 44. First, examples of screens for comparing moving images of swings captured by a predetermined imaging unit between mutually different shots will be described with reference to FIGS. 39 to 42. FIGS. 39 to 42 are diagrams illustrating examples of screens for comparing moving images of swings between mutually different shots in the UI according to the embodiment.

Figure 39:
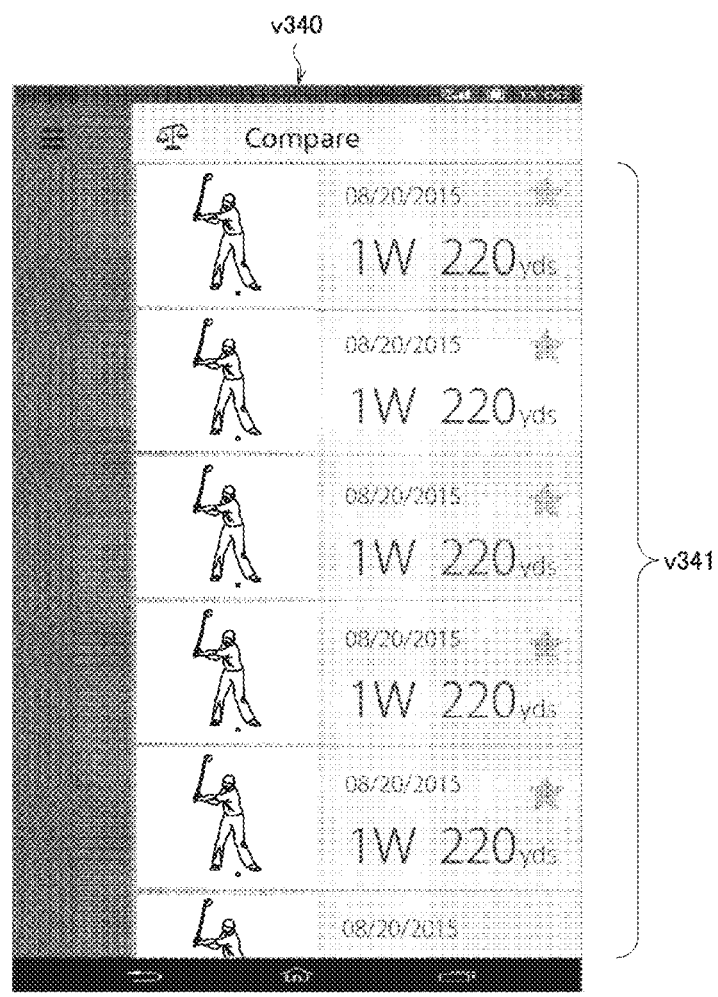
FIG. 39 is a diagram illustrating an example of a screen for comparing moving images of swings between mutually different shots in the UI according to the embodiment.

For example, a screen v340 illustrated in FIG. 39 is an example of a screen for selecting data which is a comparison source and a comparison target. Specifically, on the screen v340, a list of data indicating previously acquired analysis results or simulation results is presented in a region denoted by reference numeral v341. Note that a part of information corresponding to each piece of data is presented in each item of the list. As a specific example, in the item corresponding to each piece of data, information regarding at least a part of a date on which the data is acquired, information regarding setting related to analysis or simulation, such as a golf club number used in a practice of a swing, information corresponding to an analysis result or a simulation result, and the like is presented. In addition, in the item corresponding to each piece of data, a thumbnail of a moving image associated with the data may be presented. On the basis of this configuration, the user may select items corresponding to the data which is the comparison source and the comparison target in the list presented in the region v341 on the basis of a predetermined manipulation such as a tapping manipulation.

Figure 40:
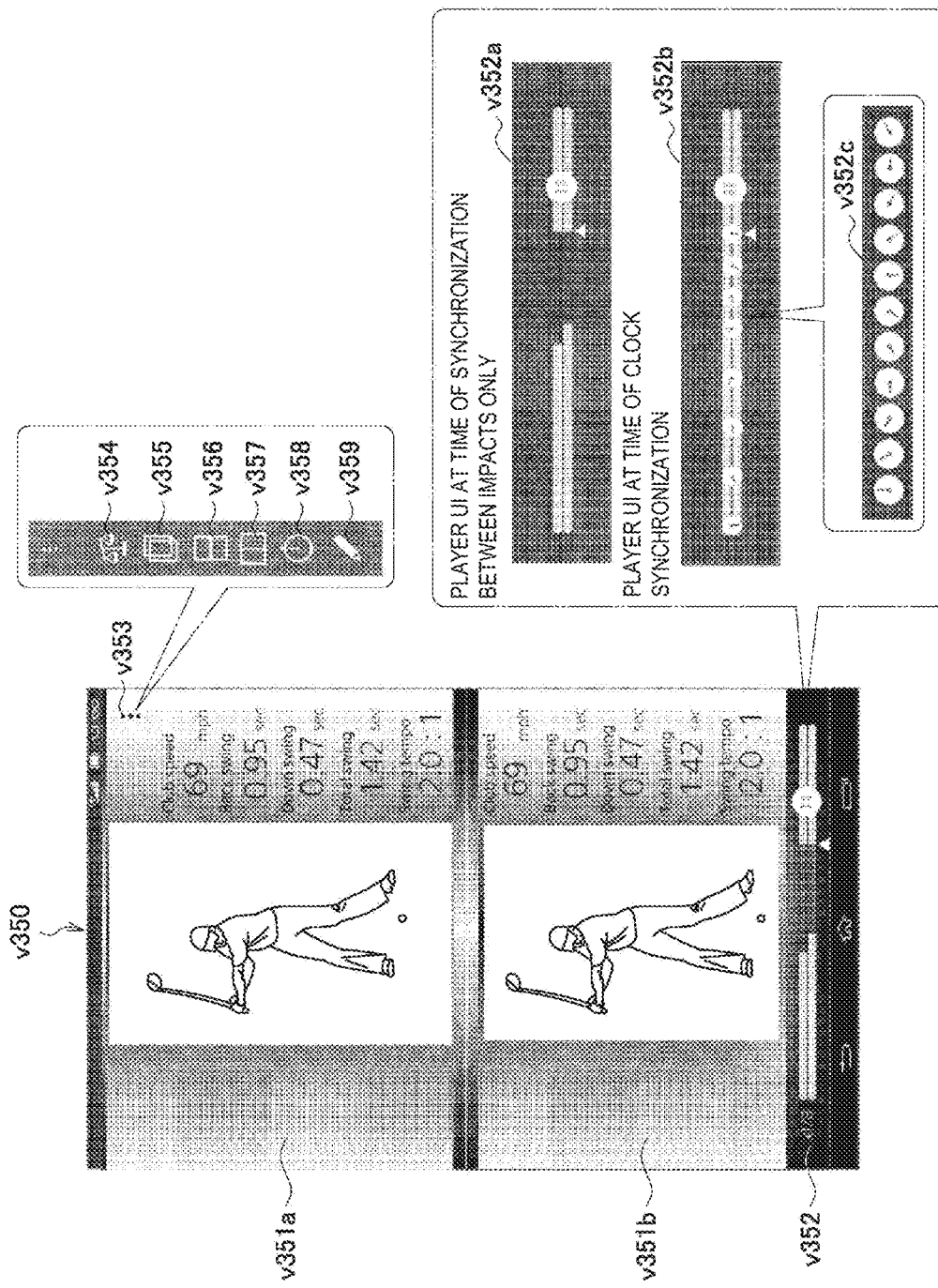
FIG. 40 is a diagram illustrating an example of a screen for comparing moving images of swings between mutually different shots in the UI according to the embodiment.

A screen v350 illustrated in FIG. 40 is an example of a screen on which a moving image which is the comparison source and a moving image which is the comparison target are presented so that the moving images can be compared by displaying the moving images side by side in the vertical direction. Specifically, the moving image selected as the comparison source is displayed in a region denoted by reference numeral v351a. In addition, the moving image selected as the comparison target is displayed in a region denoted by reference numeral v351b. In addition, as denoted by reference numeral v352, a progress bar for manipulating reproduction or stop of each moving image is presented so that the moving image which is the comparison source is synchronized with the moving image which is the comparison target. In addition, a marker indicating an impact timing of a swing presented on the moving image of each of the comparison source and the comparison target is presented in the progress bar v352.

Note that as a comparison method of a case in which a moving image of a swing is compared between mutually different shots, for example, a "method of synchronizing only impacts" and a "method of performing clock synchronization" can be exemplified.

For example, a progress bar denoted by reference numeral v352a is an example of a progress bar presented in a case in which both the moving images of the comparison source and the comparison target are synchronized and reproduced on the basis of a method of synchronizing only impacts. In a case in which only the impacts are synchronized, reproduction timings of the moving images are controlled such that impact timings in swings of both the moving images of the comparison source and the comparison target match each other. Note that in this case, reproduction speeds of images match each other.

In addition, as another example, a progress bar denoted by reference numeral v352b is an example of a progress bar presented in a case in which both the moving images of the comparison source and the comparison target are synchronized and reproduced on the basis of clock synchronizing method. As the clock synchronization, a reproduction timing or a reproduction speed of the moving image of at least one of the comparison source and the comparison target is controlled such that series of swing actions are substantially synchronized between both the moving images of the comparison source and the comparison target.

More specifically, start timings or swing speeds of the swings may not necessarily match each other between mutually different shots. Therefore, when reproduction speeds of the moving images of both the comparison source and the comparison target are matched to each other, angles of golf clubs may not necessarily be matched to each other at different timings although the angles of the golf clubs at the time of swings are matched to each other at a certain timing. Thus, as the clock synchronization, a reproduction timing or a reproduction speed of at least one moving image is controlled such that the angles of the golf clubs are substantially matched to each other at each of a plurality of timings in a series of swing actions between the moving images of both the comparison source and the comparison target (furthermore, the angles of the golf clubs in a series of flows are normally substantially matched to each other). Note that in each icon denoted by the progress bar v352b and resembling a hand of a clock, an angle indicated by the hand of the clock indicates an angle of the shaft of a golf club at the time of a swing.

By using the clock synchronization, it is possible to reproduce the moving images of both the comparison source and the comparison target so that a series of swing actions is synchronized between shots at which swing speeds are different. Therefore, it is possible to compare a series of flows of a swing form between the shots at which the swing speeds are different.

An icon denoted by reference numeral v353 is an input interface for displaying a menu in which icons for performing various functions are presented. As the icons presented as the menu, for example, icons denoted by reference numerals v354 to v359 can be exemplified.

Specifically, the icon v354 is an input interface for supporting cancellation of the comparison of the moving images between the mutually different shots.

In addition, icons v355 to v357 are input interfaces for designating a comparison method in a case in which moving images are compared between mutually different shots. Specifically, the icon v355 is an input interface for selecting a method of comparing moving images between mutually different shots by superimposing one moving image on the other moving image. In addition, the icon v356 is an input interface for arranging moving images respectively corresponding to the mutually different shots in the vertical direction and selecting a method of comparing moving images between the shots. In addition, the icon v357 is an input interface for selecting a method of comparing moving images between the shots by arranging the moving images respectively corresponding to the mutually different shots in the horizontal direction.

In addition, the icon v358 is an input interface for selecting a method of comparing moving images between mutually different shots. Note that as the method comparing moving images, for example, the "method of synchronizing only impacts" and the "method of performing clock synchronization" described above can be exemplified. In addition, the icon v359 is an input interface for activating a so-called drawing tool for writing information by hand on a presented moving image.

Figure 41:
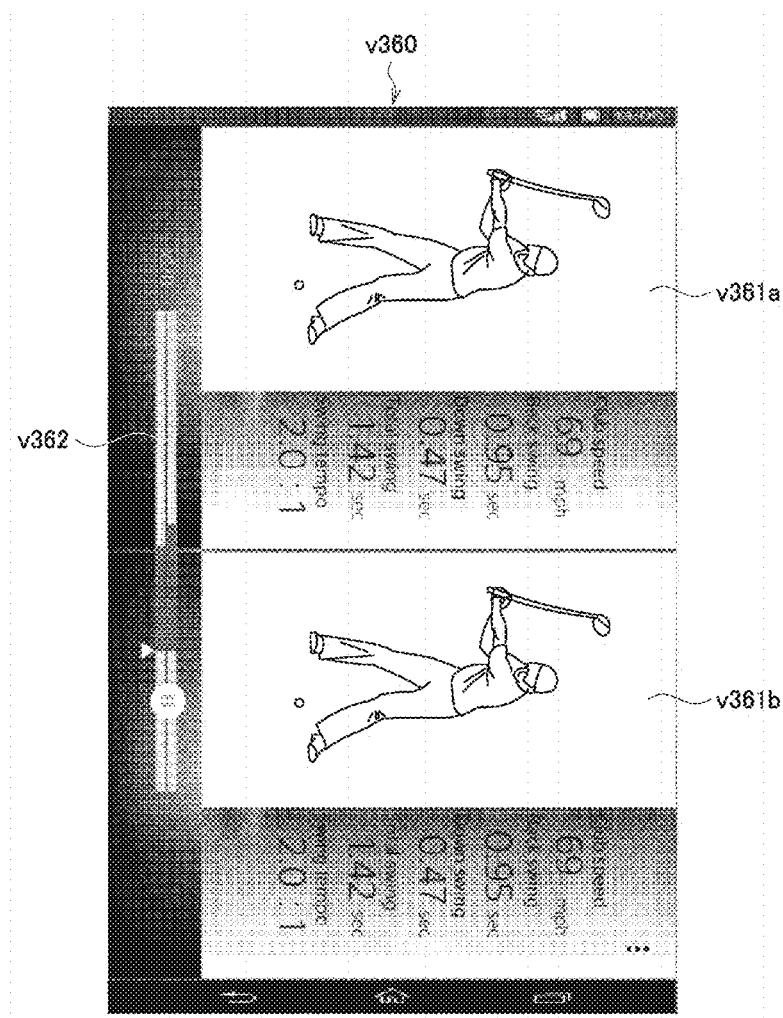
FIG. 41 is a diagram illustrating an example of a screen for comparing moving images of swings between mutually different shots in the UI according to the embodiment.

In addition, as another example, a screen v360 illustrated in FIG. 41 is an example of a screen on which a moving image which is the comparison source and a moving image which is the comparison target are presented to be comparable by displaying the moving images side by side in the vertical direction. Specifically, the moving image selected as the comparison source is displayed in a region denoted by reference numeral v361a. In addition, the moving image selected as the comparison target is displayed in a region denoted by reference numeral v361b. In addition, as denoted by reference numeral v362, a progress bar for manipulating reproduction or stop of each moving image is presented so that the moving image which is the comparison source is synchronized with the moving image which is the comparison target. The progress bar v362 is the same as the progress bar v352 described with reference to FIG. 40.

In addition, like the screen v350 described with reference to FIG. 40, one of a "method of synchronizing only impacts" and a "method of performing clock synchronization" can also be selected as a method of comparing moving images to each other even in the screen v360. Therefore, in accordance with the method of comparing the moving images between different shots, an input interface (for example, the progress bars v352a and v352b illustrated in FIG. 40) in accordance with the synchronization method may be presented as the progress bar v362.

Figure 42:
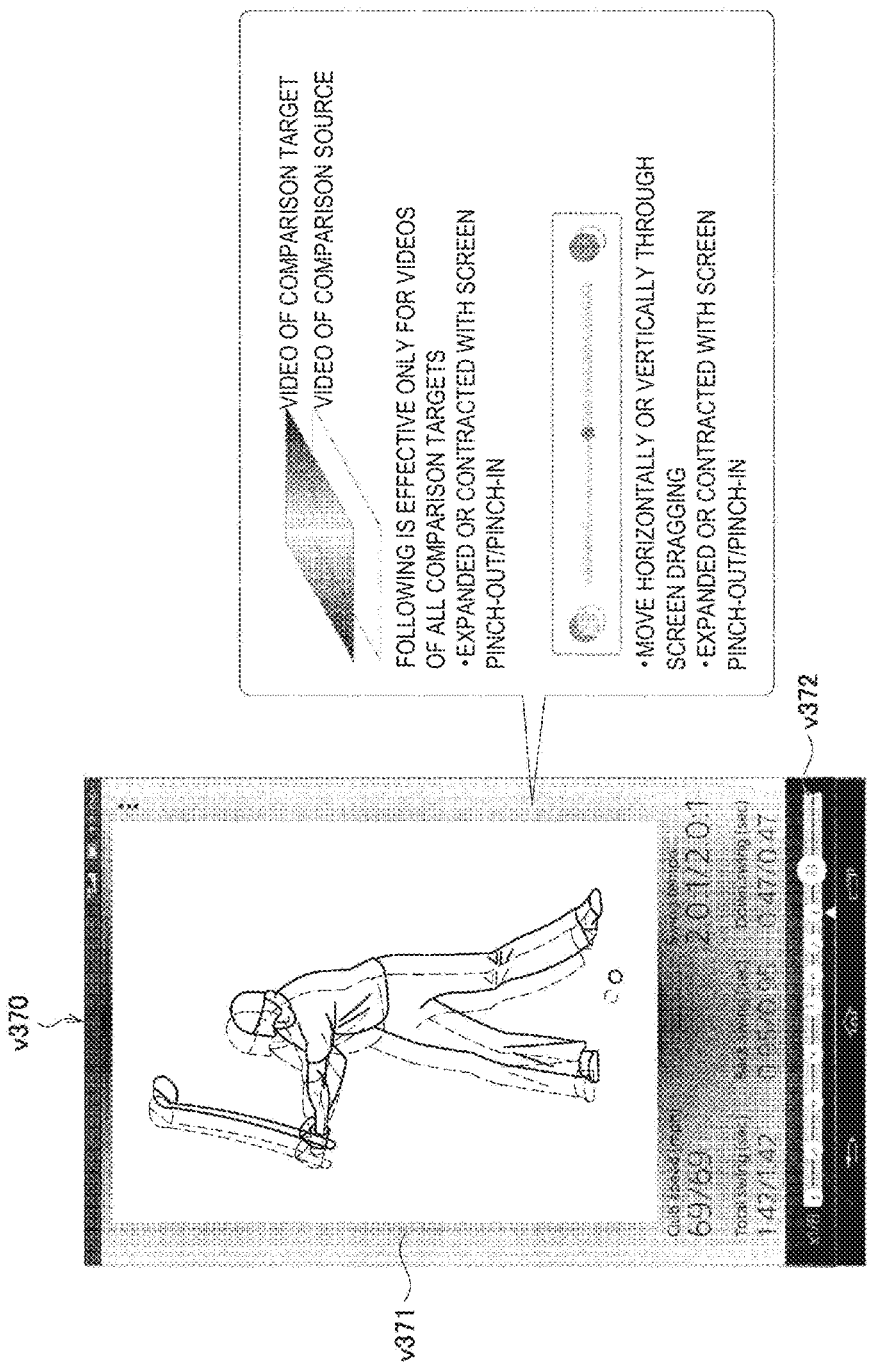
FIG. 42 is a diagram illustrating an example of a screen for comparing moving images of swings between mutually different shots in the UI according to the embodiment.

In addition, as another example, a screen v370 illustrated in FIG. 42 is an example of a screen on which moving images are presented to be comparable by superimposing one of a moving image which is a comparison source and a moving image which is a comparison target on the other method. For example, in the example illustrated in FIG. 42, the moving image which is the comparison target presented translucently is displayed to be superimposed on the moving image which is the comparison source in a region denoted by reference number v371 so that the moving images are reproduced to be synchronized with each other. At this time, as a method of synchronizing the moving images, the "method of synchronizing only impacts" and the "method of performing clock synchronization" can be selected, like the screen v350 illustrated in FIG. 40. In addition, as denoted by reference numeral v372, a progress bar corresponding to a synchronization method is displayed in accordance with the synchronization method between the selected moving images. For example, in the example illustrated in FIG. 42, the "method of performing clock synchronization" is selected and the progress bar is presented in accordance with the synchronization method.

In addition, for a moving image presented in the region v371, a presenting mode can also be controlled on the basis of a user manipulation. As a specific example, display positions of the moving images of the comparison source and the comparison target can be changed through a manipulation such as dragging. In addition, display sizes of the moving images of the comparison source and the comparison target can also be adjusted (expanded or contracted) through a manipulation such as pinch-out, pinch-in, and the like. In addition, transparency of the moving image of the comparison target superimposed on the moving image of the comparison source may also be changeable by manipulating a predetermined input interface. Note that an input interface for adjusting the transparency of the moving image of the comparison target may be presented through a predetermined manipulation (for example, a tapping manipulation on the screen).

In addition, a function of comparing different pieces of data between different shots may be installed without being limited to the moving images. For example, FIGS. 43 and 44 are diagrams illustrating examples of screens for comparing trajectories of swings between mutually different shots in the UI according to the embodiment.

Figure 43:
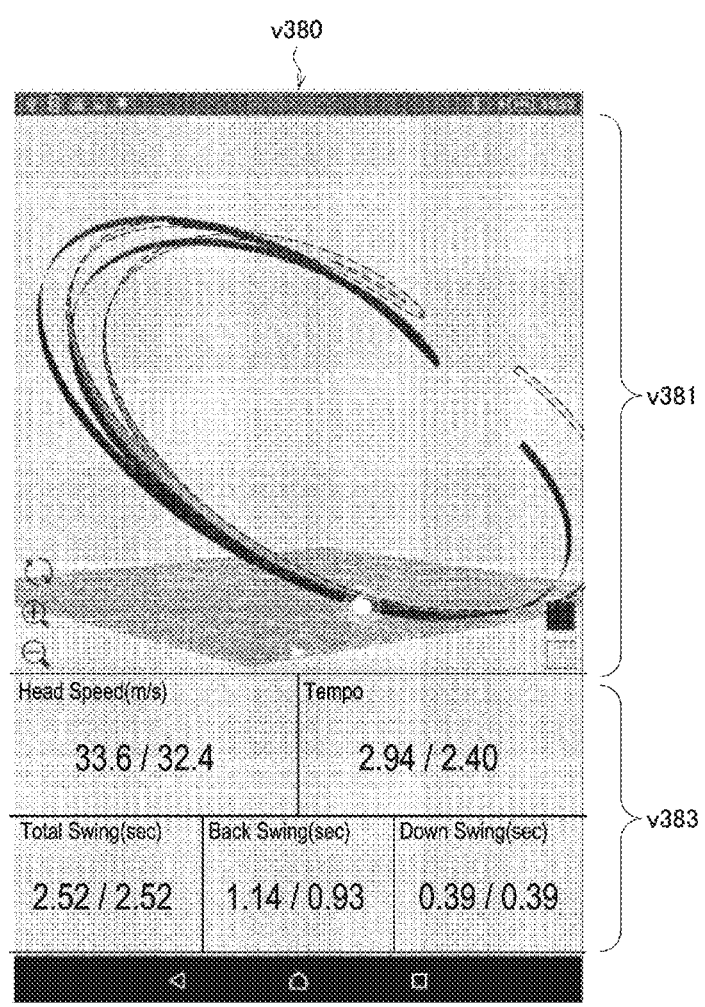
FIG. 43 is a diagram illustrating an example of a screen for comparing trajectories of swings between mutually different shots in the UI according to the embodiment.
Figure 44:
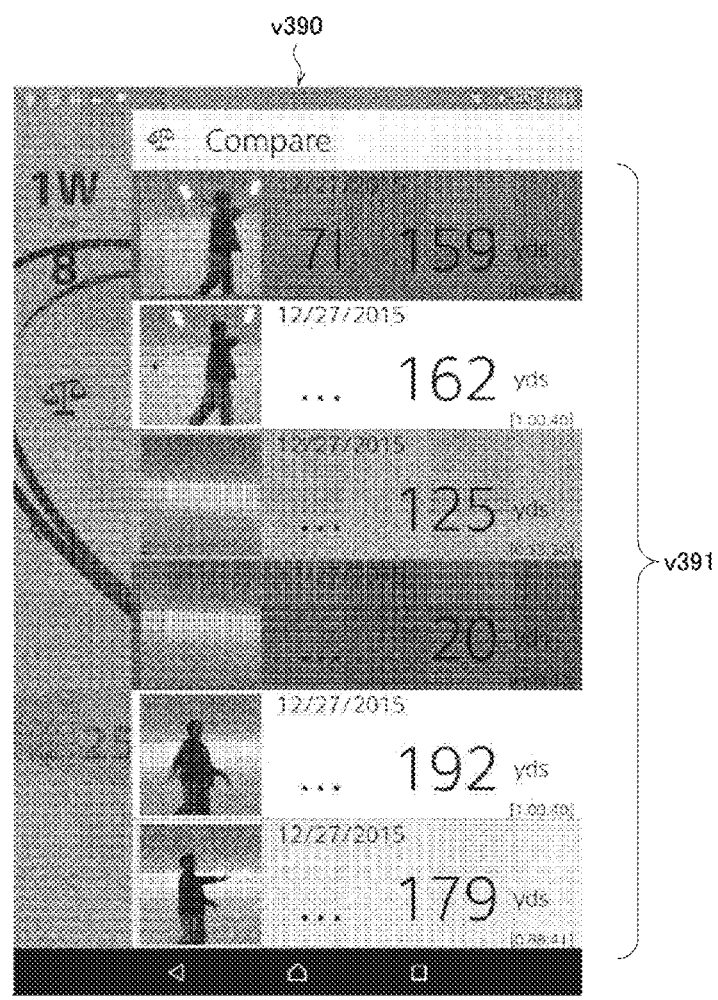
FIG. 44 is a diagram illustrating an example of a screen for comparing trajectories of swings between mutually different shots in the UI according to the embodiment.

Specifically, a screen v380 illustrated in FIG. 43 is an example of a screen on which analysis results of swings (for example, images indicating trajectories of swings) described with reference to FIG. 32 are compared between different shots. Specifically, images respectively corresponding to shots selected as the comparison source and the comparison target and indicating the trajectories of the swings are presented to be superimposed in a region denoted by reference numeral v383. In addition, in the example illustrated in FIG. 43, the images respectively corresponding to the comparison source and the comparison target and indicating the trajectories of the swings are presented with mutually different colors. Thus, the user can intuitively determine the images respectively corresponding to the comparison source and the comparison target and indicating the trajectories of the swings.

In addition, in the region denoted by reference numeral v383, various kinds of information based on analysis results of the swings are presented as numerical information. For example, in the example illustrated in FIG. 43, each of a "head speed of a golf club (Head speed)," a "swing tempo (Tempo)," a "time necessary for the whole swing (Total swing)," a "time necessary for a back swing (Back Swing)," and a "time necessary for a down swing (Down Swing)" is presented as numerical information.

In addition, like the screen v340 on which the data which is the comparison source and the comparison target of the moving images are selected, as described with reference to FIG. 39, a screen for selecting data which is the comparison source and the comparison target may also be installed for a function of comparing analysis results of swings. For example, a screen v390 illustrated in FIG. 44 is an example of a screen for selecting data which is a comparison source and a comparison target. Specifically, on the screen v390, a list of data indicating previously acquired analysis results or simulation results is presented in a region denoted by reference numeral v391. Note that a part of information corresponding to each piece of data is presented in each item of the list. As a specific example, in the item corresponding to each piece of data, information regarding at least a part of a date on which the data is acquired, information regarding setting related to analysis or simulation, such as a golf club number used in a practice of a swing, information corresponding to an analysis result or a simulation result, and the like is presented. In addition, a thumbnail corresponding to the data may be presented in the item corresponding to each piece of data. For example, in the example illustrated in FIG. 44, a thumbnail of a moving image associated with each piece of data is presented as the thumbnail. On the basis of this configuration, the user may select items corresponding to the data which is the comparison source and the comparison target in the list presented in the region v341 on the basis of a predetermined manipulation such as a tapping manipulation.

The examples of the screens for comparing the analysis results of the swing forms corresponding to the mutually different shots have been described above with reference to FIGS. 39 to 44.

(8) Customization of Screen

Figure 45:
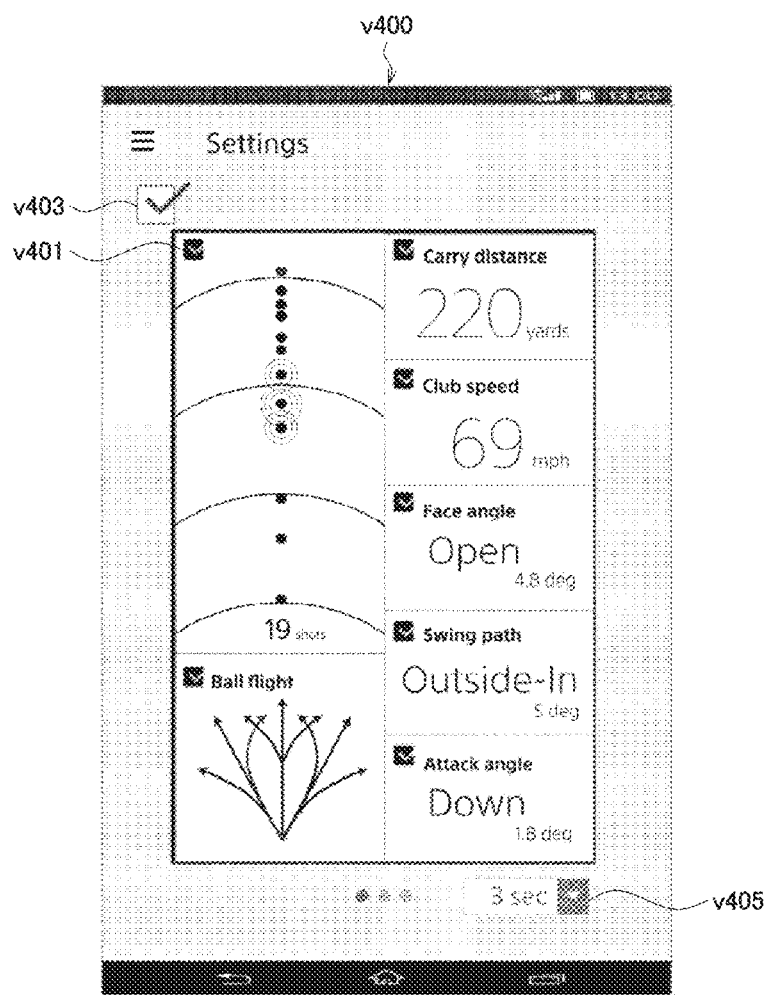
FIG. 45 is a diagram illustrating an example of a screen for changing setting of a display mode of each screen in the UI according to the embodiment.
Figure 46:
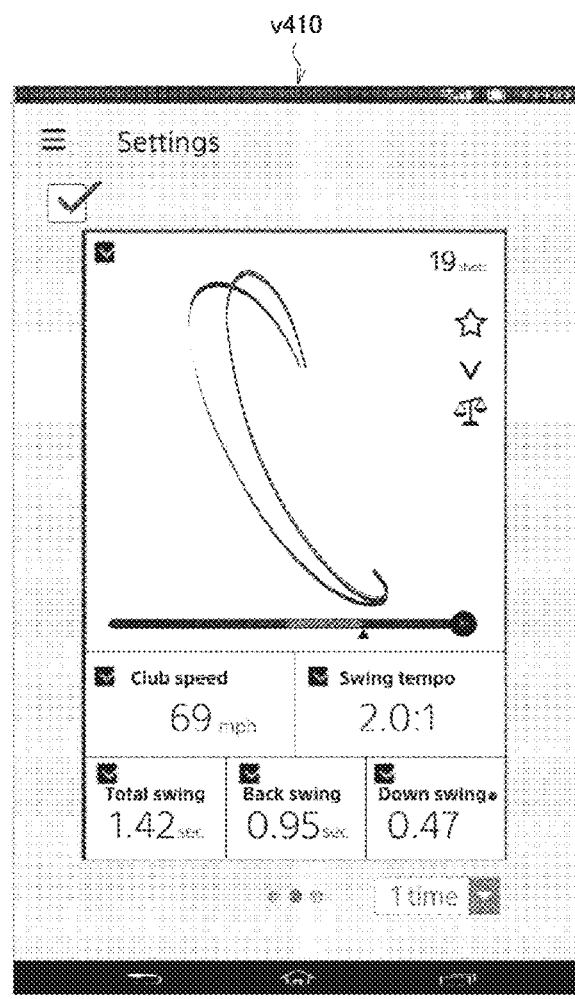
FIG. 46 is a diagram illustrating an example of a screen for changing setting of a display mode of each screen in the UI according to the embodiment.
Figure 47:
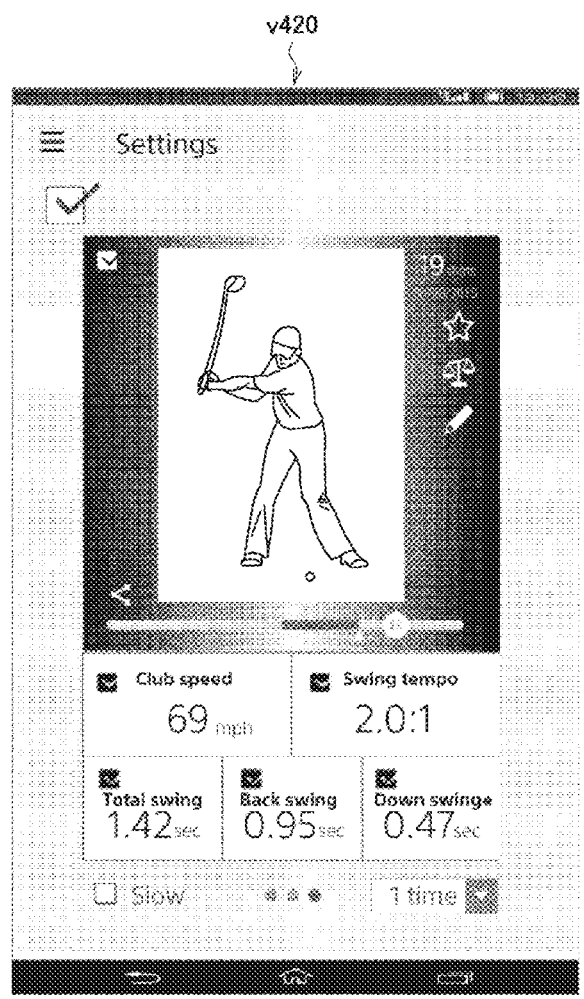
FIG. 47 is a diagram illustrating an example of a screen for changing setting of a display mode of each screen in the UI according to the embodiment.

Next, examples of setting screens for customizing information displayed on screens in each screen will be described with reference to FIGS. 45 to 47. FIGS. 45 to 47 are diagrams illustrating examples of screens for changing setting of a display mode of each screen in the UI according to the embodiment.

For example, a screen v400 illustrated in FIG. 45 is an example of a setting screen for customizing information displayed on the screen v180 described with reference to FIG. 23. As denoted by reference numeral v401, a check box is presented to be associated with each item corresponding to each piece of information. Thus, by switching between display and non-display of a check mark in the check box corresponding to each item through a predetermined manipulation, it is possible to control the display and non-display of the item. In addition, as denoted by reference numeral v403, a check box for switching between display and non-display may be installed for all the items on the screen. In addition, as denoted by reference numeral v405, an input interface for setting a display unit of information displayed on a corresponding screen may be installed.

In addition, a screen v410 illustrated in FIG. 46 is an example of a setting screen for customizing information displayed on the screen v280 described with reference to FIG. 32. Similarly, a screen v420 illustrated in FIG. 47 is an example of a setting screen for customizing information displayed on the screen v300 described with reference to FIG. 34.

The examples of the setting screens for customizing the information displayed on the screens in each screen have been described with reference to FIGS. 45 to 47.

(9) Selection of Data Registered as Favorite

Figure 48:
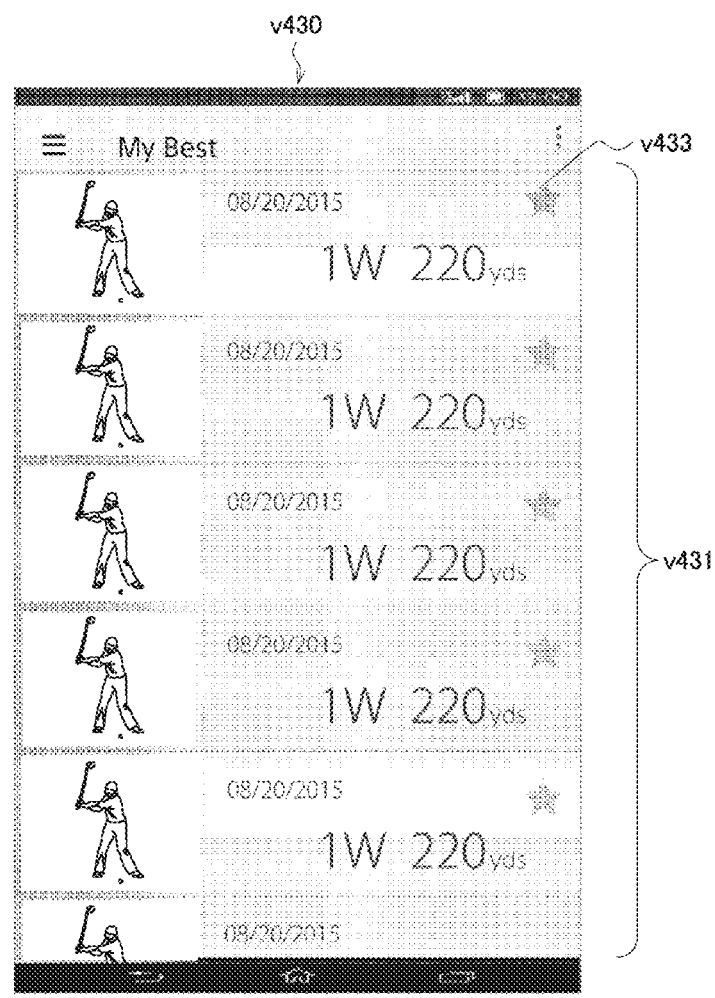
FIG. 48 is a diagram illustrating an example of a screen for suggesting a list of data registered as favorites in the UI according to the embodiment.

Next, an example of a screen on which data registered as favorites in advance is suggested as a list, desired data is selected in the list, and information is displayed will be described with reference to FIG. 48. FIG. 48 is a diagram illustrating an example of a screen for suggesting a list of data registered as favorites in the UI according to the embodiment.

Specifically, on a screen v430 illustrated in FIG. 48, data registered as favorites in advance is extracted and a list of the extracted data is presented in a region denoted by reference numeral v431. Note that a part of information corresponding to each piece of data is presented in each item of the list. As a specific example, in the item corresponding to each piece of data, information regarding at least a part of a date on which the data is acquired, information regarding setting related to analysis or simulation, such as a golf club number used in a practice of a swing, information corresponding to an analysis result or a simulation result, and the like is presented. In addition, a thumbnail corresponding to the data may be presented in the item corresponding to each piece of data. For example, in the example illustrated in FIG. 48, a thumbnail of a moving image associated with each piece of data is presented as the thumbnail. On the basis of this configuration, the user may select an item corresponding to desired data (for example, data which is presenting targets of various kinds of information) on the basis of a predetermined manipulation such as a tapping manipulation or the like in the list presented in the region v431.

In addition, an icon denoted by reference numeral v433 is an input interface for selectively switching between registration and cancellation of a favorite in each piece of data. For example, the user can also cancel registration of data corresponding to an item registered as a favorite by manipulating the icon v433 presented in a desired item in the list presented in the region v431.

The example of a screen on which the data registered as the favorites in advance is suggested as the list, the desired data is selected in the list, and the information is displayed has been described with reference to FIG. 48.

(10) Kinematic Sequence/Body Sequence

Next, functions of a kinematic sequence and a body sequence supplied by the information processing system 1 according to the embodiment and an example of a UI corresponding to the functions will be described with reference to FIGS. 49 to 55. For example, FIGS. 49 to 52 and 54 are diagrams illustrating examples of screens corresponding to the function of the kinematic sequence in the UI according to the embodiment. In addition, FIGS. 53 and 55 are diagrams illustrating examples of screens corresponding to the function of the body sequence in the UI according to the embodiment.

First, an overview of the functions of the kinematic sequence and the body sequence will be described. The kinematic sequence is a function of analyzing a movement of each part of the body such as an arm, a thorax, or a pelvis or a movement of an instrument such as a golf club in a series of actions such as a golf swing using the plurality of body sensor devices 100 and the shaft sensor device 200 and presenting an analysis result. Specifically, a movement of each part of the body can be individually analyzed on the basis of a sensing result by the body sensor device 100 worn on the part of the body. Similarly, a movement of an instrument such as a golf club used by the user can be analyzed on the basis of a sensing result by the shaft sensor device 200 mounted on the instrument. In the kinematic sequence, analysis results of movements of an instrument or each part of the body individually acquired in this way are integrated and various kinds of information based on the integrated result are presented. On the basis of this control, for example, how the motions of each part of the body of the user and the instrument used by the user are interlocked in a series of actions of a swing or the like is presented to be visually identifiable in the kinematic sequence. In addition, the body sequence is a function of analyzing a movement of each part of the body such as an arm, a thorax, and a pelvis in a series of actions using the plurality of body sensor devices 100 and presenting an analysis result. The body sequence is the same function as the kinematic sequence except that the sensing result by the shaft sensor device 200 is not used.

Accordingly, hereinafter, the functions of the kinematic sequence and the body sequence will be described in more detail along with an example of a screen of a UI. Note that in the description, the functions of the kinematic sequence and the body sequence will be described particularly focusing on an example of a case in which a golf swing is analyzed.

Figure 49:
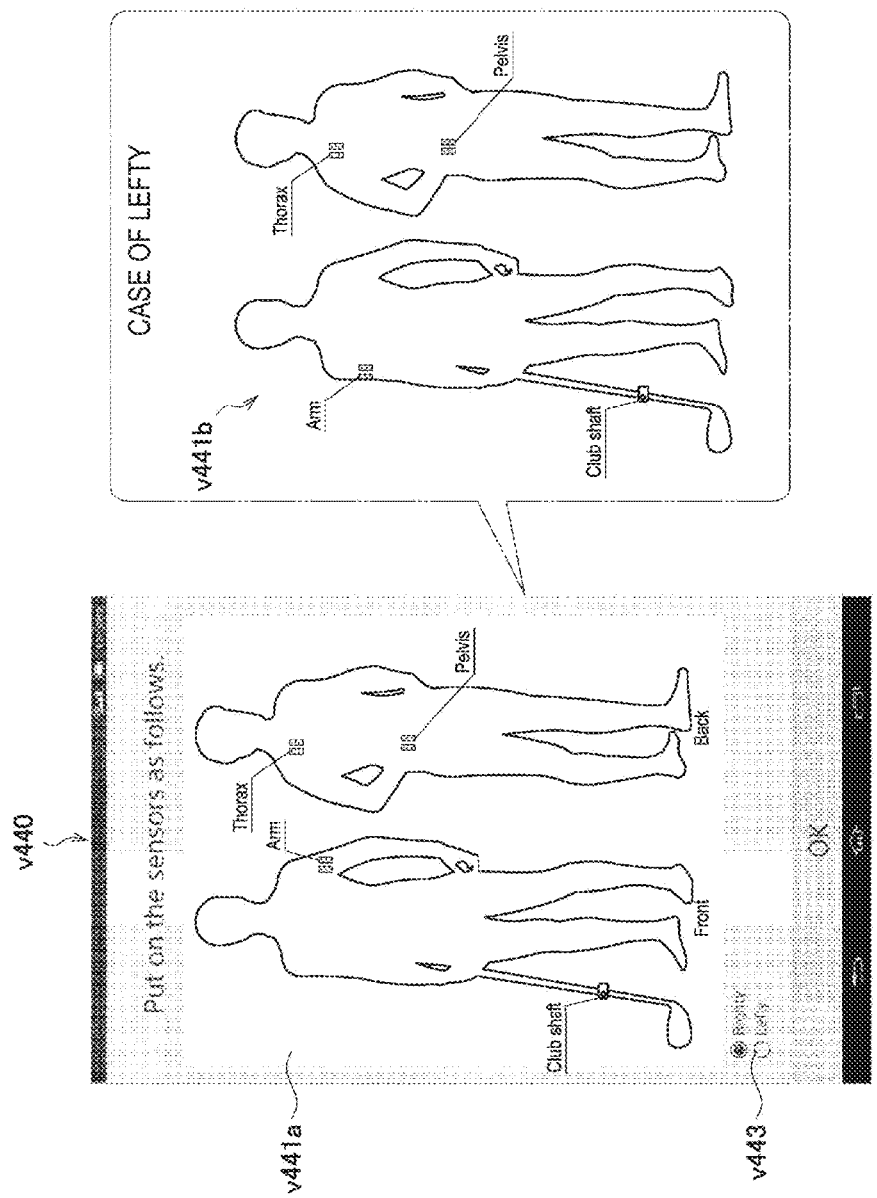
FIG. 49 is a diagram illustrating an example of a screen corresponding to a function of a kinematic sequence in the UI according to the embodiment.

For example, a screen v440 illustrated in FIG. 49 is an example of a screen for presenting an installation position of the body sensor device 100 or the shaft sensor device 200 to the user. As illustrated in FIG. 49, in a case in which a golf swing is analyzed, for example, the body sensor device 100 is individually worn on each of a pelvis, a thorax, and an arm. At his time, each body sensor device 100 is associated in advance with a part of the body on which the body sensor device 100 is worn. For example, a casing with a color appropriate for the part of the body is applied. In addition, on the screen v440, the body sensor device 100 worn on each of the pelvis, the thorax, and the arm is presented with a marker with a color in accordance with the body sensor device 100. For example, in the example illustrated in FIG. 49, as denoted by reference numeral v441a, a silhouette of a human body is presented and a marker with a color corresponding to the body sensor device 100 is presented in a portion corresponding to the part of the body on which the body sensor device 100 is worn. Thus, the user can intuitively recognize on which body part each of the plurality of body sensor devices 100 may be worn.

In addition, in a case in which a golf swing is analyzed, the shaft sensor device 200 is mounted on the shaft of a golf club. Therefore, on the screen v440, as denoted by reference numeral v441a, an installation position of the shaft sensor device 200 is shown by presenting a marker indicating the shaft sensor device 200 on a silhouette of the golf club.

In addition, in a case in which a golf swing is analyzed, it is preferable to analyze a movement of the arm opposite to the dominant arm between the right and left arms. That is, in a case in which the user is right-handed, the body sensor device 100 associated with the arm is worn on his or her left arm. In addition, in a case in which the user is left-handed, the body sensor device 100 associated with the arm is worn on his or her right arm. In this way, since the wearing positions of some of the body sensor devices 100 are different in accordance with a dominant hand of the user, as denoted by reference numeral v433, an input interface for designating the dominant arm is presented as denoted by reference numeral v443 on the screen v440 illustrated in FIG. 49. That is, when the left arm is selected as the dominant arm, for example, a right-handed image denoted by reference numeral v441a is switched and a left-handed image denoted by reference numeral v441b is presented.

Note that, for example, setting of the golf club described with reference to FIG. 21 or calibration of various sensors described with reference to FIG. 22 may be performed as initial setting for using the function of the kinematic sequence or the body sequence.

Next, an example of a screen for setting the body sensor device 100 worn on each part of the body will be described with reference to FIG. 50. For example, on the screen v450 illustrated in FIG. 50, each part of the body can be associated with each body sensor device 100 and feedback in accordance with a movement of each part of the body can be set.

Specifically, as denoted by reference numeral v451, a check box is associated with a candidate part of a wearing position of the body sensor device 100 to be presented. That is, when a check mark is input in the check box, association of the body sensor device 100 with a part of the body corresponding to the check box is designated. In addition, when the check mark is input in the check box v451, an input interface for designating the body sensor device 100 associated with the part of the body corresponding to the check box v451 is presented as denoted by reference numeral v452.

Figure 50:
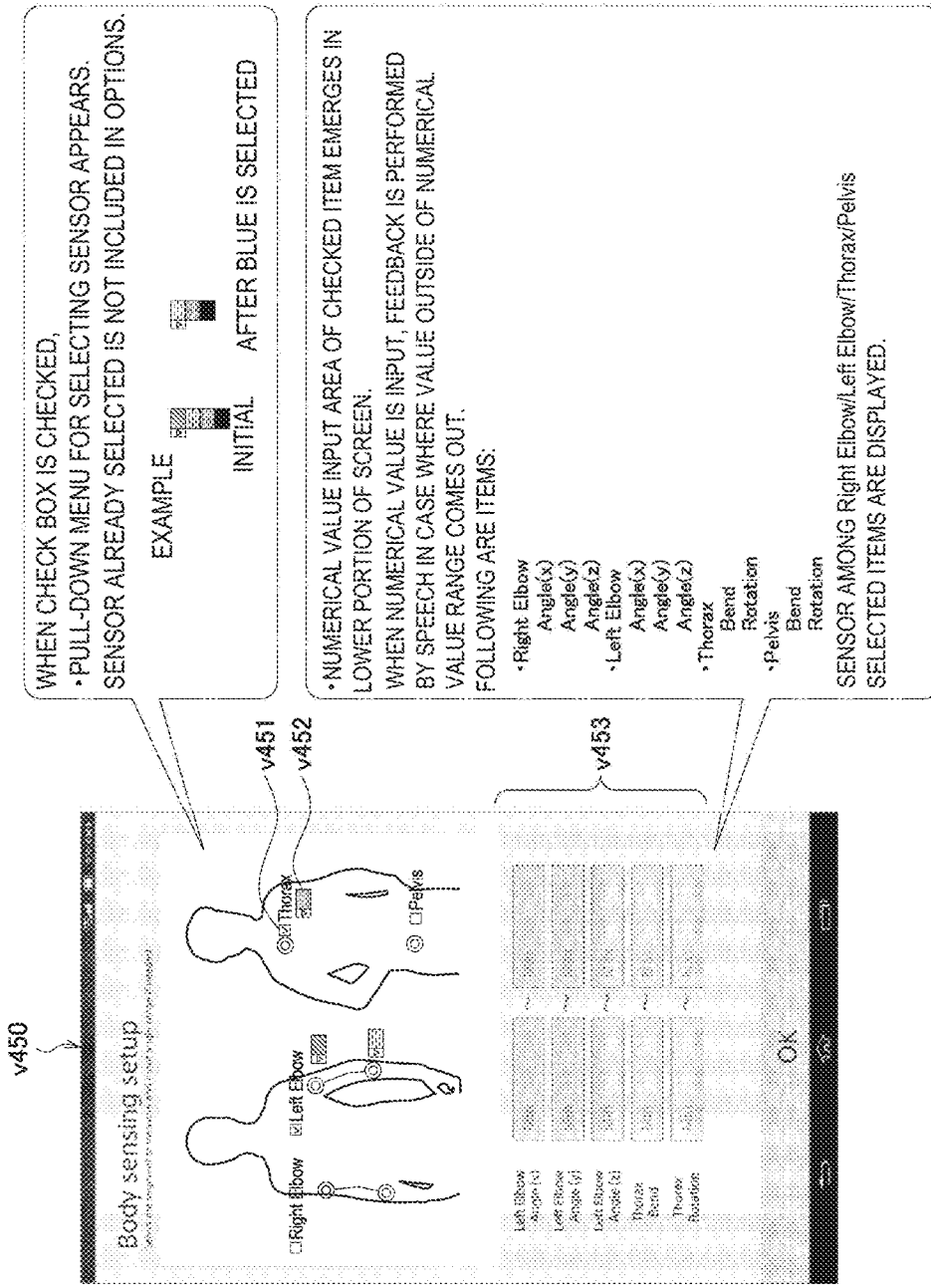
FIG. 50 is a diagram illustrating an example of a screen corresponding to a function of a kinematic sequence in the UI according to the embodiment.

For example, in the example illustrated in FIG. 50, a pull-down menu v452 for designating the desired body sensor device 100 with the color corresponding to the body sensor device 100 is presented as an input interface for selecting each body sensor device 100. For example, in a case in which the body sensor devices 100 to which blue, red, green, and black casings are applied are used as the plurality of body sensor devices 100 worn on parts of the body, items shown with blue, red, green, and black as selection candidates can be presented as a list in the pull-down menu v452. In addition, the body sensor devices 100 to which the casings with mutually different colors are applied are worn on the plurality of parts of the body. Therefore, for example, in a case in which the blue item is selected for a certain part of the body in the pull-down menu v452, the already selected blue item is excluded from the candidates in the pull-down menu v452 corresponding to the other parts of the body.

In addition, an input area for setting a movable range of each part of the body is presented in a region denoted by reference numeral v453. Specifically, an input of information to an input area corresponding to the part of the body selected in the check box v451 is validated among input areas corresponding to the parts of the body presented in the region v453. Note that an input of information is invalidated in the input areas corresponding to the unselected parts of the body. In addition, as examples of settable movable ranges, for example, angles of elbows of the right arm and the left arm, a bending angle or a rotating angle of a thorax, and a bending angle or a rotating angle of a thorax of a pelvis can be exemplified.

As described above, when the movable range is set in each part of the body for which wearing of the body sensor device 100 is designated, for example, the terminal device 500 can feed information back to a user in a case in which each part of the body is moved beyond the set movable range. Thus, the user can recognize that each part of his or her body is moved beyond the movable range set in advance and can also take measures to correct his or her form.

Next, an example of a screen on which an analysis result of a swing form is presented will be described with reference to FIG. 51. For example, on a screen v460 illustrated in FIG. 51, a chronological change in a rotation speed is presented as a line graph in each of each part (that is, the pelvis, the thorax, and an arm) of the body and a golf club at the time of a swing in a region denoted by reference numeral v461. Specifically, in the line graph presented in the region v461, the horizontal axis presents a time and the vertical axis represents a rotation speed. Note that for the rotation speed represented on the vertical axis, when the horizontal axis is a base point, the lower side is equivalent to a rotation speed in a direction of a back swing and the upper side is equivalent to a rotation speed in a direction of a down swing.

In addition, in the line graph presented in the region v461, graphs corresponding to each part (that is, the pelvis, the thorax, and the arm) of the body and the golf club are presented with mutually different colors. At this time, each graph may be presented with the color (for example, the color of the casing of the sensor device) corresponding to the sensor device (for example, the body sensor device 100 or the shaft sensor device 200) serving as an acquisition source of information (sensing result) used to generate the graph.

More specifically, the terminal device 500 calculates a chronological change in a rotation speed of each of the golf club and each part (that is, the pelvis, the thorax, and the arm) of the body on the basis of sensing results by each body sensor device 100 and the shaft sensor device 200. Then, the terminal device 500 makes graphs of chronological changes in the rotation speed of each part of the body and the golf club and puts the time axes of the graphs together to integrate the graphs corresponding to each of the golf club and each part of the body. Thus, as presented in the region v461 of the screen v460 illustrated in FIG. 51, it is possible to present the graphs in which the chronological changes in the rotation speeds are shown for each part of the body and the golf club at the time of a swing.

In addition, in the region v461, a progress bar for controlling reproduction or stop of a moving image of a corresponding swing may also be presented along with the graphs indicating the chronological changes in the rotation speeds of each part of the body and the golf club. For example, in the example illustrated in FIG. 51, a progress bar for controlling reproduction or stop of a moving image is presented so that the horizontal axis of a graph for a reproduction time of a moving image can be associated with the horizontal axis of the graphs. In this configuration, for example, a corresponding moving image can be reproduced from a reproduction time corresponding to a timing at which a rotation speed of each part of the body is the maximum.

As described above, when the graphs indicating the rotation speeds of each part of the body and the golf club are integrated so that the time axes are presented to be put together, the user can recognize how the rotation speeds of each body part of the body and the golf club are changed in a series of swing actions. In particular, in a golf swing, it is considered that a form in which the rotation speed is the maximum in the order of the pelvis, the thorax, the arm, and the golf club until an impact timing is preferable. Therefore, the user can confirm whether his or her swing form is an ideal state on the basis of the graphs presented in the region v461. In addition, the user is expected to extract a problem of a swing form by comparing data of his or her swing to data of an ideal swing.

In addition, a reproduction result of a moving image corresponding to a swing in which the graphs are presented in the region v461 is displayed in a region denoted by reference numeral v462. Note that reproduction or stop of the moving image is controlled through a manipulation via the progress bar presented in the region v461.

In addition, an image (for example, CG) in which a position or a posture of each part of the body or the golf club is simulated 3-dimensionally is presented in a region denoted by reference numeral v463. Specifically, the terminal device 500 recognizes a 3-dimensional position or posture of each of the golf club and each part (that is, the pelvis, the thorax, and the arm) of the body on the basis of sensing results of each body sensor device 100 and the shaft sensor device 200. Then, the terminal device 500 may simulate the position or the posture of each part of the body or the golf club on the basis of a recognition result of the position or the posture of each of the golf club and each part of the body on which the body sensor device 100 is worn and may generate an image to be presented in the region v463 on the basis of a simulation result.

In addition, in the image presented in the region v463, the part on which each sensor device (that is, the body sensor device 100 or the shaft sensor device 200) is worn and a part corresponding to an instrument is presented with a different color from the other portions. As a specific example, in the example illustrated in FIG. 51, the part on which the sensor device is worn or the golf club is presented with a color corresponding to the sensor device (for example, the color of the casing of the sensor device). From this configuration, for example, the user can intuitively recognize a correspondent relation between each graph presented in the region v461 and each portion of the image presented in the region v463.

In addition, display of the image presented in the region v463 may be controlled such that a viewpoint is rotated 3-dimensionally through a manipulation such as dragging, or the display of the image maybe controlled so that the image is expanded or contracted through a manipulation such as pinch-out and pinch-in. In addition, in a portion corresponding to each part of the body or the golf club on which any of various sensor devices is worn, information based on a sensing result by the sensor device may be associated to be presented. For example, in the example illustrated in FIG. 51, a calculation result of an angle of a corresponding portion is presented in a portion corresponding to each of the pelvis, the thorax, the arm, and the golf club in the image presented in the region v463.

In addition, the image presented in the region v463 may also be presented as a moving image in which a chorological change in the position or the posture of each part of the body or the golf club is reproduced as an animation to be synchronized with the reproduction result of the moving image displayed in the region v462.

Information based on an analysis result of a movement of each portion at the time of a swing is displayed in a region denoted by reference numeral v464. For example, in the example illustrated in FIG. 51, in the region v464, information based on an analysis result of rotation of the pelvis is presented at a timing of each of an address (Address), a top (Top), an impact (Impact), and a finish (Finish) in a series of swing flows. Note that the example illustrated in FIG. 51 is merely an example and types of information displayed in the region v464 are not particularly limited. For example, information regarding a part of the body on which the body sensor device 100 is worn, such as an arm or a thorax, may be displayed without being limited to the information regarding the pelvis. In addition, as the information regarding each part of the body such as the pelvis or the thorax, for example, information regarding a position, a posture, or the like of each part of the body, such as a bending angle of the pelvis or the thorax, may be presented without being limited to the information regarding the rotation speed. In addition, as the information regarding the golf club, for example, information indicating a head speed, an inclination angle of a face, a swing pass, an attack angle, and the like may be presented. In addition, the information presented in the region v464 may be selectively switched through a predetermined manipulation. As a specific example, information displayed in the region v464 may be switched in sequence in a case in which a swiping manipulation is performed in the horizontal direction on the region v464.

In addition, on the screen v460, in a case in which information regarding each portion on which each sensor device is worn is presented as text information, at least a part of the text information may be presented with a color corresponding to the sensor device. For example, in the example illustrated in FIG. 51, the information regarding the rotation of the pelvis is presented in the region v464. Therefore, an item name of the information presented in the region v464 is presented with the same color as the color (for example, the color of the casing) corresponding to the body sensor device 100 worn on the pelvis. Thus, the user can intuitively recognize an analysis result of a movement of a part to which the presented information corresponds.

In addition, as denoted by reference numeral v465, an indicator indicating an analysis preparation situation of a subsequent swing may be presented on the screen v460.

In addition, the information presented in each region of the screen v460 may be expanded and displayed on the basis of a predetermined manipulation. For example, a screen v470 illustrated in FIG. 52 shows an example of a case in which an image presented in the region v463 in the example illustrated in FIG. 51 is expanded and displayed.

Figure 51:
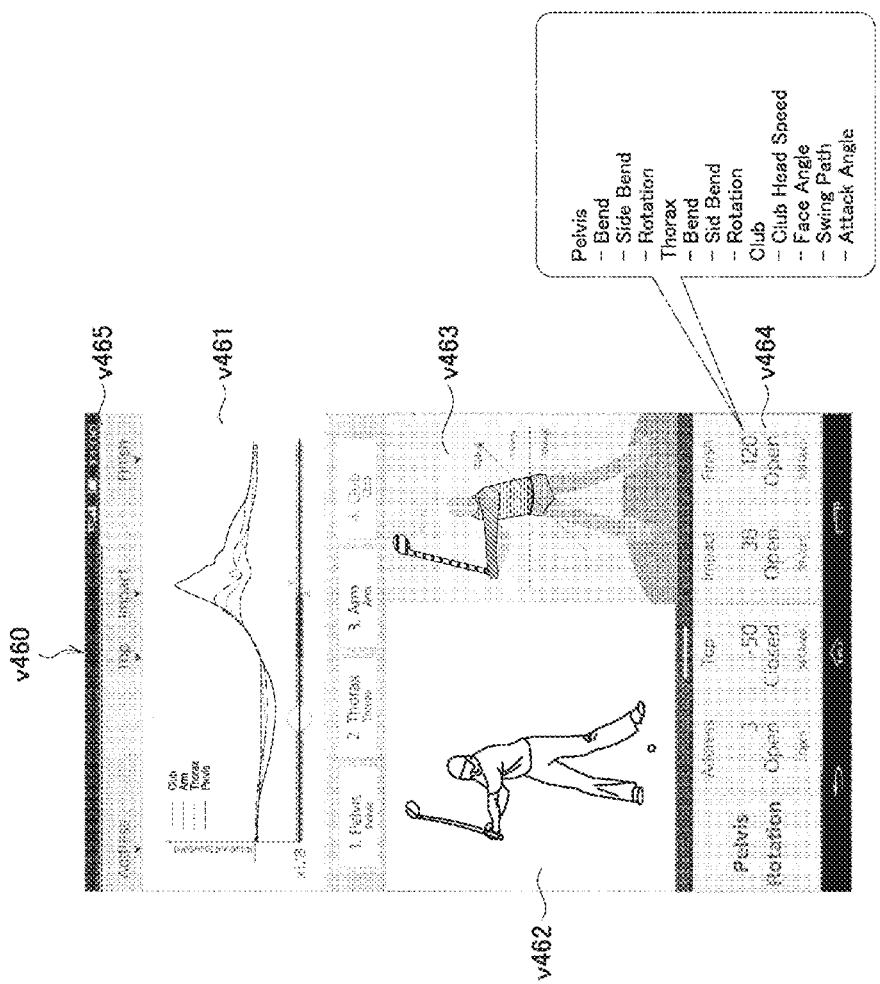
FIG. 51 is a diagram illustrating an example of a screen corresponding to a function of a kinematic sequence in the UI according to the embodiment.

For example, in a region denoted by reference numeral v473, the image presented in the region v463 in the example illustrated in FIG. 51 is presented similarly. In addition, a progress bar for controlling reproduction or stop of a moving image in which a chronological change in the position or the posture of each part of the body or the golf club is reproduced as an animation may be presented in the region v473.

In addition, the information presented in the region v464 in the example illustrated in FIG. 51 is presented similarly in a region denoted by reference numeral v471. Note that the information presented in the region v471 may be selectively switched on the basis of a predetermined manipulation, like the information presented in the region v464 in the example illustrated in FIG. 51.

Figure 52:
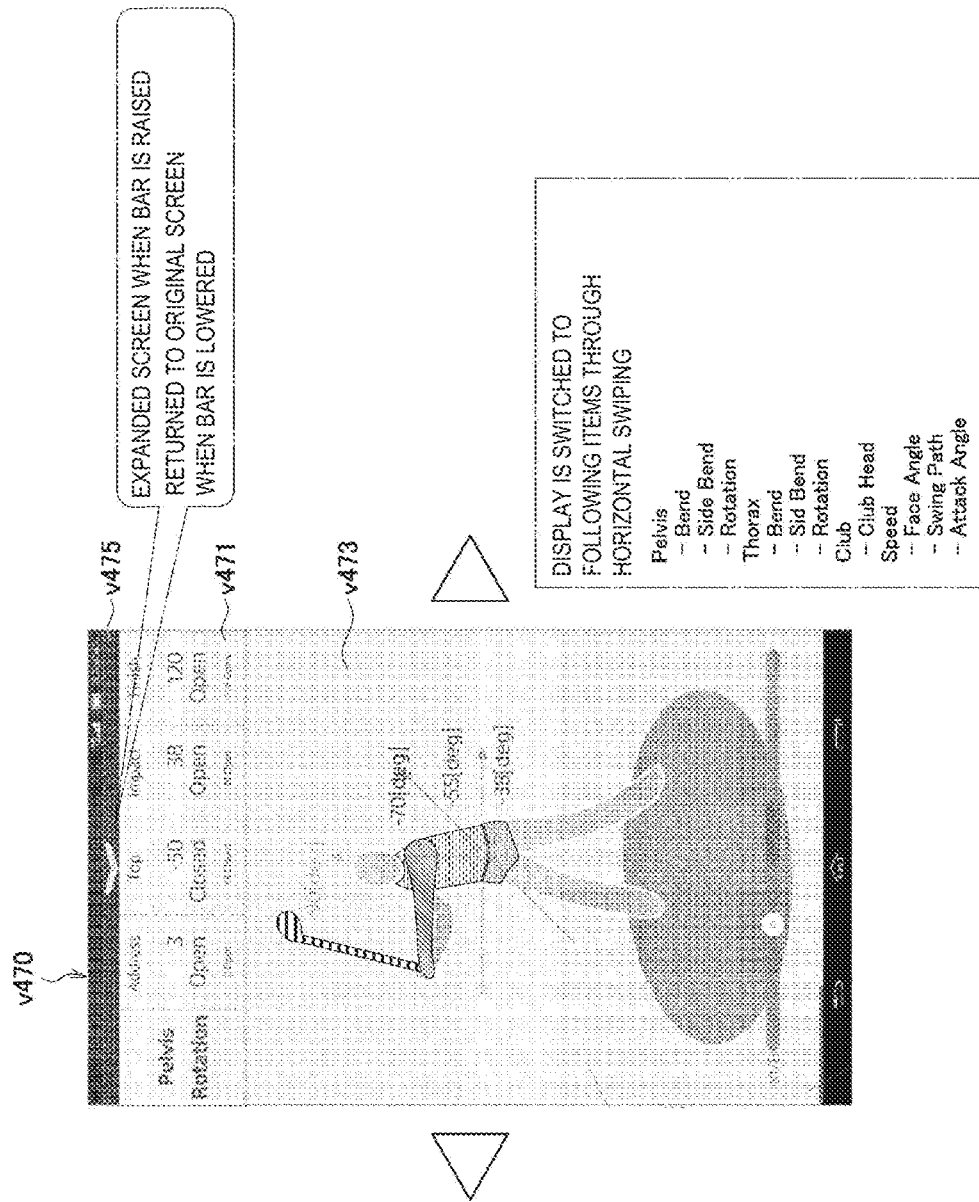
FIG. 52 is a diagram illustrating an example of a screen corresponding to a function of a kinematic sequence in the UI according to the embodiment.
Figure 53:
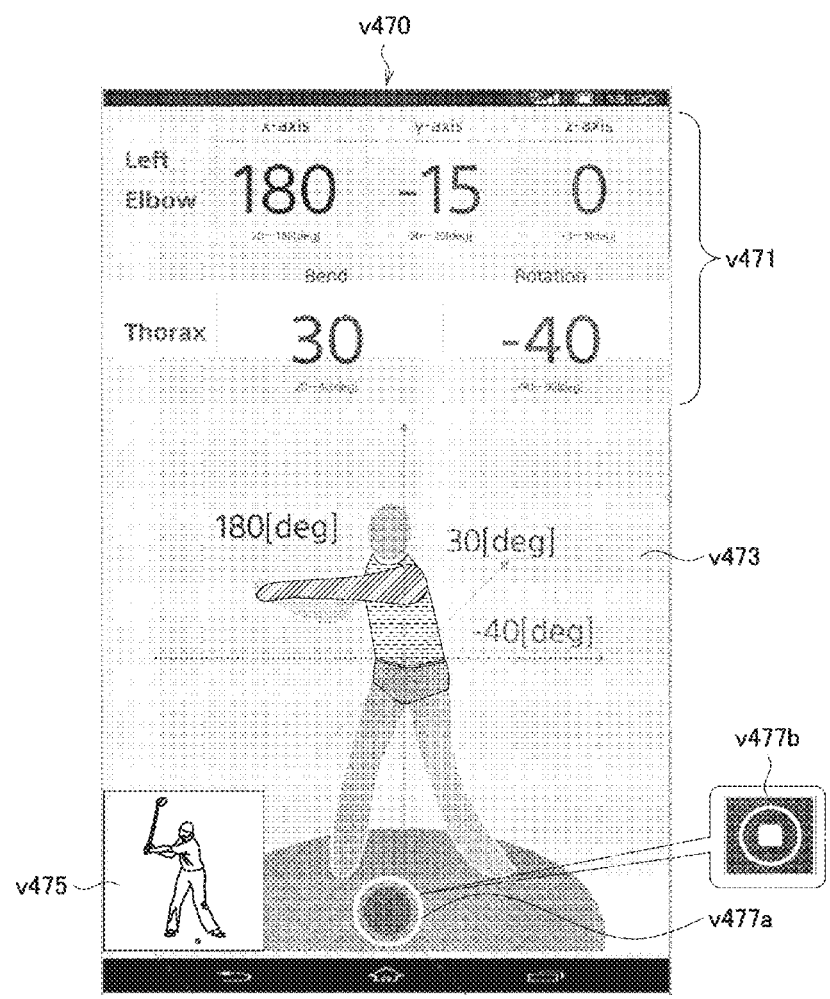
FIG. 53 is a diagram illustrating an example of a screen corresponding to a function of a body sequence in the UI according to the embodiment.

In addition, the screen v470 illustrated in FIG. 52 is presented in a case in which, for example, a manipulation is performed so that display information v475 with a bar shape presented at a predetermined position on the screen v460 illustrated in FIG. 51 is raised upward through dragging or the like. In addition, in a case in which a manipulation is performed so that the display information v475 with the bar shape is lowered in the lower direction through dragging or the like in the state in which the screen v470 is presented, another screen (for example, the screen v460 illustrated in FIG. 51) which is a calling source of the screen v470 is presented.

Next, an example of a UI of the function of the body sequence will be described with reference to FIG. 53. As described above, the function of the body sequence is a function of analyzing movements of a plurality of parts (for example, the pelvis, the thorax, and an arm) of the body in a series of actions using the plurality of body sensor devices 100 and presenting an analysis result. For example, on the screen v470 illustrated in FIG. 53, movements of the thorax and the left arm are analyzed and information based on the analysis result is presented.

Specifically, in the region denoted by the region v471, a detection result of a posture of each part of the body based on a sensing result by each body sensor device 100 is presented as numerical information. As a specific example, numerical information indicating a detection result of an angle of a left arm is presented on axes x, y, and z as the information indicating the analysis result of the posture of the left arm. In addition, numerical information indicating a bending angle or a rotational angle of the thorax is presented as the information indicating the analysis result of the posture of the thorax.

In addition, in the region denoted by reference numeral v473, an image (for example, CG) in which the position or the posture of each part of the body is simulated 3-dimensionally is presented. Specifically, the terminal device 500 recognizes a 3-dimensional position or posture of each part (for example, the thorax, and the left arm) of the body on the basis of sensing results of each body sensor device 100. Then, the terminal device 500 may simulate the position or the posture of each part of the body on the basis of a recognition result of the position or the posture of each part of the body on which the body sensor device 100 is worn and may generate an image to be presented in the region v463 on the basis of a simulation result.

In addition, in the image presented in the region v473, a portion corresponding to the part of the body on which each body sensor device 100 is worn is presented with a different color from the other portions. As a specific example, in the example illustrated in FIG. 53, the part on which the sensor device is worn is presented with a color corresponding to the sensor device (for example, the color of the casing of the sensor device).

In addition, display of the image presented in the region v473 may be controlled such that a viewpoint is rotated 3-dimensionally through a manipulation such as dragging, or the display of the image maybe controlled so that the image is expanded or contracted through a manipulation such as pinch-out and pinch-in.

In addition, in a portion corresponding to each part on which any of various sensor devices is worn, information based on a sensing result by the sensor device may be associated to be presented. For example, in the example illustrated in FIG. 53, information indicating a calculation result of each of an angle of the left arm in the x axis direction, a bending angle of the thorax, and a rotational angle of the thorax in the image presented in the region v473 is associated with a corresponding position to be presented. In addition, at this time, each of the numerical information presented in the region v473 and corresponding information in the numerical information presented in the region v471 may be presented in the same display mode. For example, in the example illustrated in FIG. 53, each of the numerical information presented in the region v473 and the corresponding information in the numerical information presented in the region v471 are presented with the same color. From this configuration, for example, the user can intuitively recognize a correspondent relation between each piece of information presented in the region v471 and each piece of information presented in the region v473.

In addition, the image presented in the region v473 may be presented as a moving image in which a chronological change in the position or the posture of each part of the body is reproduced as an animation. In addition, at this time, in a case in which a moving image based on an imaging result of a swing which is an information presenting target is associated with data of the swing, as denoted by reference numeral v475, a moving image based on the imaging result may also be presented together.

In addition, a function of capturing the image (that is, the moving image) presented in the region v473 may be installed. For example, in the example illustrated in FIG. 53, input interfaces for controlling start and stop of capturing are presented as icons denoted by reference numerals v477a and v477b. Specifically, the icon v477a is an input interface for giving an instruction to start capturing and is presented during stop of the capturing. That is, when the icon v477a is manipulated through a tapping manipulation or the like, capturing an image starts. In addition, the icon v477b is an input interface for giving an instruction to stop the capturing and is presented during execution of the capturing. That is, when the icon v477b is manipulated through a tapping manipulation or the like, capturing an image during execution stops.

Note that the screens described with reference to FIGS. 49 to 53 are merely examples and types of information to be displayed on each screen, a display mode of each piece of information, a layout, and the like are not necessarily limited to the above-described examples.

Figure 54:
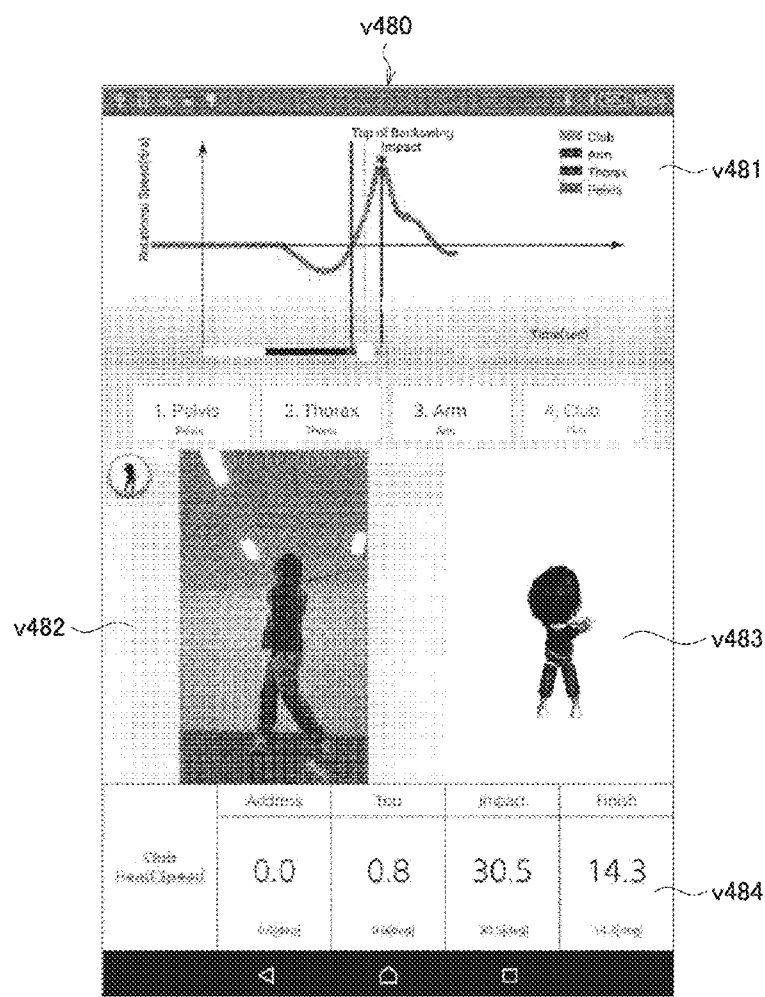
FIG. 54 is a diagram illustrating an example of a screen corresponding to a function of a kinematic sequence in the UI according to the embodiment.
Figure 55:
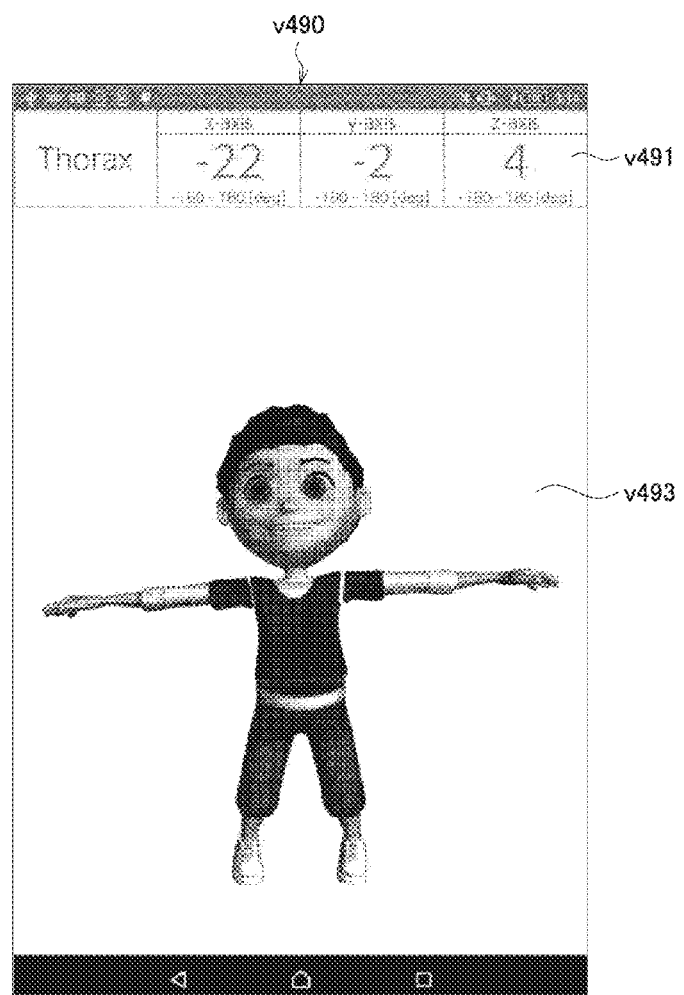
FIG. 55 is a diagram illustrating an example of a screen corresponding to a function of a body sequence in the UI according to the embodiment.

For example, FIG. 54 illustrates another example of a screen corresponding to the function of the kinematic sequence. Specifically, on a screen v480 illustrated in FIG. 54, regions denoted by reference numerals v481 to v484 respectively correspond to the regions v461 to v464 of the screen v460 described with reference to FIG. 51. On the other hand, on the screen v480 illustrated in FIG. 54, the image presented in the region v463 illustrated in FIG. 51 is switched to an avatar of a user registered in advance is presented as an image presented in the region v483. That is, in the example illustrated in FIG. 54, a position or a posture (furthermore, a form at the time of a swing) of each part of the user at the time of a swing is presented visually in accordance with the position or the posture of each part of the avatar presented in the region v483.

In addition, as another example, FIG. 55 illustrates another example of a screen corresponding to the function of the body sequence. Specifically, on a screen v490 illustrated in FIG. 55, regions denoted by reference numerals v491 and v493 respectively correspond to the regions v471 and v473 of the screen v470 described with reference to FIG. 52. On the other hand, on the screen v490 illustrated in FIG. 56, the image presented in the region v473 illustrated in FIG. 52 is switched to an avatar of a user registered in advance is presented as an image presented in the region v493. That is, in the example illustrated in FIG. 55, a position or a posture (furthermore, a form at the time of a swing) of each part of the user at the time of a swing is presented visually in accordance with the position or the posture of each part of the avatar presented in the region v493.

The functions of the kinematic sequence and the body sequence supplied by the information processing system 1 according to the embodiment and the examples of the UIs corresponding to the functions have been described above with reference to FIGS. 49 to 55.

<3.3. Evaluation>

As described above, in the information processing system 1 according to the embodiment, by using the sensing results by the body sensor devices 100, the shaft sensor device 200, or the like according to the above-described embodiment, it is possible to analyze the movements of the body of the user and present the information indicating the analysis results. In addition, in the information processing system 1, by integrating each piece of information without being limited to the individual presentation of the information indicating the analysis result of the movement of each body part, the golf club, or the like, it is also possible to present the movement of each part in a series of actions of a swing or the like as visualized data such as a graph. From this configuration, for example, the user can also confirm how each part such as the pelvis, the thorax, and an arm and an instrument such as a golf club in a series of movements of a swing or the like are interlocked and moved on the basis of quantitative numerical information, the visualized data, and the like.

In addition, as described with reference to FIG. 15, the information processing system 1 according to the embodiment can be realized by each sensor device such as the body sensor device 100 or the shaft sensor device 200 and the terminal device 500 such as a smartphone. In addition, the function of analyzing a sensing result by the body sensor device 100 or the shaft sensor device 200 can be realized by installing a predetermined application in the terminal device 500. Therefore, according to the information processing system 1 according to the embodiment, a system in which a movement of the body (for example, a swing) is sensed to carry out various kinds of analysis can be realized at lower cost with a simpler configuration without involving a large-scale device.

4. Conclusion

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
An information processing device including:
a first member that includes a substantially plate-shaped casing and a predetermined detection unit;
a second member that includes a substantially plate-shaped casing and that holds a battery inside the second member; and
a connection unit that includes an elastic body and connects a part of an outer circumferential end surface of the first member to a part of an outer circumferential end surface of the second member such that a surface direction of one surface of the first member substantially matches a surface direction of one surface of the second member,
in which the information processing device is worn on a predetermined body part such that the one surface of the first member and the one surface of the second member are located on a side of the body part.

(2)
The information processing device according to (1),
in which the connection unit includes a restriction member that restricts a change of a relative position relation between the first member and the second member within a predetermined range.

(3)
The information processing device according to (2),
in which the restriction member is a member that has a wire shape installed to extend from a part of the outer circumferential end surface of the first member to a part of the outer circumferential end surface of the second member.

(4)
The information processing device according to any one of (1) to (3),
in which the first member includes an input unit.

(5)
The information processing device according to (4),
in which the input unit is installed on another surface opposite to the one surface of the first member.

(6)
The information processing device according to any one of (1) to (5),
in which each of the one surface of the first member and the one surface of the second member has a rectangular shape having a longitudinal direction and a transverse direction, and
the connection unit connects an end surface extending in the longitudinal direction in the outer circumferential end surface of the first member to an end surface extending in the longitudinal direction in the outer circumferential end surface of the second member.

(7)
The information processing device according to (6),
in which the second member is formed such that the battery is insertable and detachable.

(8)
The information processing device according to (7),
in which in the second member, the battery is inserted and detached in the longitudinal direction from a side of an end surface extending in the transverse direction in the outer circumferential end surface.

(9)
The information processing device according to any one of (6) to (8),
in which the first member includes a communication unit communicating with another device via a wireless communication path.

(10)
The information processing device according to (9),
in which an antenna element connected to the communication unit is installed on a side of an end surface located opposite to an end surface connected to the second member by the connection unit in the outer circumferential end surface of the first member.

REFERENCE SIGNS LIST 1 information processing system
100 body sensor device
110 manipulation unit
111 casing
115 input unit
120 battery unit
121 casing
130 manipulation unit body
131 connection unit
133 restriction member
140 battery
150 substrate unit
151 sensor substrate
160 antenna unit
200 shaft sensor device 210 body unit
211 casing
213 input unit
215 mounting portion
217 charging terminal
219 reset switch
230 unit
231 gripping member
233 casing
235 lock mechanism
237 fitting portion
239 support portion
300 holder
310 belt unit
320 pocket unit
330 through hole
500 terminal device
510 imaging unit
530 output unit

The invention claimed is:

1. An information processing device, comprising:
a first member that includes a first substantially plate-shaped casing and a determined detection unit;
a second member that includes a second substantially plate-shaped casing, wherein the second member is configured to hold a battery inside the second member;
a connection unit that includes an elastic body, wherein the connection unit is configured to connect a part of an outer circumferential end surface of the first member to a part of an outer circumferential end surface of the second member, such that a surface direction of a first surface of the first member substantially matches a surface direction of a surface of the second member; and
a restriction member configured to restrict a change of a relative position relation between the first member and the second member within a determined range, wherein
the restriction member includes a material having a higher rigidity than the connection unit, and
the information processing device is worn on a determined body part such that the first surface of the first member and the surface of the second member are located on a side of the determined body part.

2. The information processing device according to claim 1, wherein the restriction member has a wire shape installed to extend from the part of the outer circumferential end surface of the first member to the part of the outer circumferential end surface of the second member.

3. The information processing device according to claim 1, wherein the first member further includes an input unit.

4. The information processing device according to claim 3, wherein the input unit is installed on a second surface of the first member which is opposite to the first surface of the first member.

5. The information processing device according to claim 1, wherein
each of the first surface of the first member and the surface of the second member has a rectangular shape having a longitudinal direction and a transverse direction, and
the connection unit is further configured to connect an end surface extending in the longitudinal direction in the outer circumferential end surface of the first member to an end surface extending in the longitudinal direction in the outer circumferential end surface of the second member.

6. The information processing device according to claim 5, wherein the second member is formed such that the battery is insertable and detachable.

7. The information processing device according to claim 6, wherein in the second member, the battery is inserted and detached in the longitudinal direction from a side of an end surface extending in the transverse direction in the outer circumferential end surface.

8. The information processing device according to claim 5, wherein the first member further includes a communication unit configured to communicate with an external device via a wireless communication path.

9. The information processing device according to claim 8, further comprising an antenna element connected to the communication unit, wherein the antenna element is installed on a side of a first end surface of the first member located opposite to a second end surface of the first member which is connected to the second member by the connection unit in the outer circumferential end surface of the first member.

10. An information processing device, comprising:
a first member that includes a first substantially plate-shaped casing and a determined detection unit;
a second member that includes a second substantially plate-shaped casing, wherein the second member is configured to hold a battery inside the second member;
a connection unit that includes an elastic body, wherein the connection unit is configured to connect a part of an outer circumferential end surface of the first member to a part of an outer circumferential end surface of the second member, such that a surface direction of a surface of the first member substantially matches a surface direction of a surface of the second member; and
a restriction member configured to restrict a change of a relative position relation between the first member and the second member within a determined range, wherein
the restriction member has a wire shape installed to extend from the part of the outer circumferential end surface of the first member to the part of the outer circumferential end surface of the second member, and
the information processing device is worn on a determined body part such that the surface of the first member and the surface of the second member are located on a side of the determined body part.

11. An information processing device, comprising:
a first member that includes a first substantially plate-shaped casing and a determined detection unit;
a second member that includes a second substantially plate-shaped casing, wherein the second member is configured to hold a battery inside the second member, wherein each of a surface of the first member and a surface of the second member has a rectangular shape having a longitudinal direction and a transverse direction;
a connection unit that includes an elastic body, wherein the connection unit is configured to connect an end surface extending in the longitudinal direction in an outer circumferential end surface of the first member to an end surface extending in the longitudinal direction in an outer circumferential end surface of the second member, such that a surface direction of the surface of the first member substantially matches a surface direction of the surface of the second member;

a communication unit in the first member, wherein the communication unit is configured to communicate with an external device via a wireless communication path; and an antenna element connected to the communication unit, wherein
  the antenna element is installed on a side of a first end surface of the first member located opposite to a second end surface of the first member which is connected to the second member by the connection unit in the outer circumferential end surface of the first member, and
  the information processing device is worn on a determined body part such that the surface of the first member and the surface of the second member are located on a side of the determined body part.

\* \* \* \* \*